(12) United States Patent
Farha et al.

(10) Patent No.: US 9,216,939 B2
(45) Date of Patent: Dec. 22, 2015

(54) METAL-ORGANIC FRAMEWORK MATERIALS WITH ULTRAHIGH SURFACE AREAS

(71) Applicant: Northwestern University, Evanston, IL (US)

(72) Inventors: Omar K. Farha, Morton Grove, IL (US); Joseph T. Hupp, Northfield, IL (US); Christopher E. Wilmer, Evanston, IL (US); Ibrahim Eryazici, Chicago, IL (US); Randall Q. Snurr, Evanston, IL (US); Diego A. Gomez-Gualdron, Evanston, IL (US); Bhaskarjyoti Borah, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 177 days.

(21) Appl. No.: 13/920,828

(22) Filed: Jun. 18, 2013

(65) Prior Publication Data
US 2014/0005428 A1    Jan. 2, 2014

Related U.S. Application Data

(60) Provisional application No. 61/661,194, filed on Jun. 18, 2012.

(51) Int. Cl.
| | |
|---|---|
| *C07F 19/00* | (2006.01) |
| *B01J 31/16* | (2006.01) |
| *C07C 63/66* | (2006.01) |
| *B01J 20/22* | (2006.01) |
| *C07F 1/00* | (2006.01) |
| *B01J 20/28* | (2006.01) |

(Continued)

(52) U.S. Cl.
CPC ............... *C07C 63/66* (2013.01); *B01J 20/226* (2013.01); *B01J 20/28066* (2013.01); *B01J 20/28076* (2013.01); *B01J 20/3085* (2013.01); *C07F 1/005* (2013.01); *F17C 11/005* (2013.01)

(58) Field of Classification Search
CPC .... B01J 31/1691; C07F 19/005; F17C 11/005
USPC ...................... 556/42, 45, 51, 61, 64, 81, 110
See application file for complete search history.

(56) References Cited

U.S. PATENT DOCUMENTS

2012/0172612 A1    7/2012 Yaghi et al.

OTHER PUBLICATIONS

Farha et al., Nature Chemistry, vol. 2, pp. 944-948 (2010).*

(Continued)

*Primary Examiner* — Porfirio Nazario Gonzalez
(74) *Attorney, Agent, or Firm* — The Marbury Law Group PLLC

(57) ABSTRACT

A metal organic framework (MOF) material including a Brunauer-Emmett-Teller (BET) surface area greater than 7,010 m²/g. Also a metal organic framework (MOF) material including hexa-carboxylated linkers including alkyne bond. Also a metal organic framework (MOF) material including three types of cuboctahedron cages fused to provide continuous channels. Also a method of making a metal organic framework (MOF) material including saponifying hexaester precursors having alkyne bonds to form a plurality of hexa-carboxylated linkers including alkyne bonds and performing a solvothermal reaction with the plurality of hexa-carboxylated linkers and one or more metal containing compounds to form the MOF material.

42 Claims, 30 Drawing Sheets
(27 of 30 Drawing Sheet(s) Filed in Color)

(51) Int. Cl.
B01J 20/30 (2006.01)
F17C 11/00 (2006.01)

(56) References Cited

OTHER PUBLICATIONS

Allendorf, et al., "Luminescent metal-organic frameworks", Chem. Soc. Rev. 2009, 38, 1330.
An et al., "Metal-adeninate vertices for the construction of an exceptionally porous metal-organic framework." Nat. Commun. 2012, 3, 604.
An et al., "High and Selective CO2 Uptake in a Cobalt Adeninate Metal-Organic Framework Exhibiting Pyrimidine- and Amino-Decorated Pores", J. Am. Chem. Soc., 2010, 132, 38.
An et al., "Tuning MOF $CO_2$ Adsorption Properties via Cation Exchange", J. Am. Chem. Soc., 2010, 132, 5578-5579.
Bae et al, "Enhancement of CO2/N2 selectivity in a metal-organic framework by cavity modification", J. Mater. Chem., 2009, 19, 2131.
Bae et al., "Evaluation of the BET Method for Determining Surface Areas of MOFs and Zeolites that Contain Ultra-Micropores", Langmuir 2010, 26, 5475-5483.
Britt et al., "Highly efficient separation of carbon dioxide by a metal-organic framework replete with open metal sites", Proc. Natl. Acad. Sci. U.S.A., 2009,106, 20637.
Chae et al., "A route to high surface area, porosity and inclusion of large molecules in crystals", Nature, vol. 427, pp. 523-527 , (2004).
Connolly, M. L., "Solvent-Accessible Surfaces of Proteins and Nucleic Acids", Science 1983, 221, 709.
Czepirski et al., "Virial-type thermal equation of gas—solid adsorption",J. Chem. Eng. Sci. 1989, 44, 797-801.
Denysenko et al., "Elucidating Gating Effects for Hydrogen Sorption in MFU-4-Type Triazolate-Based Metal—Organic Frameworks Featuring Different Pore Sizes", Chem. Eur. J. 2011, 17, 1837-1848.
Doak et al., "Synthesis of Unsymmetrical 1,1'-Disubstituted Bis(1,2,3-triazole)s Using Monosilylbutadiynes", Org. Lett. 2011, 13, 537-539.
Duren et al., "Calculating Geometric Surface Areas as a Characterization Tool for Metal—Organic Frameworks",J. Phys. Chem. 2007, 111, 15350.
Eryazici et al., "Luminescent infinite coordination polymer materials from metal-terpyridine ligation", Dalton Trans. 2011, 40, 9189-93.
Farha et al., "Designing Higher Surface Area Metal-Organic Frameworks: Are Triple Bonds Better that Phenyls?" J. Am. Chem. Soc., vol. 134, pp. 9860-9863 (2012).
Farha et al., "De Novo Synthesis of a Metal-Organic Framework Material Featuring Ultra-High Surface Area and Extraordinary Gas Storage Capacities," Nature Chem., 2, 2010, 944-948.
Farha et al., "Metal-Organic Framework Materials with Ultrahigh Surface Areas: Is the Sky the Limit?", J. Am. Chem. Soc., vol. 134, pp. 15016-15021, 2012.
Farha et al., "Rational Design, Synthesis, Purification, and Activation of Metal-Organic Framework Materials", Acc. Chem. Res. 2010, 43, 1166.
Ferey, G., "Hybrid porous solids: past, present, future", Chem Soc. Rev. 2008, 37, 191-214.
Férey, et al., "A Chromium Terephthalate-Based Solid with Unusually Large Pore Volumes and Surface Area", Science 2005, 309, 2040-2042.
Frost et al., "Effects of Surface Area, Free Volume, and Heat of Adsorption on Hydrogen Uptake in Metal-Organic Frameworks", J. Phys. Chem. B 2006, 110, 9565.
Furukawa et al., "Ultrahigh Porosity in Metal-Organic Frameworks", Science, vol. 329, pp. 424-428 (2010).
Furukawa et al., "Independent verification of the saturation hydrogen uptake in MOF-177 and establishment of a benchmark for hydrogen adsorption in metal-organic frameworks", J.Mater. Chem. 2007, 17, 3197-3204.
Getman et al., "Review and analysis of molecular simulations of methane, hydrogen, and acetylene storage in metal-organic frameworks," Chem. Rev. (Washington, D.C., U.S.) 2011; pub. Chem. Rev., 112, 703-723 (2012).
Gómez-Gualdrón et al., "Effect of ethynyl and phenyl groups positions in metal-organic framework organic linkers on methane storage performance".
Han, D et al., "A non-interpenetrated porous metal-organic framework with high gas-uptake capacity", Chem. Commun. 2011, 47, 9861-9863.
Horcajada et al., "Metal-organic frameworks as efficient materials for drug delivery", Angew. Chem., Int. Ed. 2006, 45, 5974.
Horcajada et al., "Metal-Organic Frameworks in Biomedicine", Chem. Rev. (Washington, D.C., U.S.) 2011.
Horike et al., "Self Porous Crystals", Nature Chem., 2009, 1, 695-704.
Mercedes Benz F125 Concept found at: http://www.caranddriver.com/news/mercedes-benz-f125-concept-auto-shows.
Hu et al., "Hydrogen Storage in Metal-Organic Frameworks", Adv. Mater., 2010, 22, E117-E130.
Kaye, et al., "Impact of Preparation and Handling on the Hydrogen Storage Properties of $Zn_4O(1,4$-benzenedicarboxylate$)_3$ (MOF-5)", J. Am. Chem. Soc. 2007, 129, 14176-14177.
Kent et al, "Energy Transfer Dynamics in Metal-Organic Frameworks", J. Am. Chem. Soc., 2010, 132, 12767-12769.
Klein et al., "Route to a Family of Robust, Non-interpenetrated Metal-Organic Frameworks with pto-like Topology", Chem. Eur. J. 2011, 17, 13007-13016.
Koh et al., "A Crystalline Mesoporous Coordination Copolymer with High Microporosity", Angew. Chem., Int. Ed. 2008, 47, 677-680.
Koh et al., "A Porous Coordination Copolymer with over 5000 m2/g BET Surface Area", J. Am. Chem. Soc. 2009, 131, 4184-4185.
Kreno et al., "Metal-Organic Framework Materials as Chemical Sensors", Chem. Rev. (Washington, D.C., U.S.) 2011 pub. Chem. Rev. vol. 112, 2012,1105-1125.
Lee et al., "Metal-organic framework materials as catalysts", Chem. Soc. Rev., 2009, 38, 1450.
Lee et al., "Light-Harvesting Metal-Organic Frameworks (MOFs): Efficient Strut to Strut Energy Transfer in Bodipy and Porphyrin-Based MOFs", J. Am. Chem. Soc., 2011, 133 (40), pp. 15858-15861.
Levesque et al., "Monte Carlo simulations of hydrogen storage in carbon nanotubes" J. Phys.: Condens. Matter. 2002, 14, 9285.
Li, Qiaowei et al., "Docking in Metal_Organic Frameworks", Science, vol. 325, pp. 855-859 (2009).
Li et al, "Establishing Microporosity in Open Metal-Organic Frameworks: Gas Sorption Isotherms for Zn(BDC) (BDC=1,4-Benzenedicarboxylate)", J. Am. Chem. Soc., 1998, vol. 120, 8571-8572.
Li et al., "Selective gas adsorption and separation in metal-organic frameworks", Chem. Soc. Rev., 2009, 38,1477.
Li et al., "Design and synthesis of an exceptionally stable and highly porous metal-organic framework", Nature 1999, 402, 276-279.
Lin et al., High Capacity Hydrogen Adsorption in Cu(II) Tretracarboxylate Framework Materials: The Role of Pore Size, Ligand Functionalization and Exposed metal Sites, J. Am. Chem. Soc. 2009, 131, 2159-2171.
Liu et al., "Experimental and Theoretical Studies of Gas Adsorption in $Cu_3(BTC)_2$: An Effective Activation Procedure", J. Phys. Chem. C 2007, 111, 9305.
Liu et al., "Progress in adsorption-based CO2 capture by metal—organic frameworks", Chem. Soc. Rev. 2012, 41, 2308-2322.
Ma et al., "Enantioselective catalysis with homochiral metal—organic frameworks", Chem. Soc. Rev., 2009, 38, 1248-1256.
Murray et al., "Hydrogen storage in metal-organic frameworks", Chem. Soc. Rev., 2009, 38, 1294.
Nelson et al., "Supercritical Processing as a Route to High Internal Surface Areas and Permanent Microporosity in Metal-Organic Framework Materials," J. Am. Chem. Soc., 2009, 131, 458-460.
Nouar et al.. "Supermolecular building blocks (SBBs) for the design and synthesis of highly porous metal-organic frameworks," J. Am. Chem. Soc. 2008, 130, 1833.

(56) References Cited

OTHER PUBLICATIONS

Nouar, F., "Design, synthesis and post-synthetic modifications of functional metal-organic materials", dissertation, Univ. of South Florida(2010).

O'Keeffe et al., "The Reticular Chemistry Structure Resource (RCSR) Database of, and Symbols for, Crystal Nets", Acc. Chem. Res. 2008, 41, 1782.

Park et al., "A Highly Porous Metal—Organic Framework: Structural Transformations of a Guest-Free MOF Depending on Activation Method and Temperature", Chem. Eur. J. 2011, 17, 7251-7260.

Potoff et al., "Vapor—liquid equilibria of mixtures containing alkanes, carbon dioxide, and nitrogen", AIChE J. 2001, 47, 1676.

Rappe et al., "UFF, a Full Periodic Table Force Field for Molecular Mechanics and Molecular Dynamics Simulations", J. Am. Chem. Soc. 1992, 114, 10024.

Rocca et al., "Nanoscale Metal—Organic Frameworks for Biomedical Imaging and Drug Delivery", Acc. Chem. Res. 2011, 44, 957-968.

Schnobrich et al., "A Framework for Predicting Surface Areas in Microporous Coordination Polymers", Langmuir 2010, 26, 5808-5814.

Sculley, et al. "The current status of hydrogen storage in metal-organic frameworks-updated" Energy Environ. Sci. 2011, 4 (8), 2721-2735.

Snurr et al., Prospects of Nanoporous Metal-Organic Materials in Advanced Separations Processes, AIChE Journal (2004) 50, pp. 1090-1095.

Suh et al. "Hydrogen Storage in Metal-Organic Frameworks", Chem. Rev. (Washington, D.C., U.S.) 2011; pub. Chem Rev 2012, 112, 782-835.

Sumida et al., "Synthesis and Hydrogen Storage Properties of $Be_{12}(OH)_{12}(1,3,5\text{-benzenetribenzoate})_4$", J. Am. Chem. Soc. 2009, 131, 15120.

Valente et al., "Metal-organic frameworks with designed chiral recognition sites", Chem. Commun. 2010, 46, 4911-4913.

Wang et al., "Tuning Hydrogen Sorption Properties of Metal-Organic Frameworks by Postsynthetic Covalent Modification", Chem. Eur. J. 2010, 16, 212-217.

Wilmer et al., "Large-scale screening of hypothetical metal-organic frameworks", Nature Chem. 2012, 4, 83-89.

Wilmer et al., "Towards rapid computational screening of metal-organic frameworks for carbon dioxide capture: Calculation of framework charges via charge equilibriation", Chem. Eng. J. (Lausanne) 2011, vol. 171, pp. 775-781.

Yan et al. "Exceptionally high $H_2$ storage by a metal-organic polyhedral framework", Chem. Commun. 2009, 1025-1027.

Yan et al. "Metal-Organic Polyhedral Frameworks: High $H_2$ Adsorption Capacities and Neutron Powder Diffraction Studies", J. Am. Chem. Soc., 2010, 132 (12), pp. 4092-4094.

Yan et al., "A mesoporous metal-organic framework constructed from a nanosized $C_3$-symmetric linker and $[Cu_{24}(\text{isophthalate})_{24}]$ cuboctahedra", Chem. Commun. 2011, 47, 9995-9997.

Yuan et al., "An Isoreticular Series of Metal-Organic Frameworks with Dendritic Hexacarboxylate Ligands and Exceptionally High Gas-Uptake Capacity", Angew. Chem., Int. Ed. 2010, 49, 5357-5361.

Yuan et al., "Pressure-Responsive Curvature Change of a "Rigid" Geodesic Ligand in a (3,24)-Connected Mesoporous Metal_Organic Framework", Inorg. Chem. 2011, 50, 10528-10530.

Zhao et al., "Stabilization of Metal-Organic Frameworks with High Surface Areas by the Incorporation of Mesocavities with Microwindows", J. Am. Chem. Soc. 2009, 131, 9186-9188.

Zheng et al., "Enhanced CO2 Binding Affinity of a High-Uptake rht-Type Metal-Organic Framework Decorated with Acylamide Groups", J. Am. Chem. Soc. vol. 133 pp. 748-751 (2011).

International Search Report received in connection with international application No. PCT/US2013/046254, Oct. 22, 2013.

International Preliminary Report on Patentability received in connection with international application No. PCT/US2013/046254, Oct. 22, 2013.

\* cited by examiner

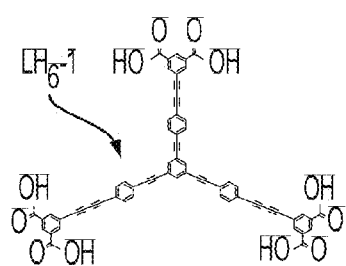
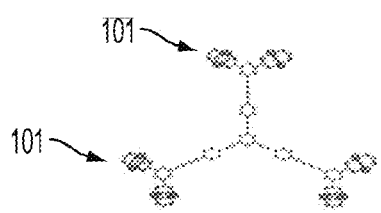
FIG. 1a    FIG. 1b
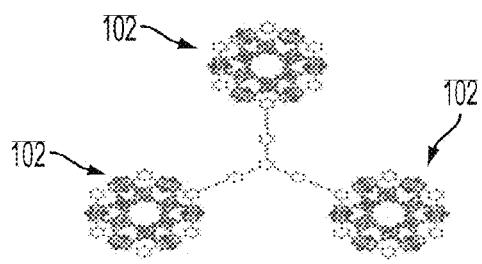
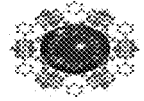
FIG. 1c    FIG. 1d
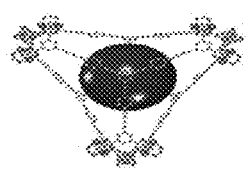
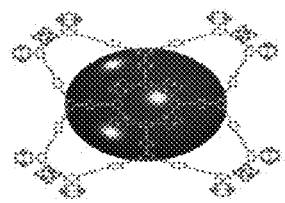
FIG. 1e    FIG. 1f
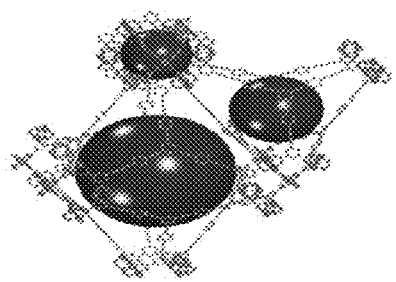
FIG. 1g

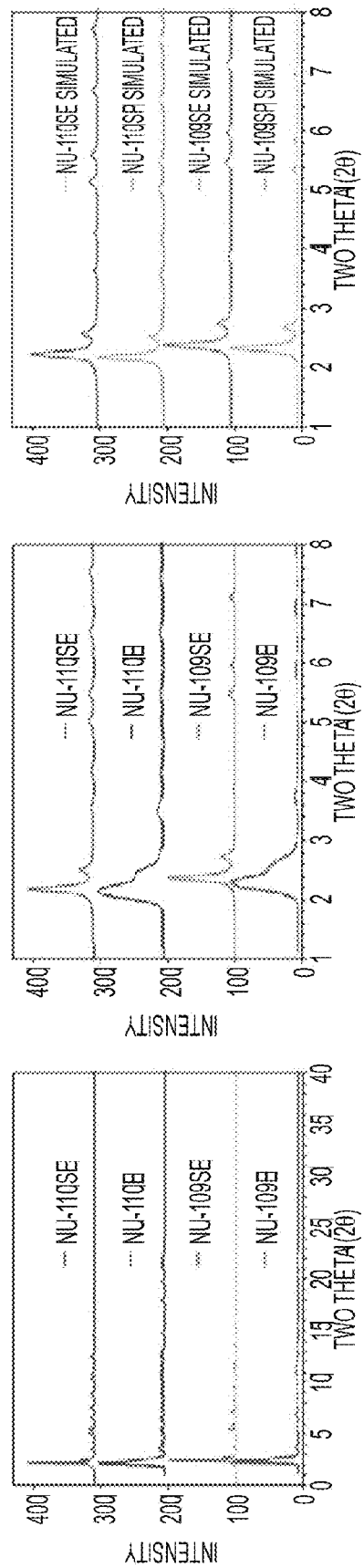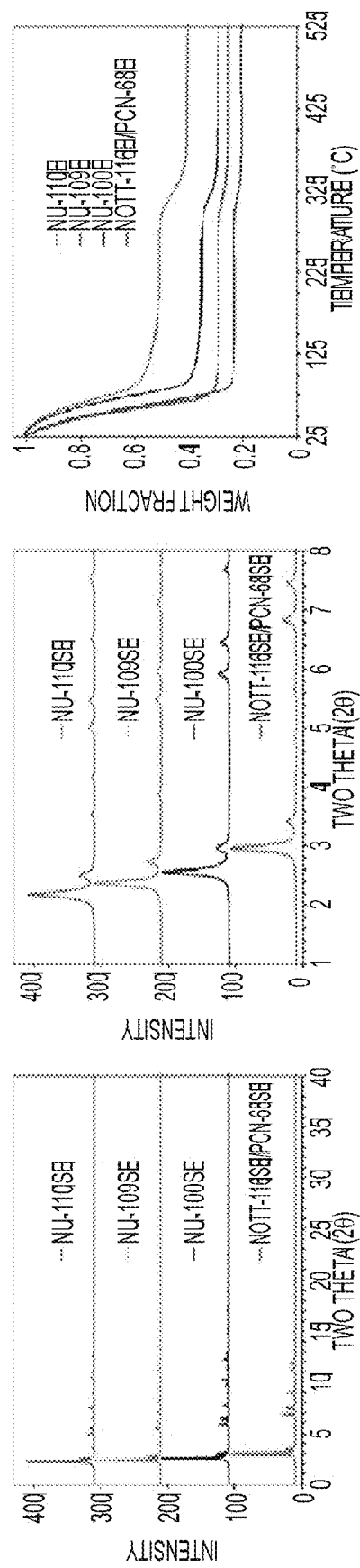

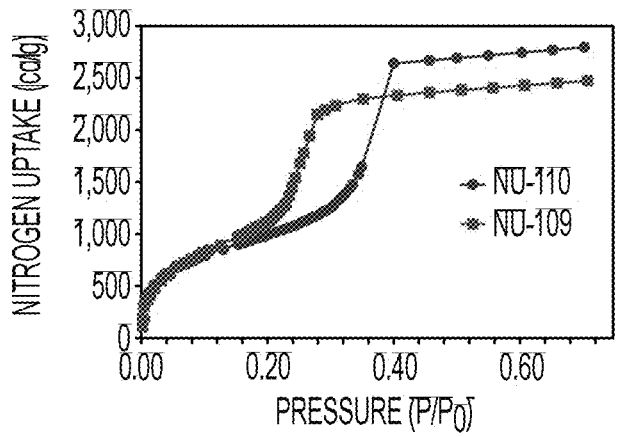
FIG. 3
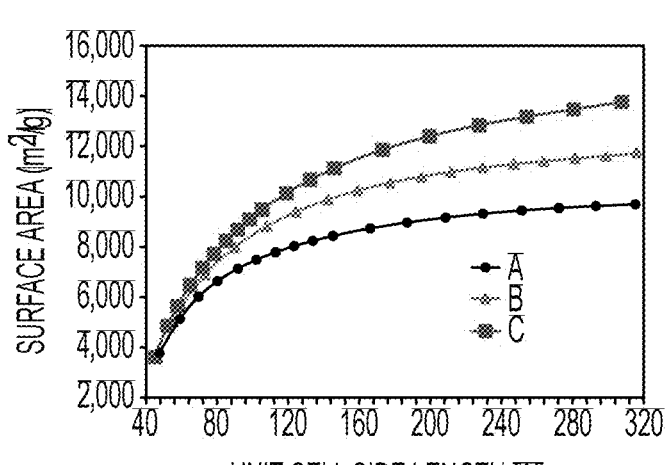 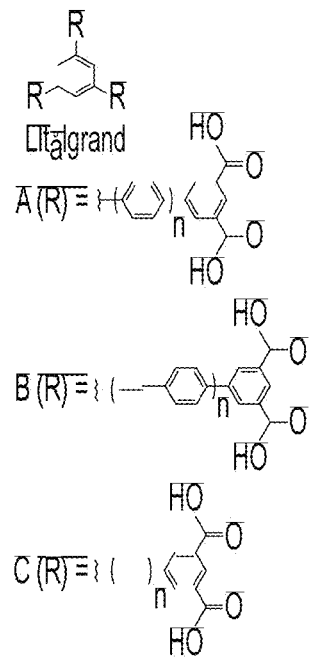
FIG. 4

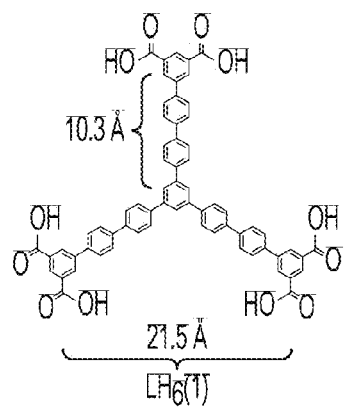
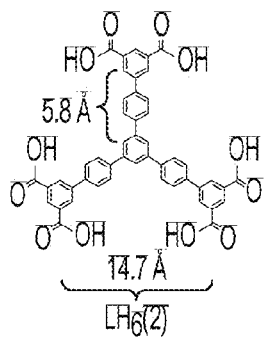
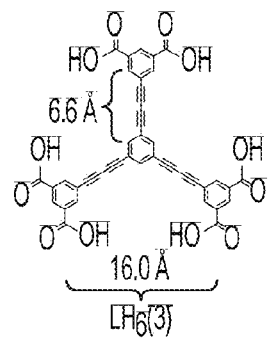
FIG. 5A  FIG. 5B  FIG. 5C
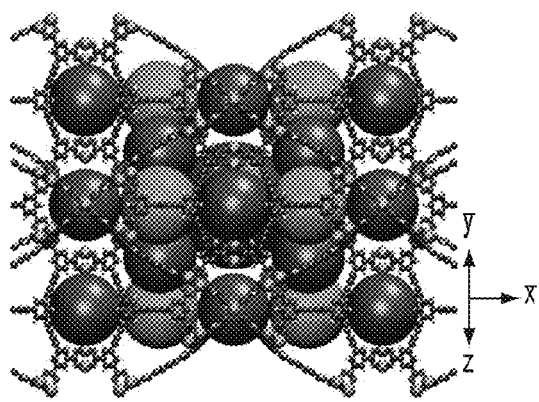
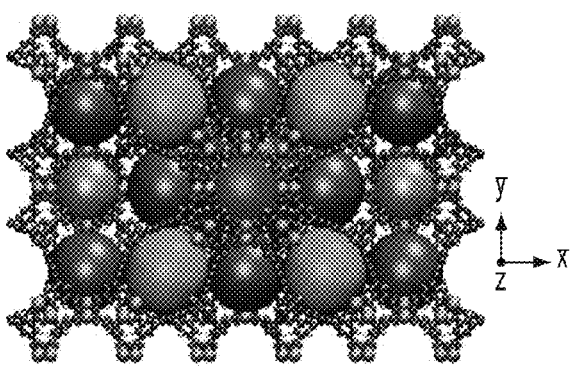
FIG. 6A  FIG. 6B
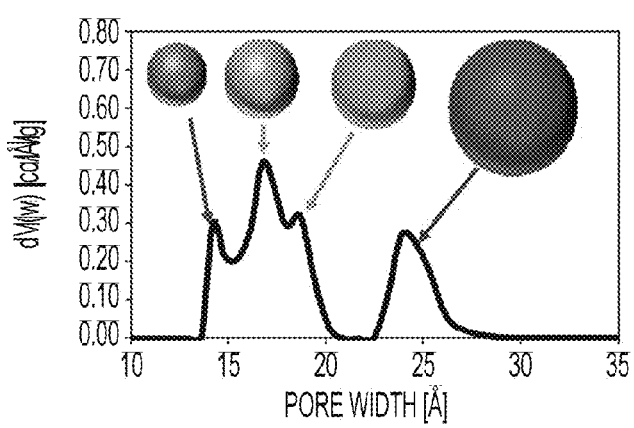
FIG. 6C

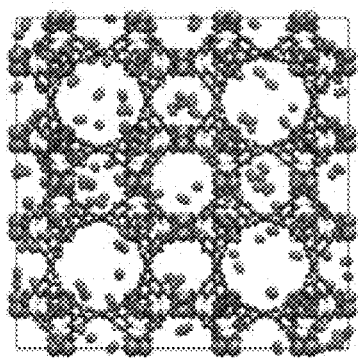
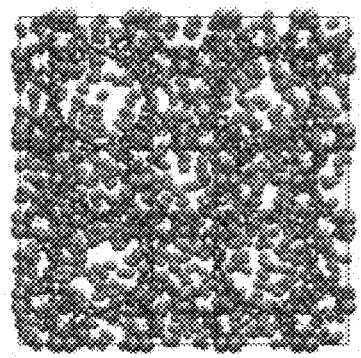
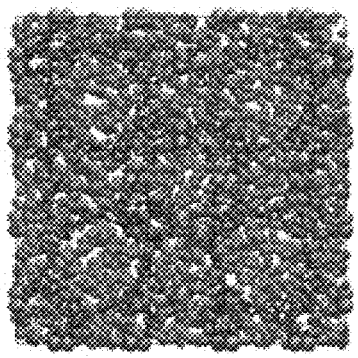
Fig. 39A  Fig. 39B  Fig. 39C
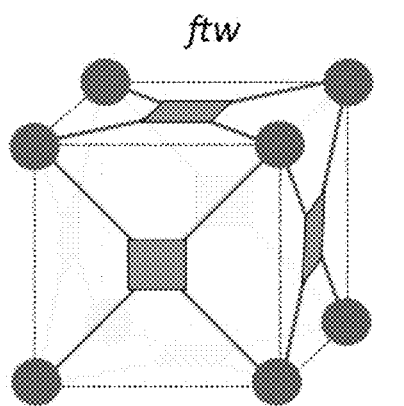
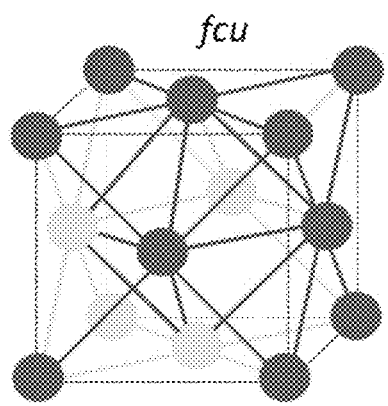
Fig. 40A  Fig. 40B

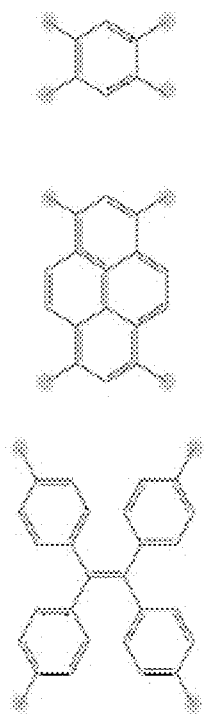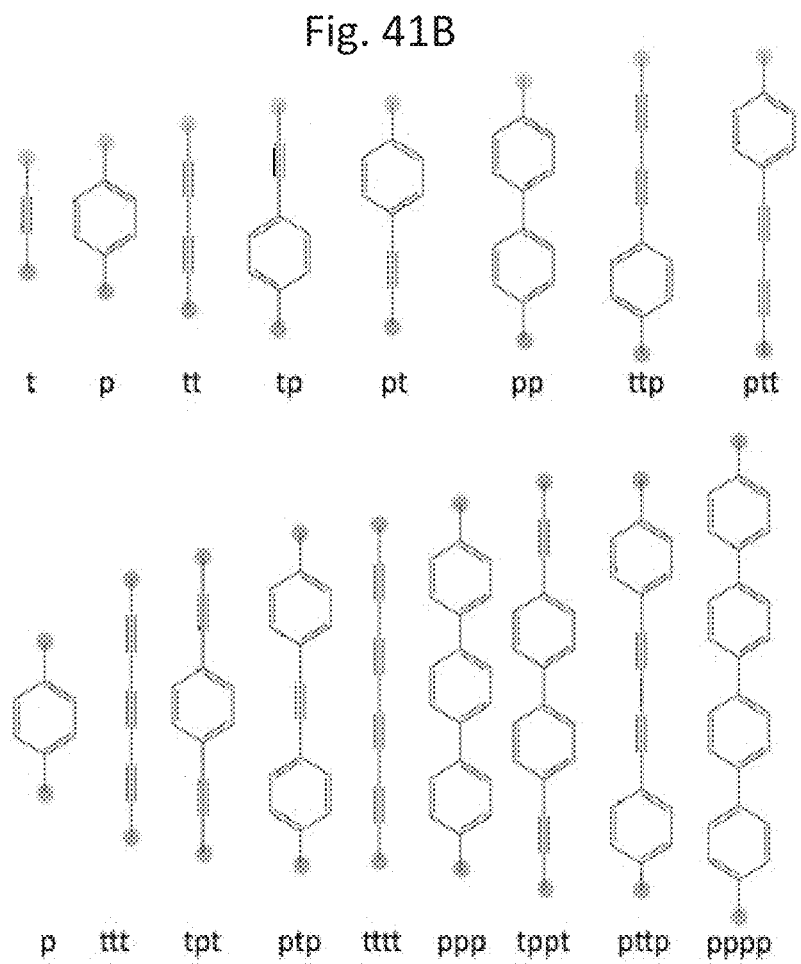
Fig. 41A
Fig. 41B
Fig. 41C

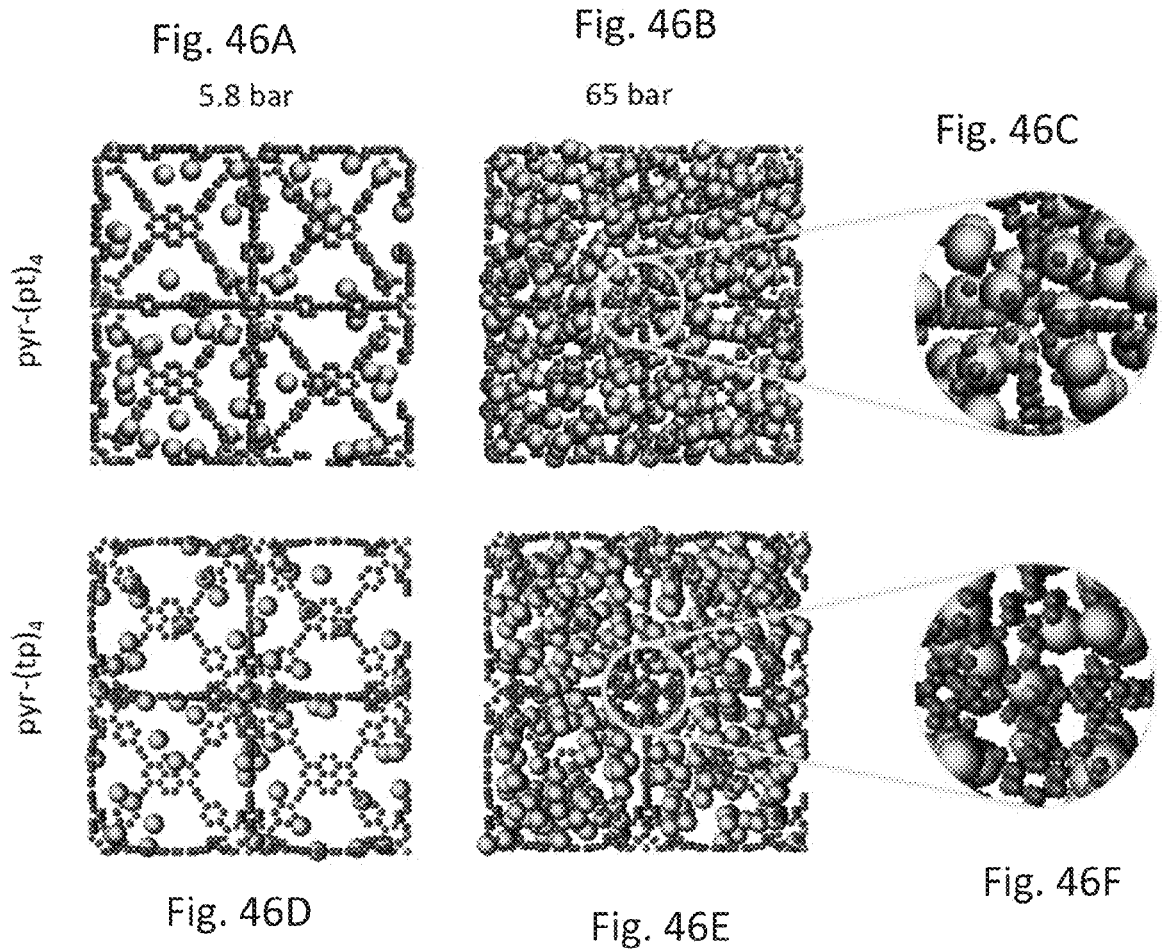

METAL-ORGANIC FRAMEWORK MATERIALS WITH ULTRAHIGH SURFACE AREAS

This application claims the benefit of U.S. Provisional Application No. 61/661,194, filed Jun. 18, 2012, the contents of which are hereby incorporated by reference.

This invention was made with government support under contract number DE-FG02-08ER15967 awarded by the Department of Energy. The government has certain rights in the invention.

BACKGROUND OF THE INVENTION

Extensive research over the past few years has been focused on the synthesis and characterization of microporous materials with high internal surface areas. Metal-Organic Frameworks (MOFs), a crystalline subset of these materials, have shown promise in a wide range of applications from gas storage, chemical separations, chemical sensing, and catalysis, to ion exchange, light harvesting, and drug delivery. High internal surface area is one of the foremost attributes of MOFs and has been shown to be highly desirable in many potential applications involving catalysis or storage. Also relevant is the sorption-based storage of technologically important gases at temperatures above their respective critical temperatures. For example, at T>191 K methane cannot form methane/methane multi-layers. Thermodynamically excess adsorption under these conditions, therefore, can be achieved only via direct contact between individual methane molecules and the sorbent surface.

Additionally fueling interest in MOFs is their extraordinary compositional and structural variety (e.g., ca. 10,000 experimentally known MOFs versus fewer than 300 zeolites) and the fact that many display permanent porosity, ultra-low densities, and well-defined pores and channels. Further, the crystallinity of MOFs allows for their unambiguous structural characterization by X-ray diffraction, greatly simplifying efforts to use computational modeling to predict or explain their unusual or unique physical properties.

One of the first breakthroughs in obtaining MOFs with permanent microporosity came in 1998 from Li et al., who described a material having a Langmuir surface area of 310 $m^2/g$. Increases in reported surface areas for MOFs followed for the next several years, with values reaching 3,800 $m^2/g$ in 2005 and 5,200 $m^2/g$ in 2009. Among the reported high-area materials are MOF-5 (especially in anhydrous form), MOF-177, MIL-101, UMCM-1, and UMCM-2 (See Table 1 discussed in more detail below).

Efforts to achieve even higher surface areas stalled, not primarily because of difficulty in synthesizing new candidate materials, but because of the progressively greater tendency of these materials to collapse upon removal of solvent. However, a MOF activation method based on super-critical carbon dioxide (discussed in more detail below) has enabled difficult-to-activate, large-cavity MOFs to be evacuated without framework collapse or channel blockage. Based on this method, two MOFs with experimentally accessible BET surface areas slightly above 6,000 $m^2/g$ have been reported: MOF-210 and NU-100 (NU-100 is also known as PCN-610).

Some researchers believe that the reported record-high surface areas for NU-100 and MOF-210 are close to the ultimate [experimental] limit for solid materials. This belief stems from: a) simulations showing that the upper theoretical limit for MOF surface areas is about 10,500 $cm^2/g$ when linkers are constructed from repeating phenyl groups, and b) anticipated practical problems, such as poor solubility, low synthetic yields, and cumbersome purification protocols, for candidate linkers featuring very large numbers of phenyl repeat units.

Attempts have also been made previously to calculate the highest possible surface area for a porous material. Chae at al. describe a useful conceptual basis for a strategy to achieve high-surface-area ordered materials. By progressively excising smaller fragments from an infinite graphene sheet and calculating Connolly surface areas of the remaining framework, it is found that exposing all latent edges to give isolated six-membered rings would yield a surface area of 7,745 $m^2/g$. The exposed six-membered rings are essentially benzene molecules without hydrogens, whose inclusion would have given an even higher surface area. By putting this strategy into practice, MOF-177 is synthesized from $Zn_4O$ clusters and 1,3,5-benzenetribenzoate (BTB) organic linkers, which shows a record-breaking surface area for that time (4,750 $cm^2/g$). Subsequently, it was realized that for sorption applications, molecule-accessible surface areas are physically more meaningful than Connolly surface areas. Additionally, Snurr and co-workers showed that, subject to well defined "consistency criteria", experimental BET surface areas for fully evacuated MOFs (but not Langmuir or Connolly surface areas) correspond closely to molecule-accessible surface areas.

In a related approach, Schnobrich et al. constructed a series of structures (in silico) by incrementally adding benzenes to the linker of MOF-5 (1,4-terephthalic acid). This study revealed that a MOF-5 analogue with an infinite number of benzenes in its linker would give an $N_2$-accessible surface area of 10,436 $m^2/g$, which is very close to the maximum attainable surface area (10,577 $m^2/g$) for structures derived from benzene rings regardless of their topology. These studies have, until now, largely defined surface-area targets for MOF materials for both experimental and theoretical investigations, and the use of benzene chains of different forms and lengths has become a common way of synthesizing materials with high surface areas.

SUMMARY

Embodiments include metal-organic frameworks (MOFs) with an ultra-high surface area. By "ultra-high surface area" is meant a Brunauer-Emmett-Teller (BET) surface area of 4,900 $m^2/g$ or greater. The embodiment MOFs as described herein preferably contain one or more acetylene moieties (i.e., carbon triple bonds, which are referred to herein as alkyne or ethynyl bonds).

An embodiment includes a metal organic framework (MOF) material including a Brunauer-Emmett-Teller (BET) surface area greater than 7,010 $m^2/g$.

Another embodiment includes a metal organic framework (MOF) material including hexa-carboxylated linkers including alkyne bonds.

Another embodiment includes a metal organic framework (MOF) material including three types of cuboctahedron cages fused to provide continuous channels.

Another embodiment includes a metal organic framework (MOF) material including a plurality of linkers selected from formula I, II or III:

Formula I
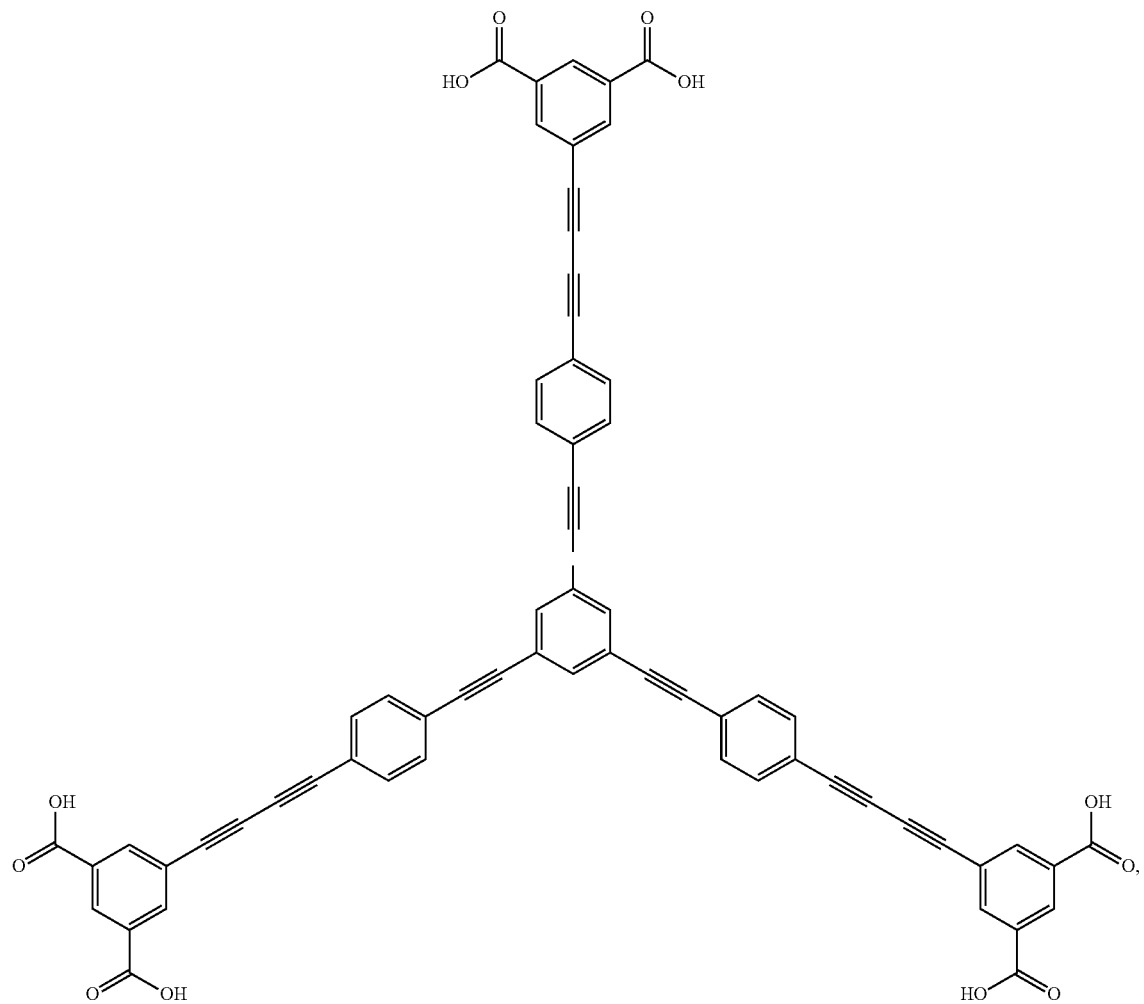
Formula II
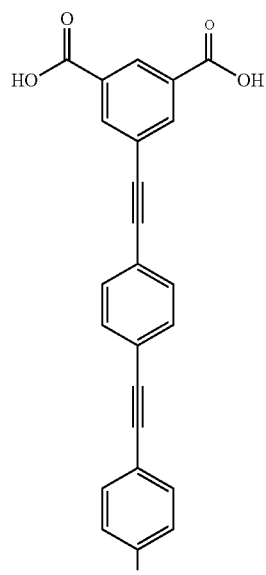

-continued

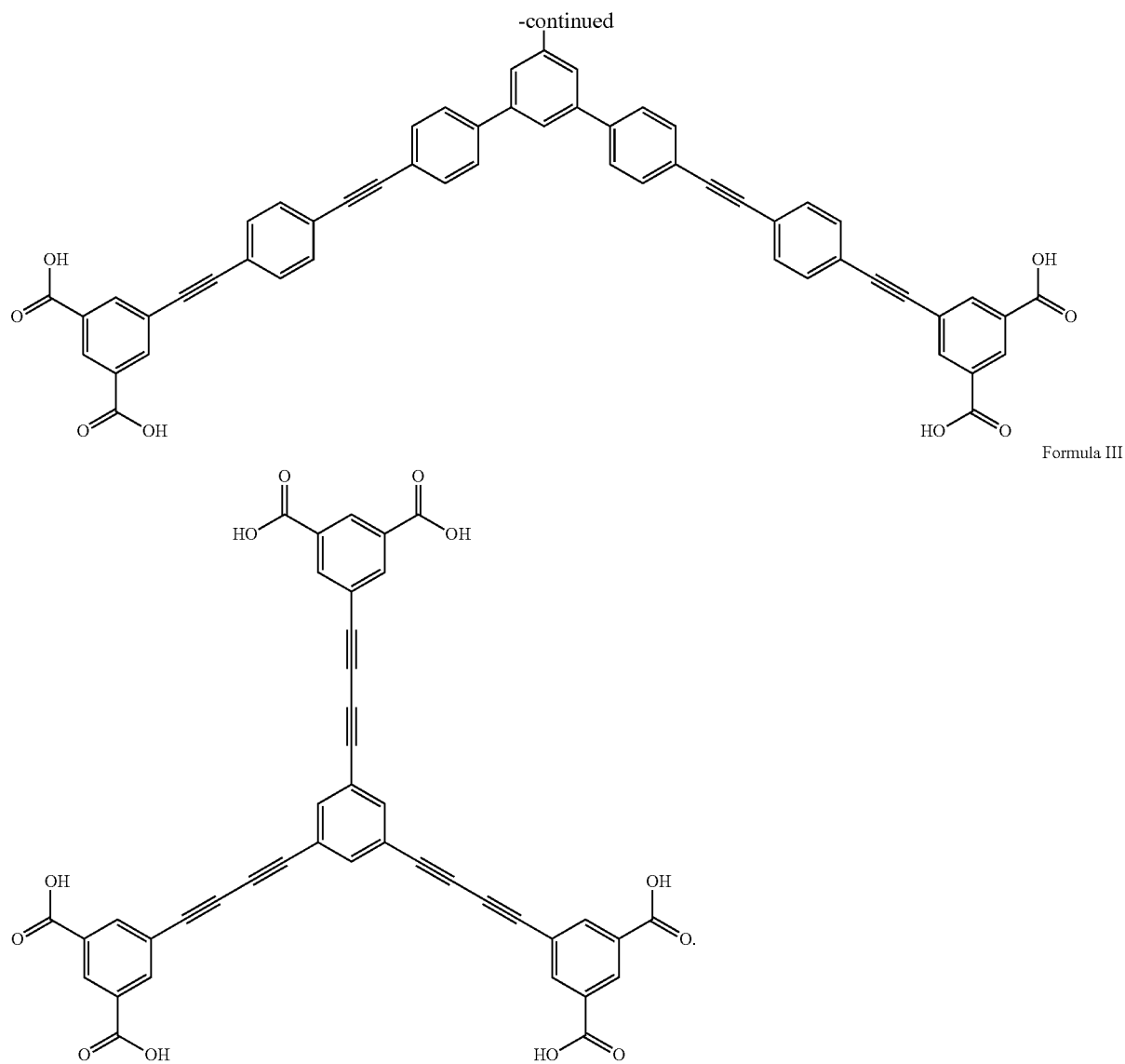

Formula III

Another embodiment includes a method of making a metal organic framework (MOF) material including saponifying hexaester precursors having alkyne bonds to form a plurality of hexa-carboxylated linkers including alkyne bonds and performing a solvothermal reaction with the plurality of hexa-carboxylated linkers and one or more metal containing compounds to form the MOF material.

Another embodiment includes a MOF material wherein the MOF comprises linkers terminated with ethynyl carboxylate groups.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1a-1g are schematic diagrams illustrating structural features of a MOF (compound A) according to an embodiment.

FIGS. 2a-2c are powder x-ray diffraction (PXRD) patterns of compound A (NU-109) and compound B (NU-110) of the embodiments of the invention. In these figures, SP means Simulated of Predicted structure, SE means Simulated of Experimental structure, and E means Experimental results.

FIGS. 2d and 2e are PXRD patterns of compounds A and B and of a prior art compounds NU-100 (described in Farha, O. K., et. al., *Nature Chem.* 2010, 2, 944, which is incorporated herein by reference in its entirety) and NOTT-116/PCN-68 (described in Yan, Y., et. al., *J. Am. Chem. Soc.* 2010, 132, 4092 and Yuan, D., et. al., *Angew. Chem., Int. Ed.* 2010, 49, 5357).

FIG. 2f illustrates TGA profiles of compounds A and B of the embodiments of the invention and of the prior art NU-100 and NOTT-116/PCN-68 compounds.

FIG. 3 is a plot of sorption (e.g., nitrogen uptake versus pressure) for compounds A and B of the embodiments.

FIG. 4 is a plot of the estimated accessible surface areas versus unit cell length of MOFs with rht-topology constructed with LH$_6$ ligands consisting of linkers A, B and C, where the center benzene of the ligand was extended by addition of increasing number (n) of phenyl, phenylethynyl, and ethynyl moieties, respectively.

FIGS. 5a-5c are chemical formulas illustrating hexacarboxylic acid linkers of an embodiment (compound C shown in FIG. 5c) and two comparative examples (prior art MOFs NOTT-119 and NOTT-112 shown in FIGS. 5a and 5b, respectively).

FIGS. 6A and 6B are structurally derived view of a MOF according to an embodiment and FIG. 6C is a plot of the pore size distribution in the MOF (where the dark color spheres correspond to the pores).

FIGS. 39A-39C are spacing filling models illustrating H$_2$ storage in NU-111 from GCMC simulations at 77K at: a) 1 bar, b) 10 bar, and c) 100 bar.

FIGS. 40A-40B are schematic illustrations of MOFs with A) a ftw topology and B) a fcu topology.

FIGS. 41A-41C illustrate chemical formulas for building linkers including: A) center molecules for tetracarboxylic acid (TCA) linkers, B) peripheral building blocks to extend the TCA linkers and C) dicarboxylic acid (TCA) linkers.

FIGS. 46A-46C are simulated snapshots of methane adsorption at 5.8 bar and 65 bar for ftw MOFs using the TCA linker pyr(pt)$_4$.

FIGS. 46D-46F are simulated snapshots of methane adsorption at 5.8 bar and 65 bar for ftw MOFs using the TCA linker pyr-(tp)$_4$.

DETAILED DESCRIPTION OF THE EMBODIMENTS OF THE INVENTION

Figure 1H:
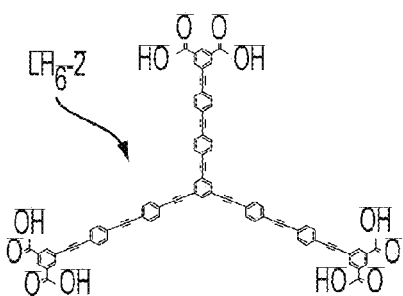
FIGS. 1h-1n are schematic diagrams illustrating structural features of a MOF (compound B) according to another embodiment.

Embodiment MOFs are described below that display the highest experimental Brunauer-Emmett-Teller (BET) surface areas to date (~7,000 m$^2$/g). Additionally, a new surface area ceiling for MOFs (~14,600 m$^2$/g) that substantially exceeds what much of the MOF community perceives to be a theoretical upper limit (~10,500 m²/g) is computationally demonstrated. By moving beyond phenyl-only struts to more "area-efficient" building blocks for MOF linkers, both the experimental maximum and the perceived theoretical ceiling are increased.

Embodiments include MOFs with an ultra-high surface area employing (3,24)-paddlewheel connected MOF networks (rht-topology). A feature of the rht-topology is that catenation (interpenetration or interweaving of multiple frameworks) is mathematically precluded. Using this topology, three new materials with ultra-high surface areas, compound A (shown in FIG. 1g), compound B (shown in FIG. 1n) and compound C (shown in FIGS. 5ba and 5c), from three new hexa-carboxylated linkers, are provided. Compound A and Compound B correspond to Northwestern University MOFs NU-109 and NU-110, respectively, which are described in O. K. Farha, et al., *J. Am. Chem. Soc.*, 2012, 134 (36), pp 15016-15021 "Metal-organic Framework Materials with Ultrahigh Surface Areas: Is the Sky the Limit?" (which is incorporated herein by reference in its entirety and was published after the effective priority date of the present application). Compound C corresponds to Northwestern University MOF NU-111 described in O. K. Farha, et. al., *J. Am. Chem. Soc.*, 2012, 134 (24), pp 9860-9863 "Designing Higher Surface Area Metal-Organic Frameworks: Are Triple Bonds Better Than Phenyls?" (which is incorporated herein by reference in its entirety and was published after the effective priority date of the present application).

The synthesis and description of the hexa-carboxylic-acid forms of the linkers ($LH_6$-1, $LH_6$-2 and $LH_6$-3 FIGS. 1a, 1h, 5 and 9) are described in detail below. Briefly, $LH_6$-n species are obtained via saponification of the corresponding hexaester precursors, which, in turn, are obtained via Sonagashira coupling of 1,3,5-triiodobenzene with the appropriate acetylene-terminated compounds. The BET surface areas and pore volumes for Compounds A and B and comparative MOFs are presented in Table 1 below.

TABLE 1

| MOF | BET surface area (m² g⁻¹) | Pore volume (cm³ g⁻¹) |
| --- | --- | --- |
| MFU-4l | 2750 | 1.26 |
| NOTT-102 | 2940 | 1.14 |
| PCN-61 | 3000 | 1.36 |
| $Cu_{24}(TPBTM)_8(H_2O)_{24}$ | 3160 | 1.27 |
| SNU-77 | 3670 | 1.52 |
| NOTT-112 | 3800 | 1.62 |
| MOF-5 | 3800 | 1.55 |
| UMCM-1-$NH_2$ | 3920 | — |
| PCN-66 | 4000 | 1.36 |
| $Be_{12}(OH)_{12}(BTB)_{24}$ | 4030 | — |
| UMCM-1 | 4160 | — |
| MIL-101c | 4230 | 2.15 |
| Bio-MOF-100 | 4300 | 4.30 |
| MOF-205 | 4460 | 2.16 |
| MOF-177 | 4750 | 1.59 |
| DUT-23-Co | 4850 | 2.03 |
| NOTT-116/PCN-68 | 4660/5110 | 2.17 |
| UMCM-2 | 5200 | 2.32 |
| NU-100 | 6140 | 2.82 |
| MOF-210 | 6240 | 3.6 |
| Compound A | 7010 ± 80 | 3.75 |
| Compound B | 7140 | 4.40 |

Solvothermal reactions of $LH_6$-1 or $LH_6$-2 and $Cu(NO_3)_2 \cdot 2.5H_2O$ in DMF/EtOH/HCl (DMF=dimethylformamide) at 75° C. results in MOFs having a framework formula $[Cu_3(L^{6-}_{(A)})(H_2O)_3]_n$, (compound A-E, where E=Experimental and $L^{6-}_{(A)}$=the hexa-anion of $LH_6$-1) or $[Cu_3(L^{6-}_{(B)})(H_2O)_3]_n$ (compound B-E, where $L^{6-}_{(B)}$=the hexa-anion of $LH_6$-2) after 48 hours. As illustrated in FIGS. 1b and 1i, X-ray analysis of single crystals of compound A-E and compound B-E reveals non-catenated structures in which the framework nodes include $Cu^{II}_2$ units coordinated by the carboxylates of $L^{6-}$ in a paddlewheel configuration. Thus, each of the three arms of the $L^{6-}$ linker includes two $Cu^{II}_2$ paddlewheel units 101 for a total of six paddlewheel units 101 per $L^6$ linker. The axial sites of the $Cu^{II}_2$ units are coordinated by water molecules that are not well resolved in the X-ray analysis.

The experimental structures of compound A-E and compound B-E are found to be in excellent agreement with the predicted structures, compound A-SP(SP=Simulation of the Predicted structure) and compound B-SP. The predicted and experimental structures of both materials have a cubic space group, Fm3̄m, with unit-cell dimensions of a=b=c=65.899 Å (compound A-SP at 0 K), 64.528 Å (compound A-E at 100 K), 70.330 Å (compound B-SP at 0 K), and 68.706 Å (compound B-E at 297 K). The differences in the unit cells between the experimental and simulated structures are only 1.37 Å and 1.62 Å for compound A and compound B, respectively. The experimental structures are solved, in part, by utilizing the coordinates of the in silico structures predicted by using molecular modeling techniques.

In an embodiment, solvothermal reactions of $LH_6$-3 and $Cu(NO_3)_2 \cdot 2.5H_2O$ in DMF/EtOH/HCl (DMF=dimethylformamide) at 80° C. results in MOFs (e.g., compound C) with the framework formula $[Cu_3(L^{6-})(H_2O)_3]_n$ after 48 hours in 75% yield (compound C-E at 297 K). X-ray analysis of single crystals of compound C reveals a non-catenated structure with a cubic space group, Fm3̄m, in which the framework nodes consist of $Cu^{II}_2$ units coordinated by the carboxylates of $L^{6-}$ in a paddlewheel configuration (FIGS. 1(a) and 1(B)). The axial sites of the $Cu^{II}_2$ units are coordinated by water molecules that are well resolved in the X-ray analysis. The experimental structure has unit-cell dimensions of a=b=c=48.9 Å at 225 K.

Compound A and compound B share several topological features. Briefly, each $L^{6-}$ unit contributes to the formation of three cuboctahedron building blocks 102 (FIGS. 1c and 1j). Both MOF compounds A and B contain three types of cages (FIGS. 1g and 1n) that are fused such as to provide continuous channels. Cuboctahedral cage 1 (FIGS. 1d and 1k) is formed from 24 isophthalate groups from $L^{6-}$ units and 12 pairs of metal ions, such as copper ions, (i.e., 24 total metal ions). Metal ions that may be used include, but are not limited to, $Li^+$, $Na^+$, $Rb^+$, $Mg^{2+}$, $Ca^{2+}$, $Sr^{2+}$, $Ba^{2-}$, $Sc^{2+}$, $Ti^{4+}$, $Zr^{4+}$, $Ta^{3+}$, $Cr^{3+}$, $MO^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{3+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$, $Cr^{4+}$ and their combinations. The nodes forming triangular windows in cage 1 are shared with cage 2 (FIGS. 1e and 1i), while those forming rectangular windows are shared with cage 3 (FIGS. 1f and 1m). Cage 2 (FIGS. 1e and 1i) defines a truncated tetrahedron, and is formed from isophthalate groups from four $L^{6-}$ linkers and 12 pairs of metal ions, such as copper ions, (i.e., 24 total metal ions). As expected, cage 3 (FIGS. 1f and 1m) is describable as a truncated cuboctahedron and is formed by 24 $Cu_2^{II}$ paddlewheel nodes and portions of eight distinct $L^{6-}$ units.

Figure 7:
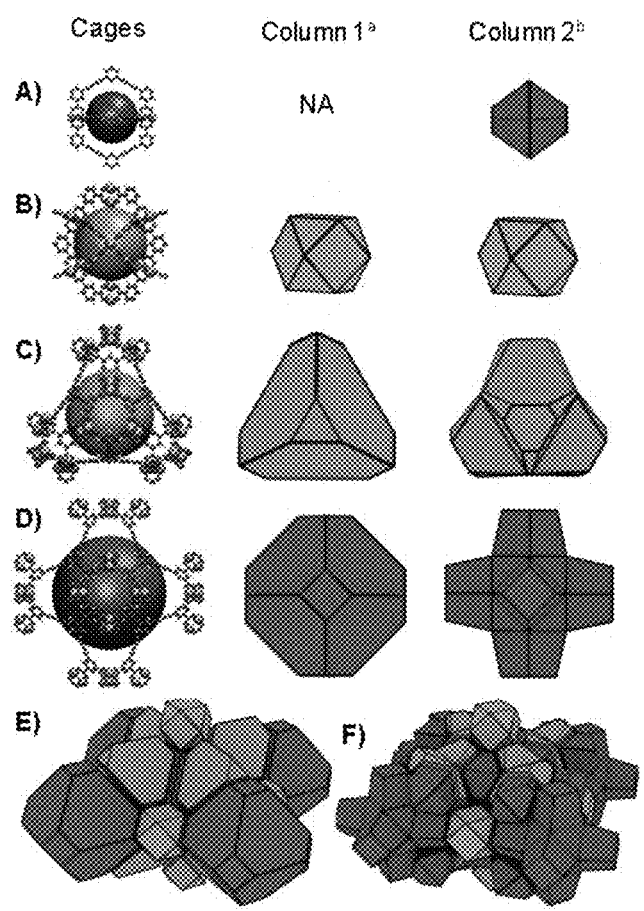
FIGS. 7A-7F are schematic illustrations showing polyhedral shaped cages assuming straight lines between copper paddlewheels and taking into account the curvature of the ligands in a MOF according to an embodiment.

Compound C can be represented by three types of space-filling polyhedra (derived from drawing straight lines between copper paddlewheels), also referred to as cages, that are fused such that they form continuous channels (FIG. 7:

column 1 (B, C, D and E)). The smallest, cuboctahedral cage, is formed from 24 isophthalate groups from $L^{6-}$ ligand units and 12 pairs of metal ion (e.g. copper ions) (FIG. 7b). The second cage is a truncated tetrahedron and is formed from isophthalate groups from four $L^{6-}$ linkers and 12 pairs of metal ions, (e.g. copper ions) (FIG. 7c). The largest cage can be described as a truncated cuboctahedron and is formed by 24 $Cu_2^{II}$ paddlewheel nodes and portions of eight distinct $L^{6-}$ units (FIG. 7d). However, there is no unique representation of a MOF in the form of space-filling polyhedral. Thus, the scheme described above, though both common and useful for rht topologies, neglects a fourth cavity that can be detected experimentally (FIG. 7a). In an alternate scheme of space-filling polyhedral, the MOF formed with compound C may be described as having four experimentally discovered cavities (FIG. 7: column 2 (a, b, c, d and f)). Therefore, there are two ways of describing the topological features of compound C (see FIG. 31 which shows the four polyhedra in compound C obtained by taking into account the curvature of the ligand as a linker between metal nodes, and FIG. 32 which shows the three polyhedra in compound C obtained by connecting the metal nodes). The phase purity of a bulk sample of compound C may be established via powder X-ray diffraction (PXRD) measurement since the simulated PXRD pattern is in excellent agreement with the experimental PXRD pattern (see FIG. 21).

Figure 1I:
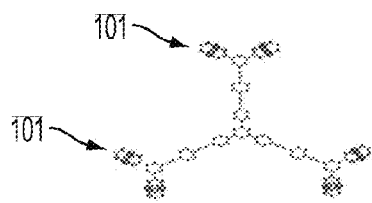
Figure 1J:
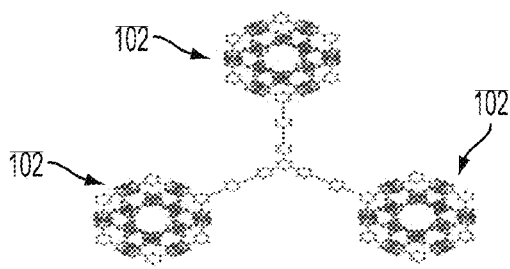
Figure 1K:
Figure 1L:
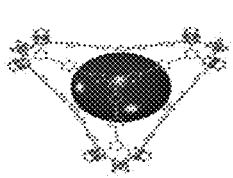
Figure 1M:
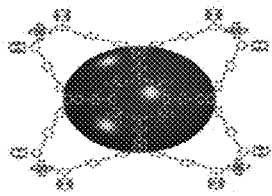
Figure 1N:
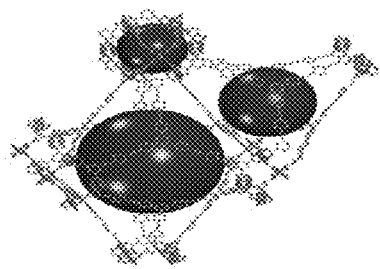

Thus, each linker shown in FIGS. 1a, 1h and 5c has at least 6 alkyne bonds per linker, such as six to nine bonds per linker. Preferably, the linker has a central benzene ring and at least three struts (preferably 3 struts) connected to the central benzene ring. Each strut may terminate in terminal benzene ring and contain two or more alkyne bonds, such as three alkyne bonds in FIG. 1a and two alkyne bonds in FIGS. 1h and 5c. More than three alkyne bonds per strut (e.g., four to six bonds) may be used. In the embodiments of FIGS. 1a and 1h, each strut also contains one or more benzene rings, such as one benzene ring per strut in FIG. 1a and two benzene rings per strut separated by an alkyne bond in FIG. 1h. More than three benzene rings (e.g., 4-6 rings) per strut may be used.

Figure 22:
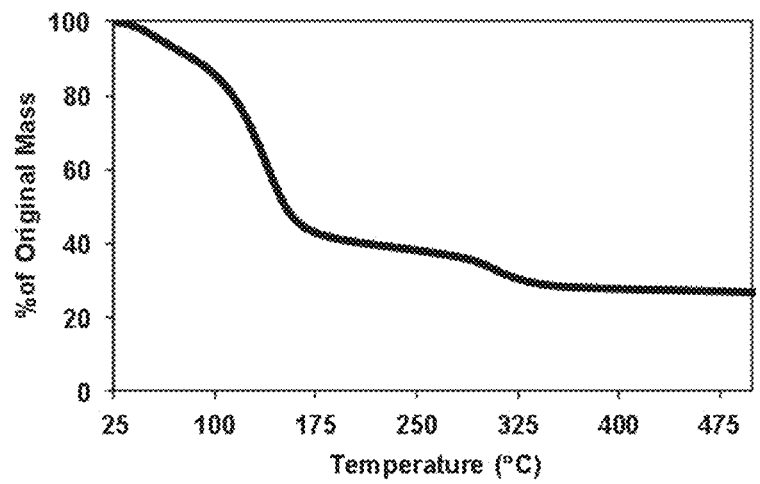
FIG. 22 is a TGA trace of NU-111 according to an embodiment.
Figure 23:
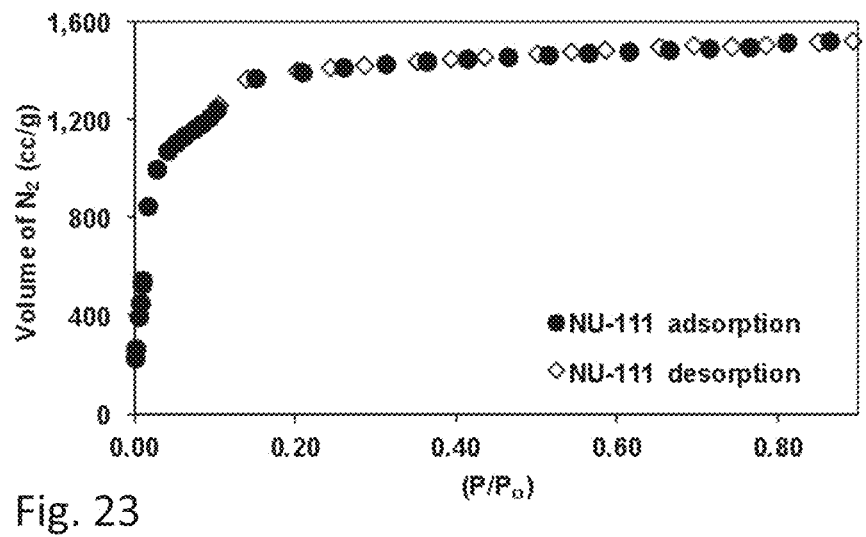
FIG. 23 is a plot of experimental N$_2$ adsorption and desorption isotherms for NU-111 at 77 K according to an embodiment.

The phase purity of bulk samples of compound A and compound B may also be confirmed via powder X-ray diffraction (PXRD) measurements (FIGS. 2a and 2b). Additionally, the simulated PXRD patterns from experimental and predicted structures are in excellent agreement (FIG. 2c). This confirms that, apart from minor differences in unit cell dimensions, the predicted structures are identical to the experimentally obtained materials. The differences are tentatively ascribed to the difference between experimental (i.e., X-ray collection) and simulation temperatures. The PXRD patterns of compound A-SE (SE=Simulated from Experimental structure) and compound B-SE are compared to NU-100SE and NOTT-116/PCN-68, which share the rht-topology. The PXRD patterns (FIGS. 2d and 2e) show the lowest angle peak progressively shifting to smaller 2θ, which corresponds to an increasing unit cell length and therefore a larger distance between the copper nodes, culminating with compound B-SE. Thermogravimetric analysis (TGA) of compound A-E and compound B-E reveals in both cases a mass loss at about 100° C. This loss is assigned to loss of solvent (DMF), with no further mass loss occurring until 325° C. (FIG. 2f). Both MOFs contain more free solvent than either NU-100E/PCN-610 or NOTT-116E/PCN-68E, suggesting the potential for greater permanent porosity. Additionally, thermogravimetric analysis (TGA) of compound C reveals a mass loss at about 135° C., assigned to solvent (DMF), with no further mass loss occurring until about 300° C. (FIG. 22).

Removal of guest solvent molecules from the pores without significantly diminishing porosity is also desirable. Failure to prevent porosity loss may result in significant discrepancies between the surface areas obtained experimentally and those estimated from computational modeling. Since MOFs containing large pores such as compound A and compound B are particularly predisposed to collapse, an unconventional MOF activation strategy recently developed and now used by MOF researchers throughout the world to activate them is employed. The activation takes advantage of supercritical carbon dioxide (SCD) processing. SCD processing may be performed with a Tousimis™ Samdri® PVT-30 critical point dryer or any other suitable equipment. Prior to drying in an embodiment, DMF/EtOH-solvated MOF samples may be soaked in a solvent, such as ethanol, such as 100% ethanol, replacing the soaking solution, for example, every day for 3 days. The ethanol-containing samples may be placed inside the dryer. The ethanol may be exchanged with $CO_2$ (liq.) over a period of 5-24 hours, such as 5-12, such as 10 h. The temperature then may be raised and $CO_2$ vented under supercritical conditions where capillary forces and solvent surface-tension are inherently absent.

The porosities of SCD-activated compound A and compound B may be examined via nitrogen adsorption at 77 K. $N_2$ isotherms show extraordinarily high limiting uptakes of 2480 and 2845 $cm^3/g$ for compound A-E and compound B-E, respectively (FIG. 3). As shown in Table 2, below, the experimental BET surface areas of activated compound A-E and compound B-E are 7010±80 and 7140 $m^2/g$. These are in excellent agreement with the fitted (in silico) BET surface areas for compound A-SE (6950 $m^2/g$) and compound B-SE (7400 $m^2/g$) and with the simulated BET surface area for compound A-SP (7560 $m^2/g$) and compound B-SP (7800 $m^2/g$).

TABLE 2

| MOF | BET surface area ($m^2\ g^{-1}$) | Pore volume ($cm^3\ g^{-1}$) |
|---|---|---|
| NU-109SP | 7560 | 4.12 |
| NU-109SE | 6950 | 3.90 |
| NU-109E | 7010 ± 80 | 3.75 |
| NU-110SP | 7800 | 4.44 |
| NU-110SE | 7400 | 4.18 |
| NU-110E | 7140 | 4.40 |

SP = Simulated of Predicted structure
SE = Simulated of Experimental structure
E = Experimental results Preferably, the BET surface area of the MOF material is greater than 4,900 $cm^3/g$, such as 7,010-14,600 $cm^3/g$, such as 10,500 to 14,600 $cm^3/g$.

The deviation in surface areas between the SE and SP materials reflects the small, but finite, differences in dimensions of the experimental versus calculated unit cells. Nonetheless, these surface areas are the highest for any porous materials reported to date. Moreover, the total pore volumes of compound A-E and compound B-E are 3.75 and 4.40 $cm^3/g$, which are substantially larger than any other high-pore-volume MOFs (see Table 1 above). The pore volume of the MOF materials may be between 3.75 and 4.5 $cm^3/g$, such as 3.75 and 4.4 $cm^3/g$, including 4 to 4.4 $cm^3/g$. Additionally, the observed void volumes of ca. 93% (for each) (e.g., at least 90% such as 90-93%) exceed those for any other solvent-evacuated MOF material described to date.

The nitrogen isotherms shown in FIG. 3 are type-IV rather than type-I. The nitrogen uptake is at least 1000 cc/g for $P/P_o$ of least 0.2, such as 1000-2600 cc/g for $P/P_o$ between 0.2 and 0.4, and greater than 2500 cc/g for $P/P_o$ of 0.4 and above. This reflects the fact that both compound A and compound B contain multiple types (sizes) of pores. The simulated isotherms show three distinct regions, while the experimental data do not resolve these as clearly. However, the simulated and experimental pore size distributions are in excellent agreement. Additionally, PXRD patterns for as-synthesized, activated and resolvated compound A and compound B show no evidence for structural changes during activation and porosity measurements.

Figure 8A:
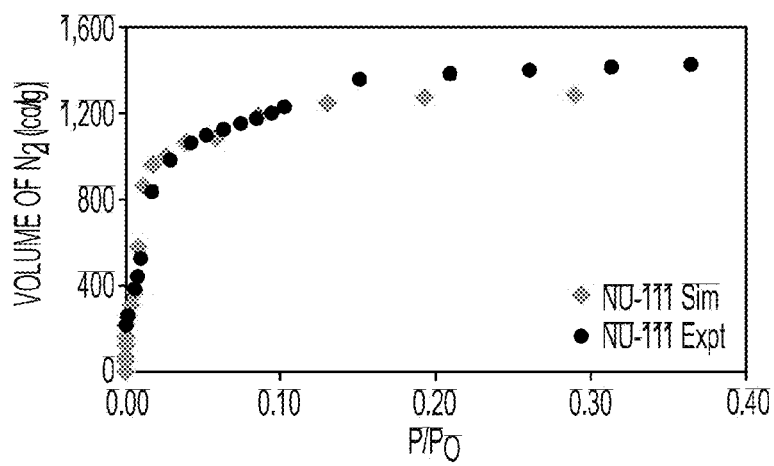
FIGS. 8a-8c are plots illustrating adsorption isotherms of: (a) N$_2$, (b) excess H$_2$ and total (excess and absolute) (c) H$_2$ at 77K according to an embodiment.

With respect to compound C, the experimental and simulated $N_2$ isotherms are in excellent agreement as shown in FIG. 8A. Consistent with simulations, the experimental BET surface area of compound C is found to be 5000±80 $m^2/g$, which is higher than that of PCN-69/NOTT-119 (3989/4118 $m^2/g$). The experimental BET surface area is in excellent agreement with the BET surface area determined from the computationally simulated isotherm (4915 $m^2/g$). The total experimental pore volume of compound C is 2.38 $cm^3/g$. The pore-size distribution of compound C, calculated from Ar adsorption experiments at 87 K using nonlocal density functional theory (NLDFT), shows peaks around 14, 17, 19, and 24 Å (FIG. 1C). This is in excellent agreement with a geometric calculation based on the crystal structure (see FIG. 39).

Figure 8B:
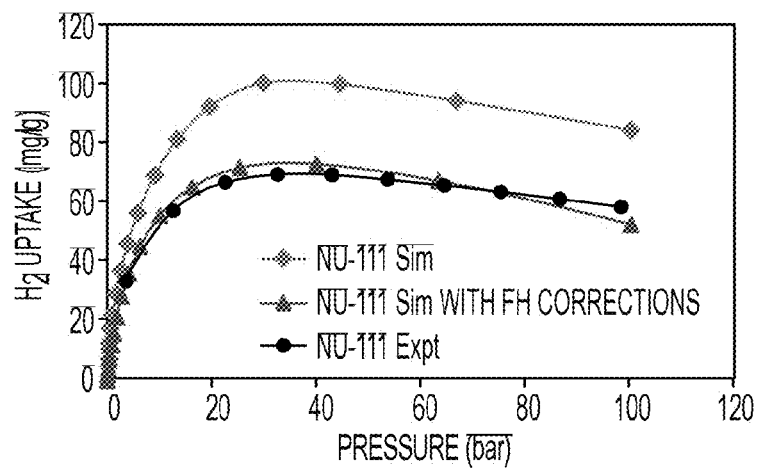
Figure 8C:
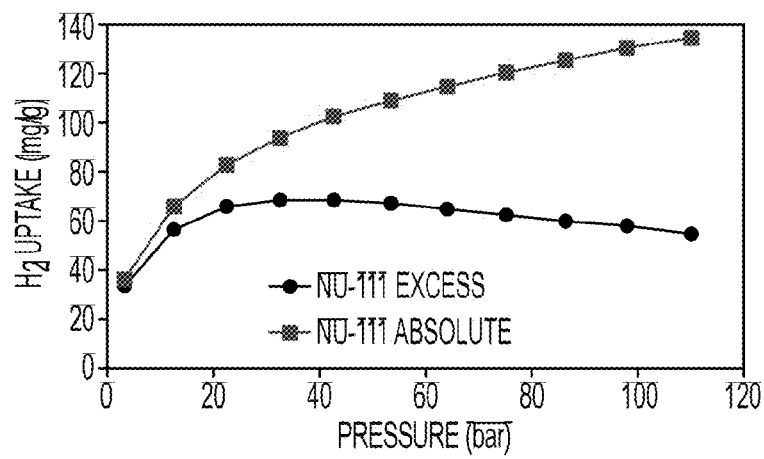

The high-pressure hydrogen capacity of compound C is also measured. These measurements are done at the DOE Hydrogen Sorption Center of Excellence at the National Renewable Energy Laboratory (NREL). Sorption data for $H_2$ are collected up to 110 bar at 77 K. The "excess" gas adsorption is directly accessible experimentally. Excess gas adsorption is the amount of gas adsorbed due to the presence of the adsorbent. The total adsorption is the sum of the excess adsorption and the amount that is found within the pore volume simply due to the finite bulk-phase density of the gas, if the adsorbent is not present. For gas storage and delivery purposes, the total amount adsorbed is the more relevant quantity. As show in FIGS. 8B and 34, the excess hydrogen uptake of compound C is 21 mg/g at 1 bar and 69 mg/g at 32 bar (e.g., 21-69 mg/g at 1-32 bar). By using the $N_2$-derived pore volume (2.38 $cm^3/g$) and the bulk phase density of $H_2$, the total $H_2$ uptake at 110 bar and 77 K is calculated to be 135 mg/g (FIG. 8C). The uptake of compound C is within range of the U.S. Department of Energy's revised long-term systems target for onboard $H_2$ storage, 5.5 wt % (=58 mg/g) (at cryogenic rather than ambient temperature). The simulated $H_2$ isotherm of compound C is in qualitative agreement with the experimental $H_2$ measurements using the classical force field model (FIG. 3B). Incorporating the Feynman-Hibbs corrections for quantum diffraction effects results in excellent agreement with the experimental isotherm.

The stability of compound C may be examined by running multiple cycles of high-pressure hydrogen adsorption at room temperature. It shows no loss of capacity. In addition, the $N_2$ isotherms for compound C is measured before sending the sample to NREL and upon receiving the sample back from NREL. The $N_2$ isotherm shows no loss of porosity during the shipping and measurements.

In another embodiment, a method for attaining MOFs with ultra-high surface areas is provided. The basis of one of these routes relies on further exposing the edges of a six-membered carbon ring by dividing it into three separate but chemically linked pieces, where each includes two carbon atoms linked by a triple bond (i.e., an alkyne bond). These pieces are roughly equivalent to acetylenes, but with carbon-carbon single bonds to neighboring pieces replacing terminal hydrogen atoms. Employing three linked acetylenes in place of a single benzene ring in a material results in a significantly higher molecule-accessible surface area, since larger numbers of exposed edges (i.e., adsorption sites) are presented. Stepwise addition of acetylenes to the linker of a MOF yields substantially higher gravimetric surface than stepwise addition of benzene units (for comparisons at the same unit cell size).

Three series of hypothetical MOFs based on (3,24)-paddlewheel connected networks are constructed. These networks, in contrast to that for, say, MOF-5, cannot form interpenetrated structures, a practical consideration, as catenation can otherwise present a major experimental obstacle to obtaining high surface area materials. For example, a family of highly catenated (ca. 12-fold) terpyridine-based coordination polymers recently described exhibits surface areas of a few to several hundred $m^2/g$. However, the polymers would be expected to yield surface areas higher than 6,400 $m^2/g$ if they could ever be prepared in single-network form. The desired structures are constructed by incrementally adding: a) phenyl, b) phenylethynyl, or c) ethynyl groups to the $Cu_2^{II}$-paddlewheel clusters until their unit-cell edge lengths reached at least 300 Å (FIG. 4). For each series, accessible surface areas are calculated and plotted against the unit-cell lengths. As anticipated, the areas become progressively larger as the cell lengths increases. Upper limit surface areas are determined by implementing a high-quality fitting that entails the use of a five-parameter "exponential rise to max" equation. When only phenyl units are used in the linkers (FIG. 4, case A), the upper limit for the gravimetric surface area is found to be 9950 $m^2/g$, which is only slightly lower than the theoretical limit reported for MOFs derived from benzene-containing struts. When phenylethynyl groups are used (FIG. 4, case B), the upper limit of the gravimetric surface area increases to a value of 12,250 $m^2/g$. In addition, the use of only ethynyl units in the linker extensions (FIG. 4, case C) resulted in an upper limit of 14,600 $m^2/g$.

The computational modeling results clearly show that the strategy of using progressively more acetylenes in the organic linkers of MOFs, whether alone or with other molecular subunits, can create ordered structures with surface areas substantially higher than any previously envisioned for metal-organic framework materials. Further, it appears that the record-high surface area of 7,140 $m^2/g$ for compound B does not define the practical experimental upper limit for surface areas of porous materials, as it corresponds to only about 49% of the theoretical upper limit for MOFs featuring acetylene-rich linkers.

The performance of adsorbent materials such as MOFs depends on their specific surface area as well as other characteristics of the materials. As disclosed herein, for gas storage applications (such as methane), not only the number, but also the relative positions of ethynyl and phenyl groups in the organic linker can affect storage performance. The methane storage performance is assessed through the MOF working capacity, defined as the difference between the absolute amounts of methane stored at 65 bar and 5.8 bar.

The working capacity of hypothetical MOFs is assessed by calculating their adsorption isotherms (from 0 to 70 bar) at 298 K using grand canonical Monte Carlo simulations. The hypothetical MOFs studied herein were constructed by combining zirconium-based inorganic nodes ($Zr_6O_4(OH)_4$) with tetracarboxilic (TCA), and dicarboxilic acid (DCA) linkers to assemble MOFs with ftw, and fcu topologies, respectively (see FIGS. 40A and 40B).

Figure 41D:
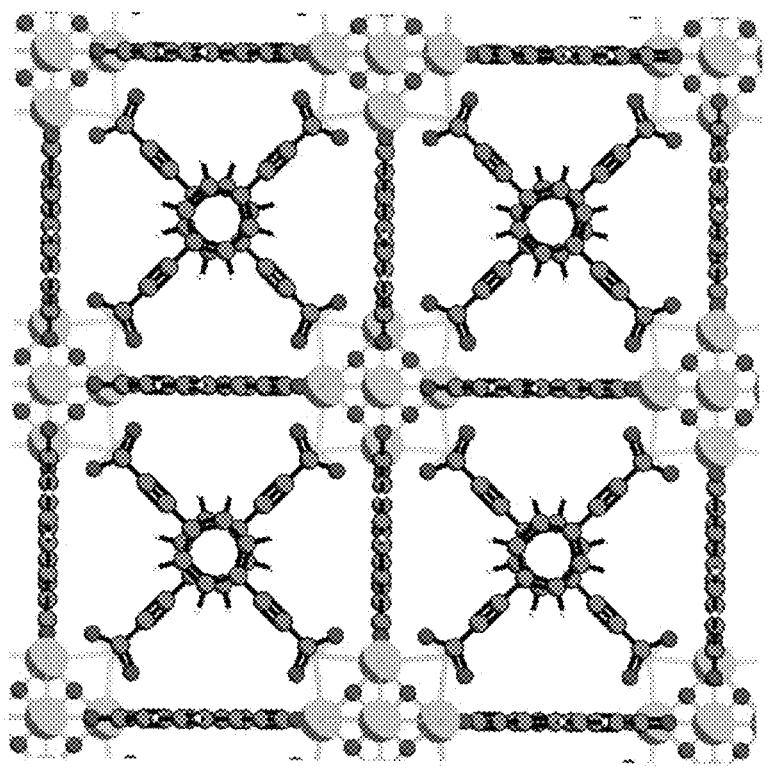
FIGS. 41D and 41E are schematic illustrations of a MOF with zirconium metal nodes and terminal ethynyl carboxylate ligands (LH$_2$-tpt) from D) a first axis and E) a second axis.
Figure 41E:
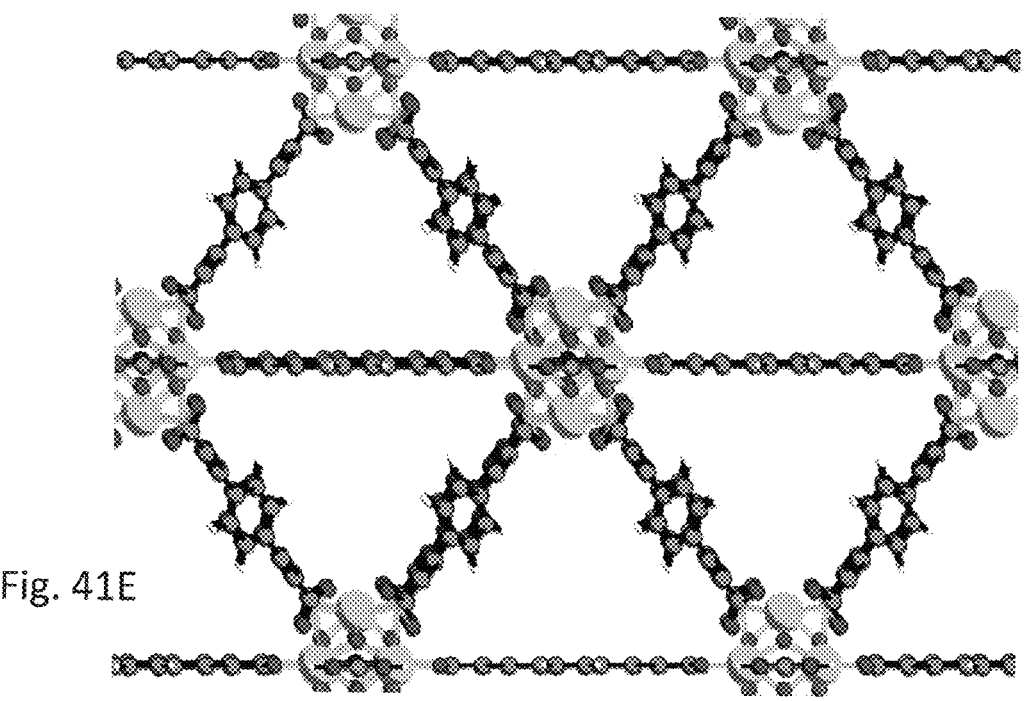

FIG. 41A shows the variety of organic building blocks used at the center of TCA linkers. The TCA linkers may be extended by using combinations of phenyl and ethynyl groups resulting in the 'peripheral' building blocks shown in FIG. 41B. DCA linkers are extended by using combinations of phenyl and ethynyl groups as well, resulting in the DCA linkers shown in FIG. 41C. FIGS. 41D and 41E illustration an example MOF with zirconium metal nodes and terminal ethynyl carboxylate ligands ($LH_2$-tpt) from two different axes.

Figure 42:
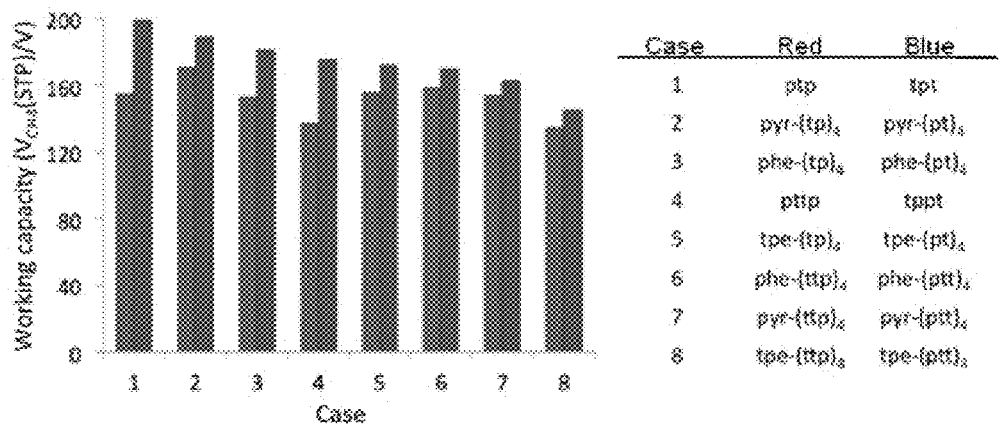
FIG. 42 is a bar diagram showing a head-to-head performance comparison between similar MOF pairs.

FIG. 42 is a bar diagram showing head-to-head volumetric surface area comparison between similar MOF pairs. For cases 2 through 8, each case correspond to a pair of isomeric MOFs as they feature exactly the same central group (for TCA linkers), and the same number of phenyl and ethynyl groups. The left bars in each pair of bars correspond to MOFs in which ethynyl groups are adjacent to the connection to the inorganic node, whereas right bars in each pair of bars correspond to MOFs where phenyl groups are adjacent to the connection to the inorganic node (see table in FIG. 42). Isomeric MOFs feature linkers that are identical in length, and therefore the unit cell used to describe their crystallographic structure is virtually of the same size. Nevertheless, FIG. 42 clearly shows that by placing the ethynyl group terminal to the organic linker, performance improvements ranging from 10 to 35 $V_{CH4}$ (STP)/V units can be achieved.

Figure 43:
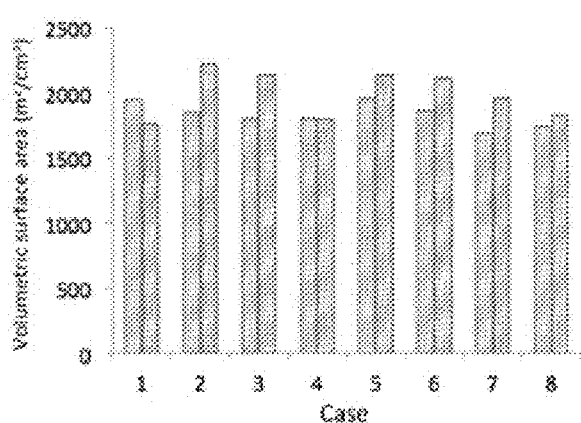
FIG. 43 is a bar diagram showing head-to-head volumetric surface area comparison between similar MOF pairs.

For MOFs with the ftw topology (all cases, but 1 and 4), the improved methane storage performance when the ethynyl group is located adjacent to the linker/node connection can be explained on the basis of improved volumetric surface area ($S_v$). This is apparent from comparison between FIGS. 42 and 43. Such improvement in volumetric surface area also correspond to an improvement in gravimetric surface area ($S_g$) since the isomeric MOF pairs disclosed herein have the same density ($\rho$), and $S_g=S_v/\rho$. However, volumetric surface area is included due to its stronger correlation with volumetric working capacity (i.e. $V_{CH4}$ (STP)/V units).

Figure 44:
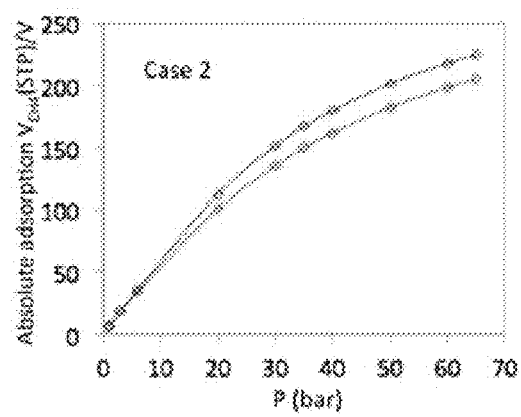
FIG. 44 is a plot illustrating absolute methane adsorption isotherms at 298 K for MOFs with pyr-(tp)$_4$ and pyr-(pt)$_4$ linkers.

Nevertheless, for the isomeric pair of fcu topology (case 4: pttp and tppt), their volumetric surface area only differs by ~10 $m^2/cm^3$, yet the working capacity of tppt is superior to that of pttp by 35 $V_{CH4}$ (STP)/V. Accordingly, placing the ethynyl group adjacent to the linker/node connection therefore brings about other benefits to the MOF besides increasing surface area. For all these cases, the performance improvement is connected to an improvement of methane adsorption at high pressure (65 bar) as shown in FIG. 44. It is noteworthy that, qualitatively, the absolute methane adsorption isotherms shown for case 2 (pyr-(tp)$_4$ and pyr-(pt)$_4$) are representative of all the other cases.

Figure 45:
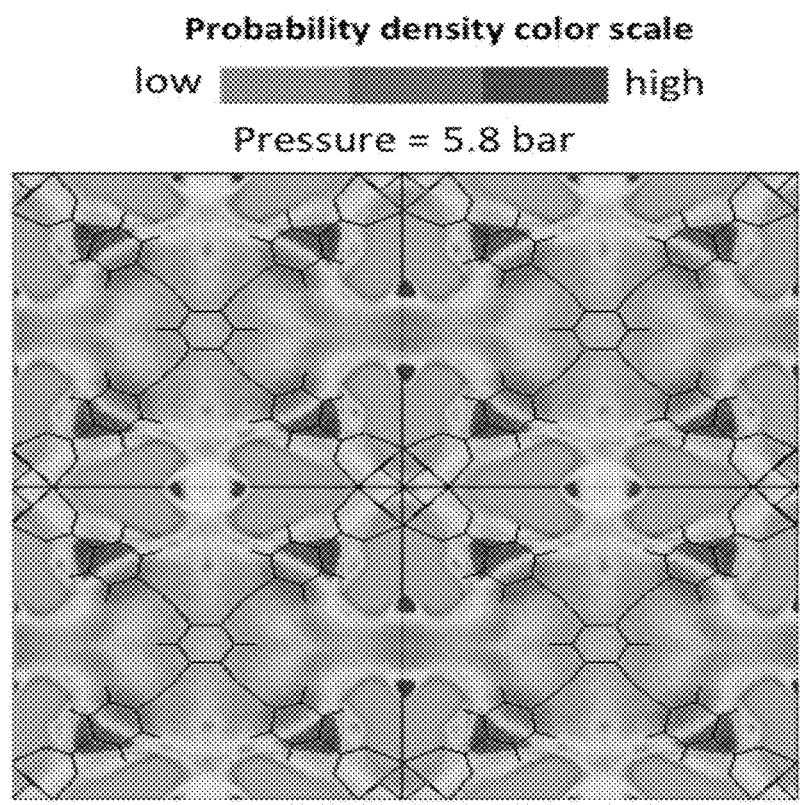
FIG. 45 is a probability density map for methane adsorption on a hypothetical ftw MOF featuring a phe-(tp)$_4$ TCA linker.

Among the additional benefits that placing the ethynyl group adjacent to the linker/node connection—instead of a phenyl group—can bring about is facilitating the access of methane molecules to the volume region near to the inorganic node, where methane/MOF interaction is typically the strongest. The comparatively strong methane/MOF interaction near the inorganic node is reflected in the higher probability of finding methane molecules in this region as shown in the probability density map shown in FIG. 45 for phe-(tp)$_4$. Given the relatively open geometrical configuration around the inorganic node region, the accessibility of this region for a single methane molecule—which is relevant at low pressure—is similar whether an ethynyl of a phenyl group is adjacent to the linker/node connection. However, a more efficient access and accumulation of a higher number of methane molecules— which is relevant to high pressure—around this region can occur when the less bulky ethynyl group is adjacent to the linker/node connection.

The statements above become apparent when comparing how two isomeric MOF pairs fill up with methane as pressure increases. FIGS. 46A-46F show snapshots at 5.8 bar and 65 bar for case 2 (i.e. pyr-(tp)$_4$ (FIGS. 46D-46F) and pyr(pt)$_4$ (FIGS. 46A-46C)) where it can be seen that, at 5.8 bar, no significant differences are apparent between the isomer MOF with the ethynyl group adjacent to the linker/node connection (pyr-(pt)$_4$) (FIGS. 46D-46F), and the isomer MOF with the phenyl group adjacent to the linker/node connection (pyr-(tp)$_4$) (FIGS. 46A-46C). In both cases, methane is rather spread around the unit cell, mostly near the inorganic node, and the central pyrene group of the TCA linker. However, once the pressure is increased to 65 bar, a more efficient packing of methane molecules around the inorganic node occurs for pyr-(pt)$_4$ compared to pyr-tp)$_4$ as evidenced from the close-ups of the node region.

The benefits of placing the ethynyl group adjacent to the linker/node connection can be observed even comparing MOF that are similar, but not isomeric. This occurs, for example, for case 1, where fcu MOFs using the DCA linkers tpt and ptp (see FIGS. 41A-41C) are compared. The ptp linker is around 1.4 Å longer that the tpt one, resulting in a slightly larger MOF unit cell for the former and rather similar helium void fractions (~0.79). Although the volumetric surface area is higher for ptp than for tpt; the simulated working capacity of tpt is around 45 $V_{CH4}$/V higher than that of ptp. Simulated snapshots of methane adsorption at 65 bar for these two MOFs confirms the higher packing of methane molecules around the inorganic node for tpt, which displayed the highest simulated working capacity among the hypothetical MOFs built and tested.

EXPERIMENTAL

Figure 9:
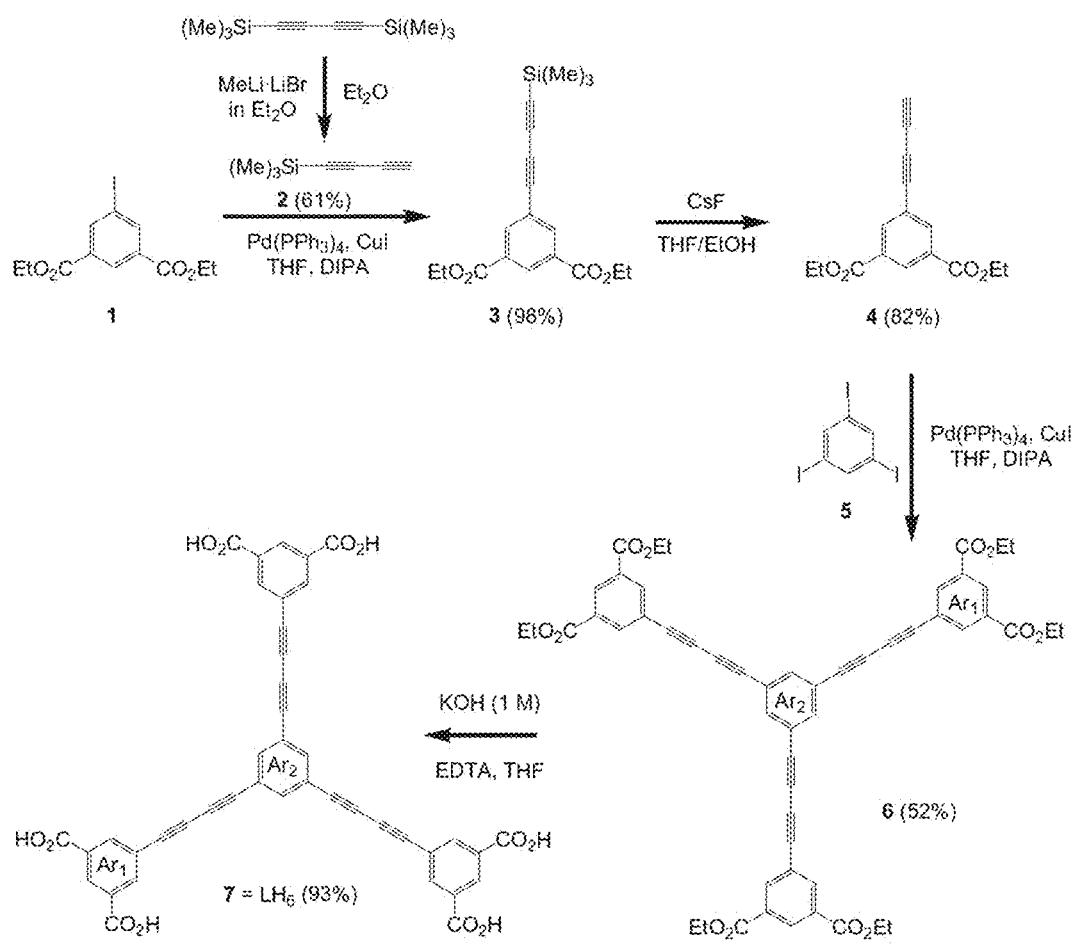
FIG. 9 is a schematic illustration of the synthesis of ligand 7 (LH$_6$) for compound C (i.e., NU-111 MOF) according to an embodiment.

All air- or water-sensitive reactions are carried out under a dry nitrogen atmosphere using standard Schlenk techniques. Compounds 1, 2, and 5 in the scheme illustrated in FIG. 9 are prepared according to previously reported procedures. Pd(PPh$_3$)$_4$ is bought from Stream chemicals (Newburyport, Mass.). Unless otherwise stated, all chemicals and solvents are purchased from Aldrich Chemicals Co. (Milwaukee, Wis.) and used without further purification. Water is obtained from a deionized water source at Northwestern University. Deuterated solvents are purchased from Cambridge Isotope Laboratories (Andover, Mass.) and used without further purification.

$^1$H and $^{13}$C NMR spectra are recorded on a Bruker 500 FT-NMR spectrometer (499.773 MHz for $^1$H, 125.669 MHz for $^{13}$C). $^1$H NMR data are reported as follows: chemical shift (multiplicity (b=broad singlet, s=singlet, d=doublet, dd=doublet of doublets, ddd=dou$_{blet}$ of doublets of doublets, t=triplet, q=quartet, and m=multiplet), integration, coupling constants, and peak assignments). $^1$H and $^{13}$C chemical shifts are reported in ppm. In $^1$H NMR spectra, the benzene rings in compounds 6 and 7 are assigned as $Ar_1$ and $Ar_2$.

Thermogravimetric analyses (TGA) are performed on a TGA/DCS 1 system (Mettler-Toledo AG, Schwerzenbach, Switzerland), which runs on a PC with STAR$^e$ software (version 9.10). Samples placed in alumina pans are heated from 25° C. to 700° C. at 10° C./minute rate under $N_2$ flow.

Supercritical $CO_2$ drying process is performed using a Tousimis™ Samdri® PVT-30 critical point dryer (Tousimis, Rockville, Md., USA). All gas isotherm measurements are carried out on an Autosorb-1 MP instrument (Quantachrome Instrument, Boynton Beach, Fla.). Measurements are performed at 77 K and 87 K are held constant using liquid $N_2$ and Ar baths, respectively.

Example 1

Figure 10:
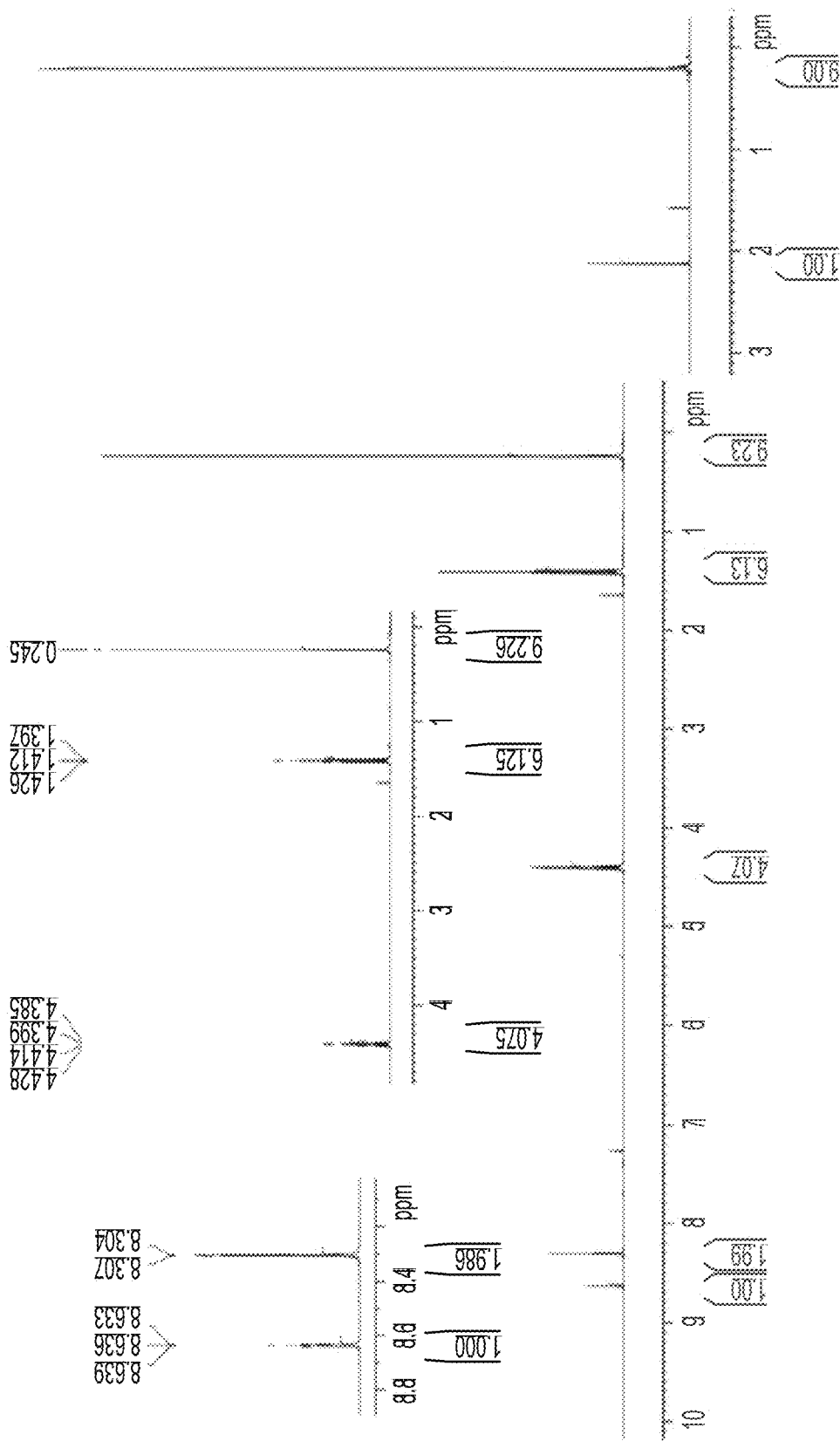
FIG. 10 is a $^1$H NMR spectrum of trimethylsilylbutadiyne recorded in CDCl$_3$.
Figure 11:
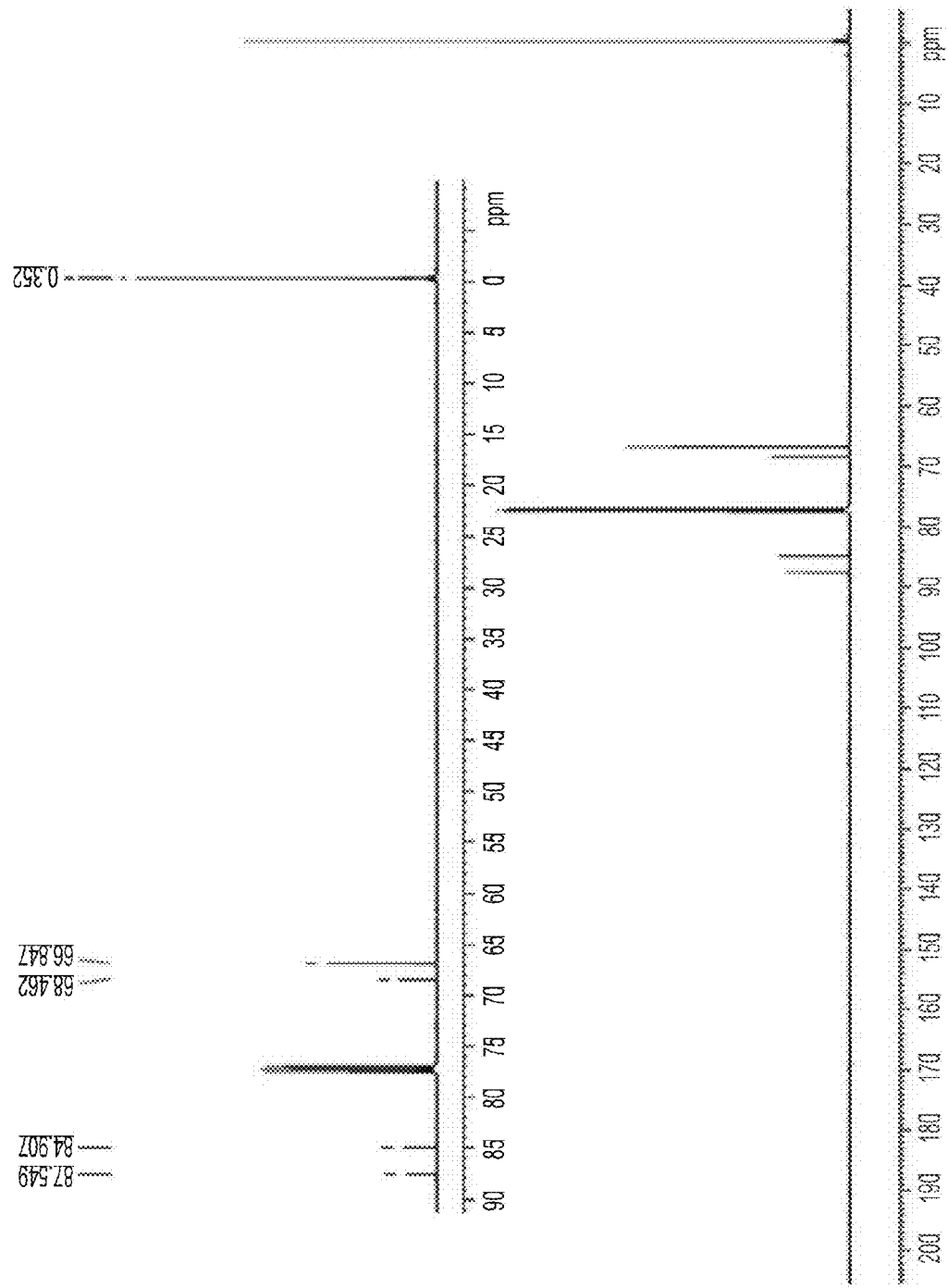
FIG. 11 is a $^{13}$C NMR spectrum of trimethylsilylbutadiyne in CDCl$_3$.

Synthesis of trimethylsilylbutadiyne (compound 2 of FIG. 9). This compound is prepared with a slight modification of a previously reported procedure. Bis(trimethylsilyl)butadiyne (25 g, 129 mmol), MeLi.LiBr (200 ml, 1.5 M in $Et_2O$, 300 mmol), and dry $Et_2O$ (800 ml) are combined in a 2000 mL round bottom flask equipped with a magnetic stir bar and a rubber stopper under $N_2$ atmosphere. The solution is stirred for 3 h at 25° C. and then cooled to 0° C. in an ice bath. MeOH is added to the cooled solution to neutralize the excess Li adduct. The mixture is extracted with saturated $NH_4Cl$ (3×200 ml) and the $Et_2O$ layer is collected, washed with brine (3×200 ml), dried over $MgSO_4$, and filtered. $Et_2O$ is then gently removed at 25° C. on a rotary evaporator. Remaining $Et_2O$ is removed in a vacuum distillation setup at 60 millitorr and 0° C. in an ice bath as a first fraction. Then, the mixture is taken out of the ice bath and compound 2 is collected at 25° C. as a clear oil from the same distillation setup. Yield=9.6 g (61%). $^1H$ NMR (500 MHz, $CDCl_3$) is shown in FIG. 10, where δ 0.21 (s, 9H, —Si($CH_3$)$_3$), 2.12 (s, 1H, —C≡CH). $^{13}C$ NMR (126 MHz, $CDCl_3$) is shown in FIG. 11, where δ 0.35, 66.85, 68.46, 84.91, and 87.55.

Example 2

Figure 12:
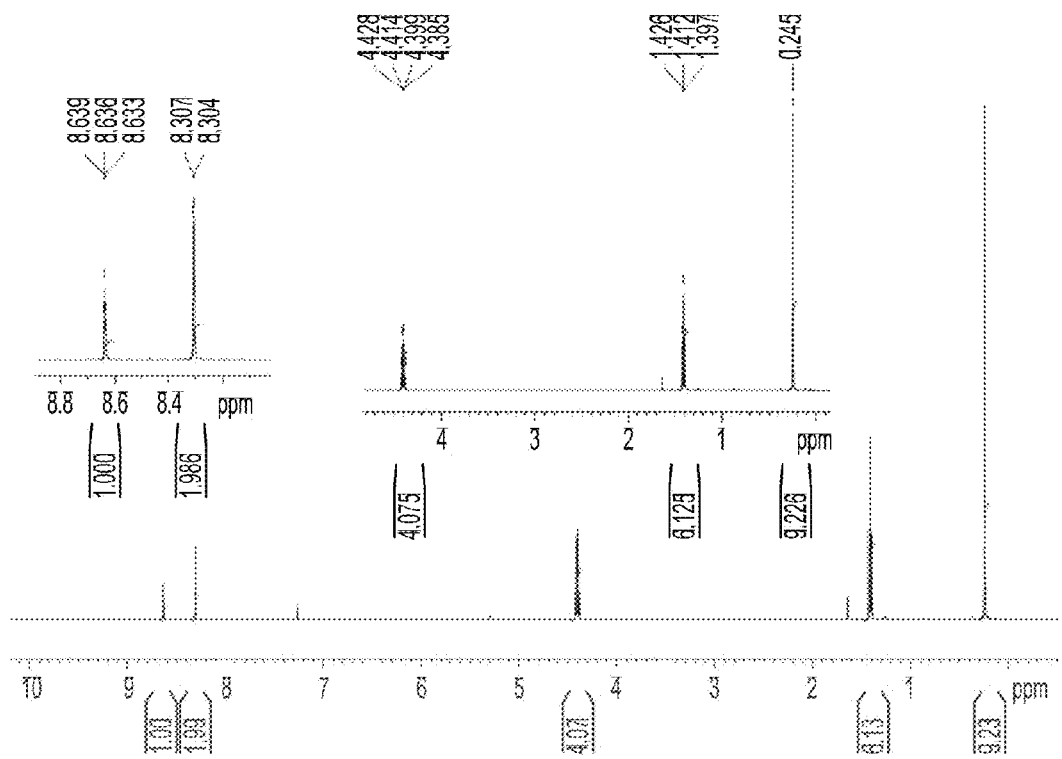
FIG. 12 is a $^1$H NMR spectrum of 1,3-diethoxycarbonyl-5-(trimethylsilylbutadiynyl)benzene recorded in CDCl$_3$.
Figure 13:
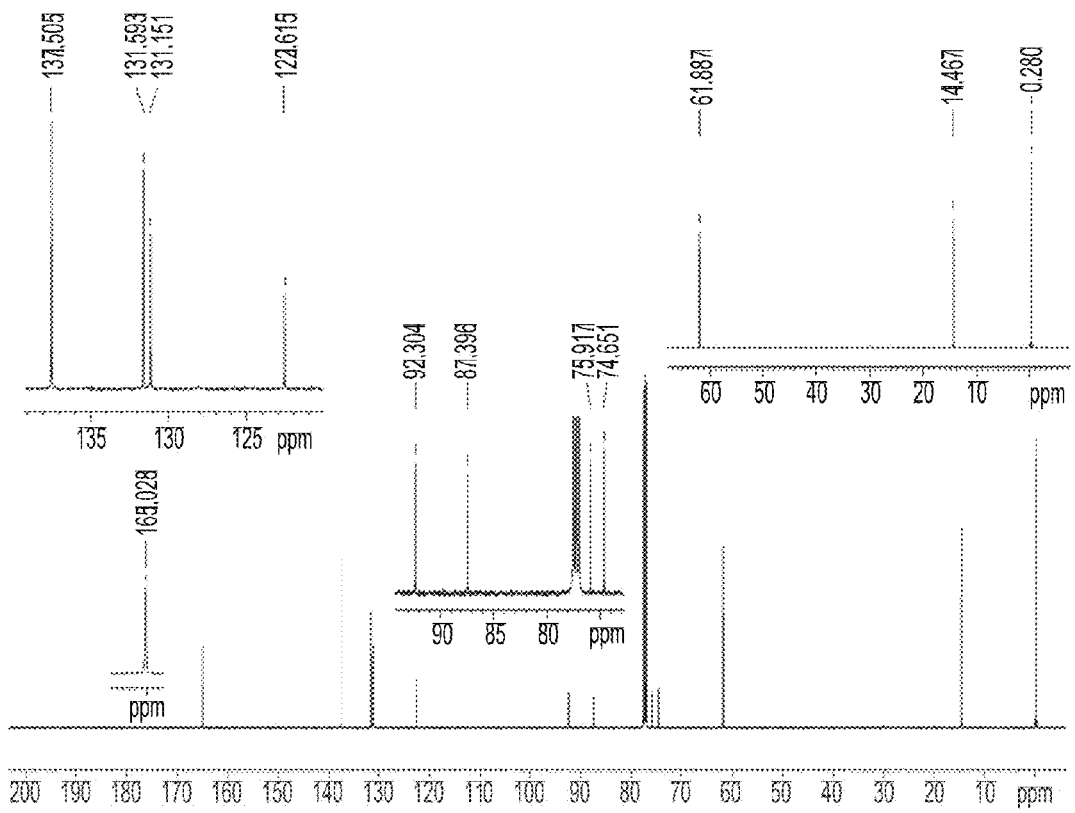
FIG. 13 is a $^{13}$C NMR spectrum of 1,3-diethoxycarbonyl-5-(trimethylsilylbutadiynyl)benzene in CDCl$_3$.

Synthesis of 1,3-diethoxycarbonyl-5-(trimethylsilylbutadiynyl)benzene (compound 3, a compound with contiguous ethynyl groups). Trimethylsilylbutadiyne (2, 6.32 g, 52 mmol), compound 1 (12 g, 35 mmol), THF (150 ml), and diisopropylamine (75 ml) is added in 500 mL Schlenk flask equipped with a magnetic stir bar and a rubber stopper. The mixture is cooled to −78° C. in an acetone/dry ice bath and subjected to three cycles of brief vacuum-degas/$N_2$ back-fill with no stirring. Then Pd(PPh$_3$)$_4$ (1.8 g, 1.56 mmol) and CuI (600 mg, 3.15 mmol) is added to this deoxygenated solution under positive $N_2$ flow and the mixture is degassed for three more cycles. The solution is stirred for 24 h at 25° C., concentrated, and dried under high vacuum. The remaining brown paste is redissolved in a minimum amount of $CH_2Cl_2$, and column chromatographed over silica gel using $CH_2Cl_2$/Hexanes (1:1, v/v) to give compound 3 as a brown solid, which is dried under high vacuum. Yield=11.7 g (98%). $^1H$ NMR (500 MHz, $CDCl_3$) is shown in FIG. 12, where δ 0.24 (s, 9H, —Si($CH_3$)$_3$), 1.41 (t, J=7.5 Hz, 6H, —$CO_2CH_2CH_3$), 4.14 (q, J=7.5 Hz, 4H, —$CO_2CH_2CH_3$), 8.31 (d, J=1.5 Hz, 2H, Ar—H), 8.64 (t, J=1.5 Hz, 1H, Ar—H). $^{13}C$ NMR (126 MHz, $CDCl_3$) is shown in FIG. 13, where δ 0.28, 14.67, 61.89, 74.65, 75.92, 87.4, 92.3, 122.62, 131.15, 137.51, and 165.03.

Example 3

Figure 14:
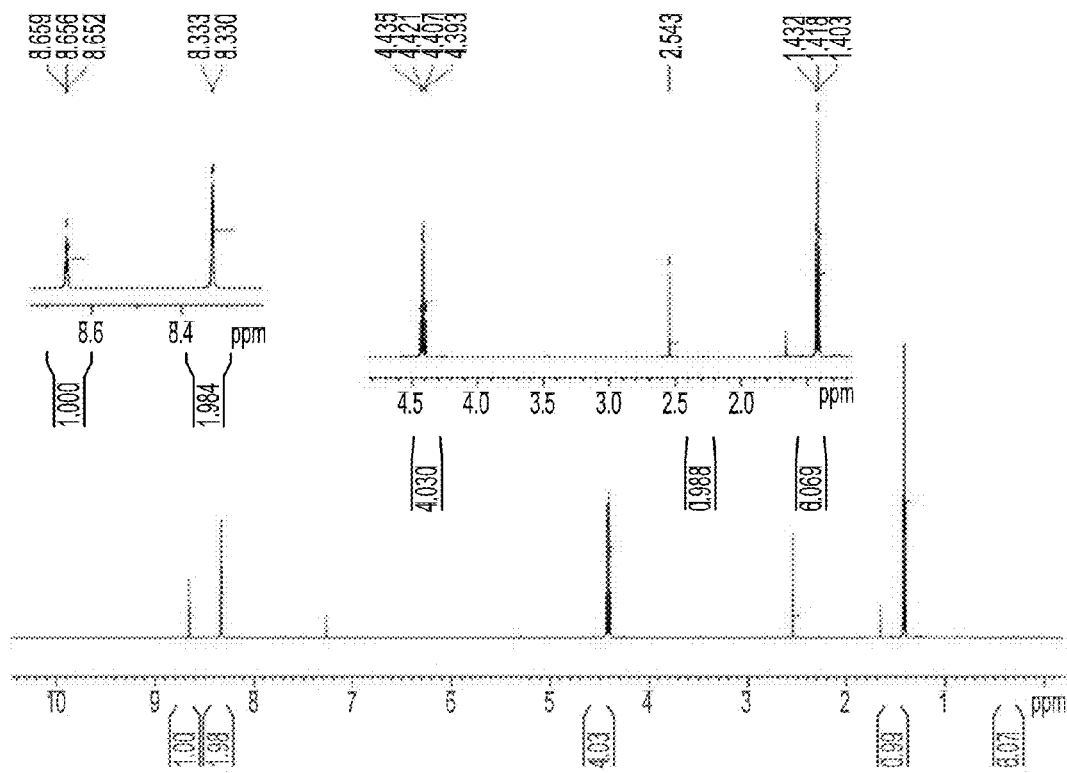
FIG. 14 is a $^1$H NMR spectrum of 1,3-diethoxycarbonyl-5-(butadiynyl)benzene recorded in CDCl$_3$.
Figure 15:
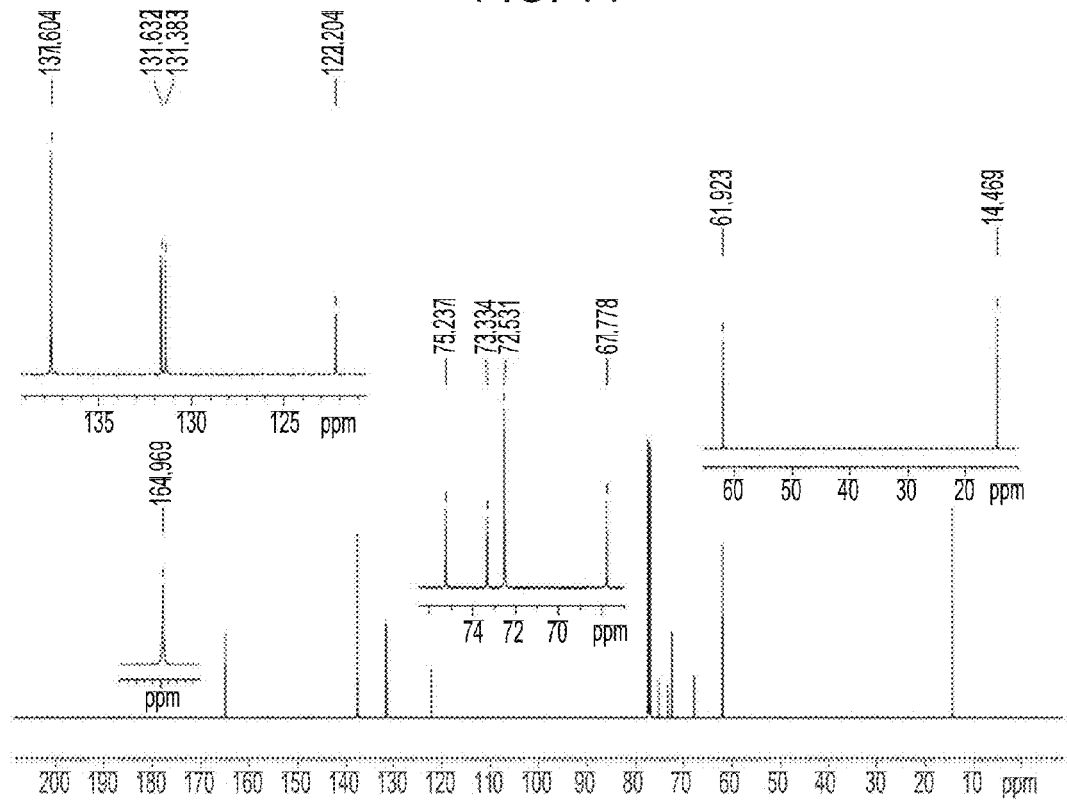
FIG. 15 is a $^{13}$C NMR spectrum of 1,3-diethoxycarbonyl-5-(butadiynyl)benzene in CDCl$_3$.

Synthesis of 1,3-diethoxycarbonyl-5-(butadiynyl)benzene (compound 4). Compound 3 (11.7 g, 34 mmol), CsF (6 g, 39.4 mmol), THF (150 ml), and ethanol (65 ml) are combined in a 500 mL round bottom flask equipped with a magnetic stir bar. (Preferably use only 99.9% ethanol since CsF is known to transesterify ethyl groups to methyl in presence of methanol.) The mixture is stirred for 2 h at 25° C., concentrated, and dried under high vacuum. The remaining black paste is redissolved in a minimal amount of $CH_2Cl_2$, and column chromatographed over silica gel using $CH_2Cl_2$ to give 4 as a yellow solid, which is dried under high vacuum. Yield=7.8 g (82%). $^1H$ NMR (500 MHz, $CDCl_3$) is shown in FIG. 14, where δ 1.42 (t, J=7.5 Hz, 6H, —$CO_2CH_2CH_3$), 2.54 (s, 1H, —C≡CH). 4.14 (q, J=7.5 Hz, 4H, —$CO_2CH_2CH_3$), 8.33 (d, J=1.5 Hz, 2H, Ar—H), 8.66 (t, J=1.5 Hz, 1H, Ar—H). $^{13}C$ NMR (126 MHz, $CDCl_3$) is shown in FIG. 15, where δ 14.67, 61.92, 67.78, 72.53, 73.33, 75.24, 122.2, 131.38, 131.6, 3 137.6, and 164.97.

Example 4

Figure 16:
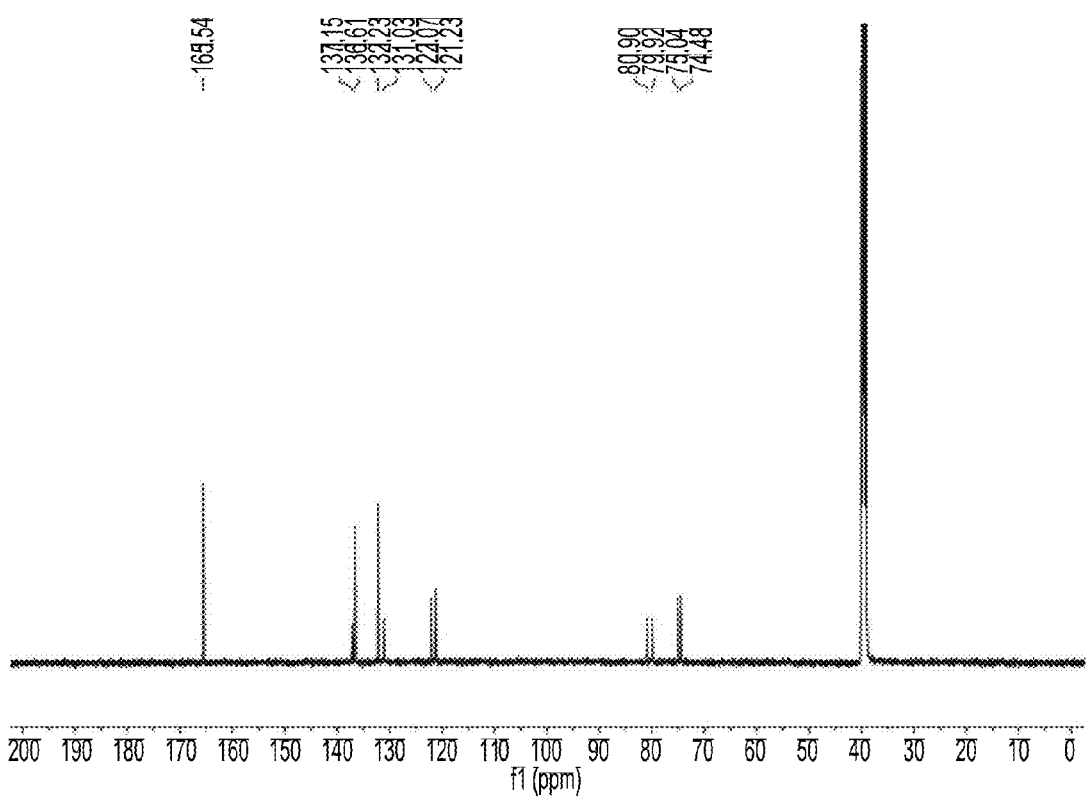
FIG. 16 is a $^1$H NMR spectrum of 1,3,5-tris[(1,3-diethylcarboxylate-5-(4-(ethynyl)phenyl))butadiynyl]-benzene recorded in CDCl$_3$.
Figure 17:
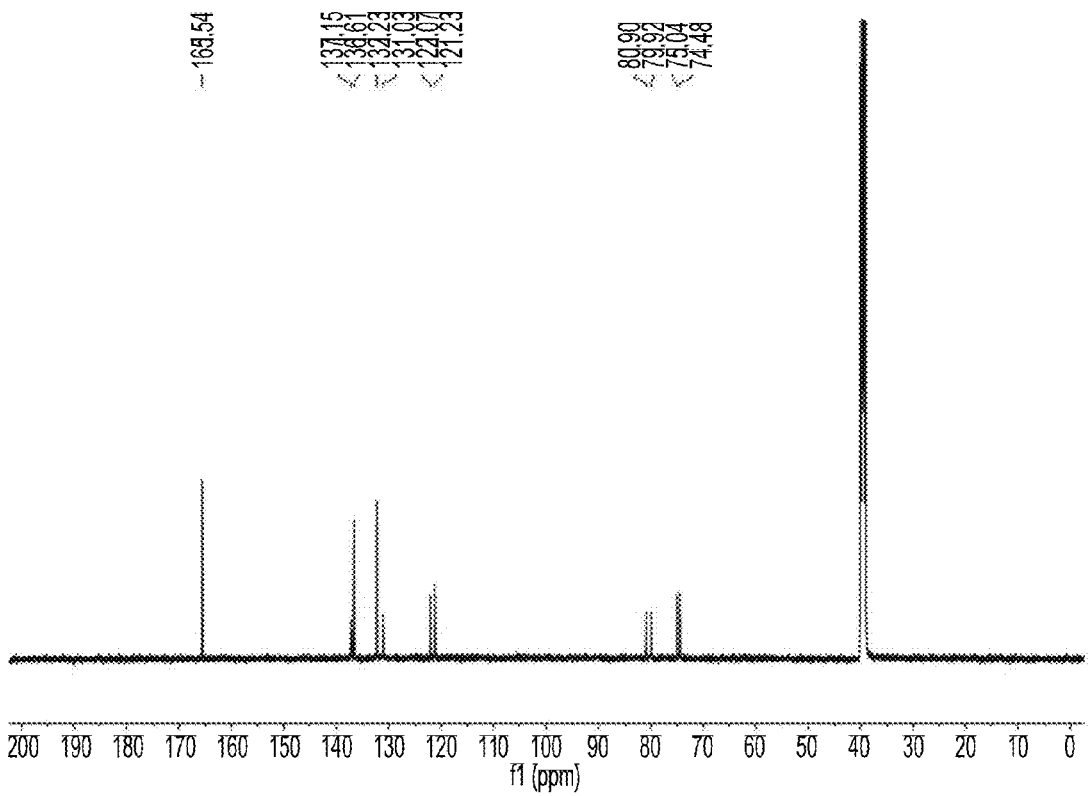
FIG. 17 is a $^{13}$C NMR spectrum of 1,3,5-tris[(1,3-diethylcarboxylate-5-(4-(ethynyl)phenyl))butadiynyl]-benzene in CDCl$_3$.

Synthesis of 1,3,5-tris[(1,3-diethylcarboxylate-5-(4-(ethynyl)phenyl))butadiynyl]-benzene (compound 6). 1,3,5-Triiodobenzene (5, 1.1 g, 2.41 mmol), compound 4 (3.0 g, 11.1 mmol), THF (100 ml), and diisopropylamine (50 ml) are combined in a 500 mL Schlenk flask equipped with a magnetic stir bar and a rubber stopper. The mixture is cooled to −78° C. in an acetone/dry ice bath and subjected to three cycles of brief vacuum-degas/$N_2$ back-fill with no stirring. Then Pd(PPh$_3$)$_4$ (450 mg, 0.39 mmol) and CuI (150 mg, 0.79 mmol) is added to this degassed solution under positive $N_2$ flow and the mixture is degassed for three more cycles. The solution is stirred for 48 h at 25° C., concentrated, and dried under high vacuum. The remaining brown paste is redissolved in a minimum amount of $CHCl_2$, and column chromatographed over silica gel using $CHCl_3$ (stabilized with 2% ethanol) to give a brown solid (2.1 g), which is recrystallized three times from $CHCl_2$:EtOH (75 ml, 2:1, v/v) to give the product 6 as an off-white solid. Yield=1.7 g (80%). $^1H$ NMR (500 MHz, $CDCl_2$) is shown in FIG. 16, where δ 1.42 (t, J=7.0 Hz, 18H, —$CO_2CH_2CH_3$), 4.43 (q, J=7.0 Hz, 12H, —$CO_2CH_2CH_3$), 7.65 (s, 3H, Ar$_2$—H), 8.35 (d, J=1.5 Hz, 6H, Ar$_1$—H), 8.67 (t, J=1.5 Hz, 3H, Ar$_1$—H). $^{13}C$ NMR (126 MHz, $CDCl_2$) is shown in FIG. 17, where δ 14.43, 61.88, 75.13, 75.50, 79.78, 80.63, 122.45, 123.00, 131.29, 131.60, 136.72, 137.36, and 164.92.

Example 5

Figure 18:
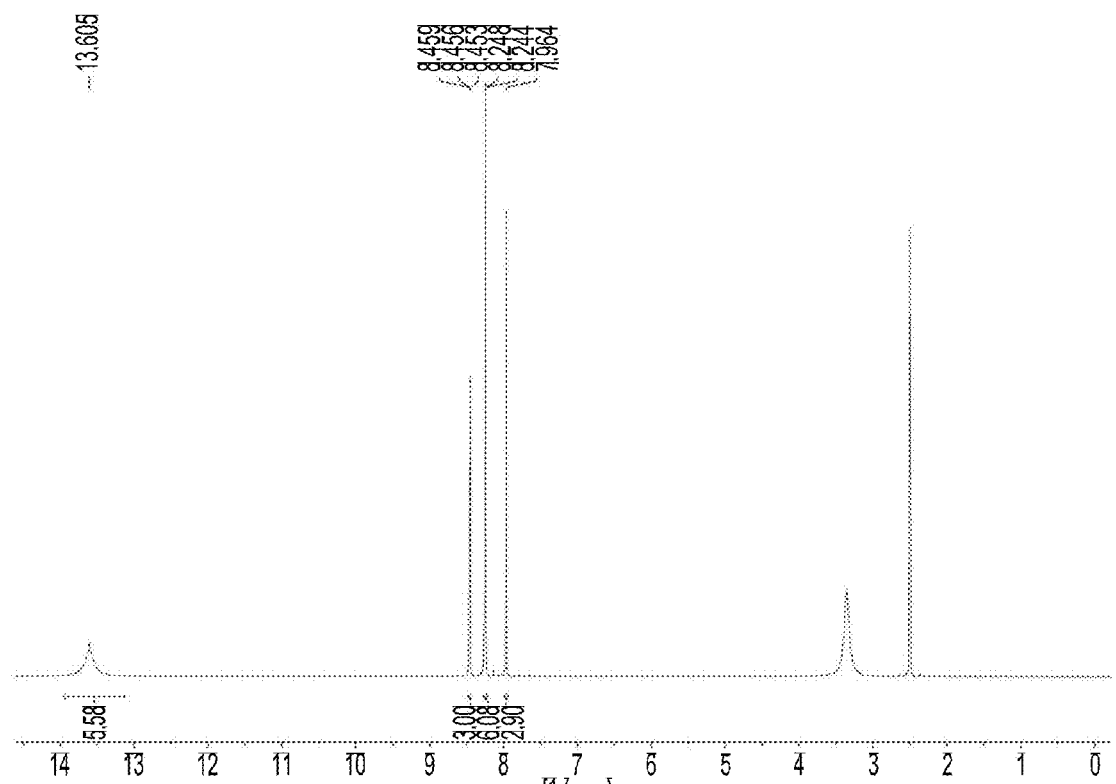
FIG. 18 is a $^1$H NMR spectrum of 1,3,5-tris[(1,3-carboxylic acid-5-(4-(ethynyl)phenyl))butadiynyl]-benzene recorded in DMSO-d$_6$.
Figure 19:
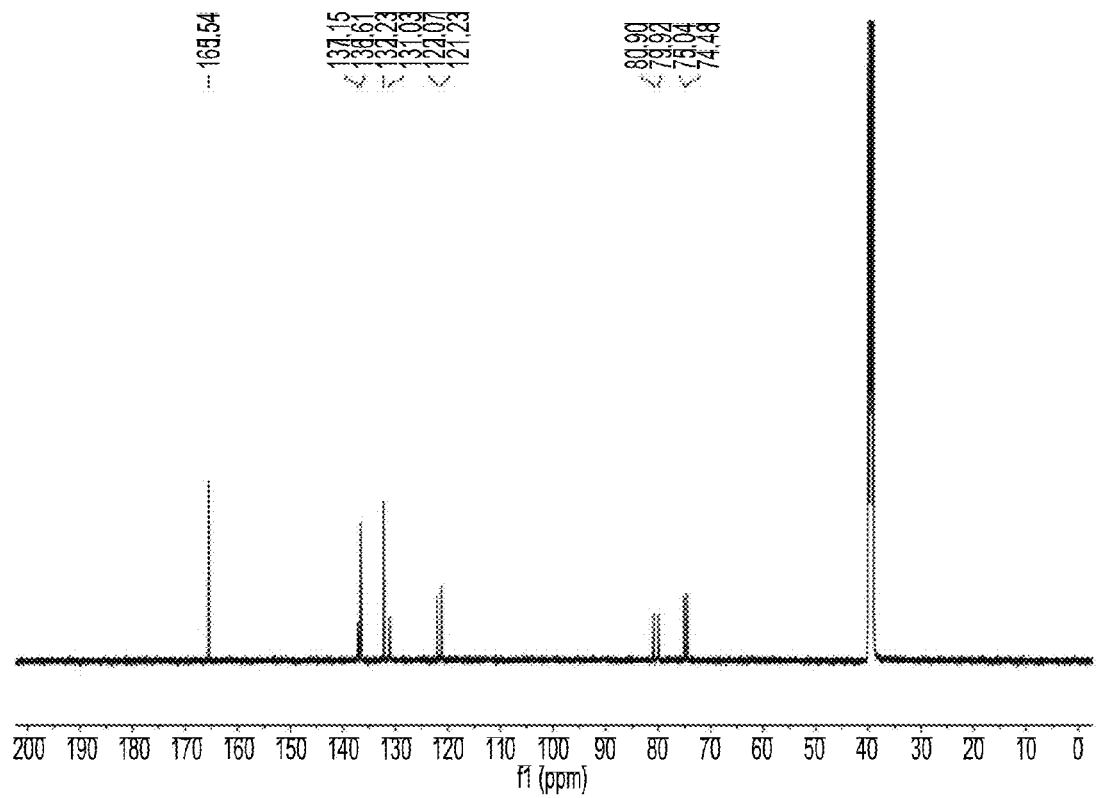
FIG. 19 is a $^{13}$C NMR spectrum of 1,3,5-tris[(1,3-carboxylic acid-5-(4-(ethynyl)phenyl))butadiynyl]-benzene in DMSO-d$_6$.
Figure 20:
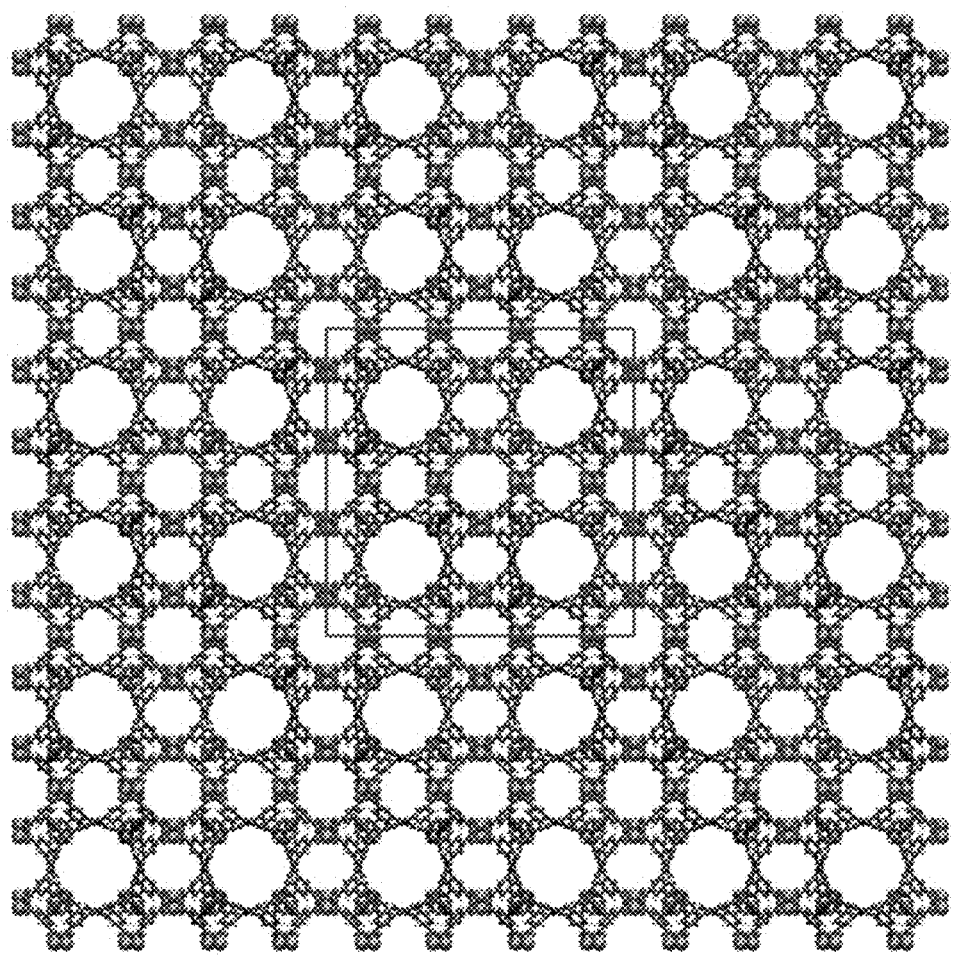
FIG. 20 is a schematic illustration showing the packing of NU-111 in a 3×3×3 unit cell in X-ray crystal structure looking down the a-axis.

Synthesis of 1,3,5-tris[(1,3-carboxylic acid-5-(4-(ethynyl)phenyl))butadiynyl]-benzene (compound 7=LH$_6$, a linker with contiguous ethynyl groups). Compound 6 (1.0 g, 1.13 mmol) is dissolved in THF (40 ml) in a 500 mL round bottom flask equipped with a magnetic stir bar. Then, KOH (80 ml, 1 M aqueous solution, 80 mmol) and EDTA.2Na (1.0 g, 2.69 mmol) are added to this solution, which turned into a suspension. The suspension is stirred for 68 h at 60° C. until it became clear. THF is removed using a rotary evaporator and the remaining aqueous solution is acidified to pH 2 using concentrated HCl (10 mL of a 37% aqueous solution). The resulting precipitate is collected via centrifugation (6500 rpm), washed with $H_2O$ (200 mL), and dried under high vacuum to afford 7 (LH$_6$) as a dark yellow solid. Yield=716 mg (91%). $^1H$ NMR (500 MHz, DMSO-d$_6$) is shown in FIG. 18, where 7.92 (s, 3H, Ar$_2$—H), 8.25 (d, J=2.0 Hz, 6H, Ar$_1$—H), 8.46 (t, J=1.5 Hz, 3H, Ar$_1$—H), 13.61 (s, 6H, Ar$_1$—$CO_2H$). $^{13}C$ NMR (126 MHz, DMSO-d$_6$) is shown in FIG. 19, where δ 74.48, 75.04, 79.92, 80.90, 121.23, 122.07, 131.03, 132.23, 136.61, 137.15, and 165.54.

Example 6

Synthesis of compound C—Cu(NO$_3$)$_2$.2.5H$_2$O (900 mg, 3.87 mmol) and LH$_6$ (7) (300 mg, 0.42 mmol) are dissolved in DMF (75 ml). Then EtOH (75 ml) and HCl (1.4 ml) are added to this mixture. This solution (151.4 ml) is divided into sixty 2-dram vials (VWR, catalog #66011-085). The vials are capped and placed in an oven at 80° C. for 48 h. The resulting teal crystals are washed with DMF without drying. Yield calculated from evacuated sample=75% based on LH$_6$.

Example 7

Figure 21:
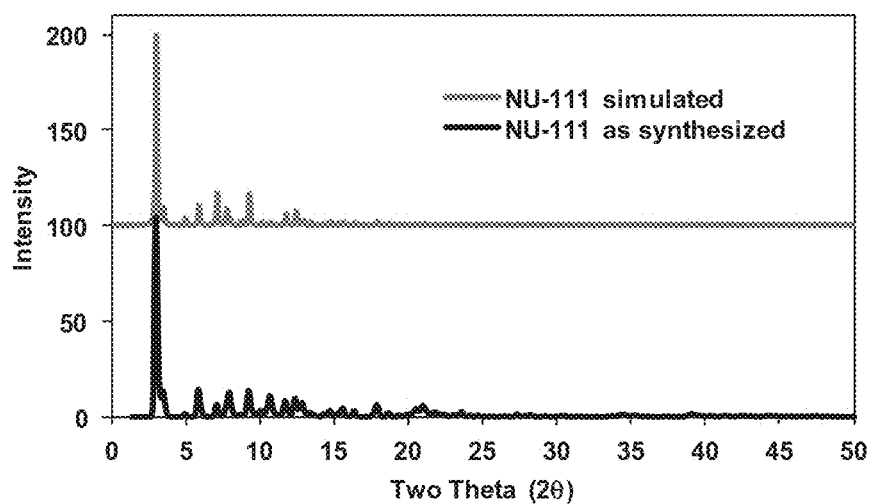
FIG. 21 is plot of PXRD patterns: as-synthesized (bottom) and simulated (top) of NU-111 according to an embodiment.

X-ray crystallography analysis of compound C is shown in FIG. 21 for simulated and synthesized compound C (i.e., MOF NU-111). Single crystals of compound C, are mounted in oil on glass fibers and placed in the nitrogen cold stream at 225 K of a Bruker AXS APEX2 diffractometer equipped with a CCD detector and an IμS CuKα microfocus source with MX optics. All data are corrected for absorption via SAD-ABS. Structures are solved and refined using the SHELXTL suite of software. The solvent masking procedure in Olex2 is used to remove electronic contributions from solvent molecules for each structure.

Powder patterns for compound C are collected on a Bruker AXS APEX2 diffractometer equipped with a CCD detector and a CuKα IμS microfocus source with MX optics. Samples are loaded into glass capillaries with a small amount of mother liquor, and mounted on a goniometer head. Data are collected with an area detector as rotation frames over 180° in φ at 2θ values of 12°, 24°, and 36° and exposed for 10 minutes for each frame. At a distance of 150 mm, the detector area covers 24° in 2θ. Overlapping sections of data are matched and the resulting pattern integrated using the Bruker APEX2 Phase ID program. Powder pattern data are treated for amorphous background scatter (EVA 16, Copyright Bruker-AXS 1996-2010).

Example 8

Activation of Compound C—After vials are removed from the oven, the mother liquor is decanted while warm and ethanol (absolute) is added on the crystals. The ethanol is then decanted and replaced daily for three days and the crystals are left in ethanol until the next step. Approximately 150 mg of teal colored crystals are transferred into a Tousimis Samdri-PVT-3D super-critical $CO_2$ dryer. Excess ethanol is decanted, the temperature is lowered to 0° C., and the chamber is filled with liquid $CO_2$ (ultrahigh grade $CO_2$ with a siphon from Air-Gas Inc is used). The sample is soaked for 10 hours total, venting for 5 min every 2 hours. Full exchange of ethanol for liquid $CO_2$ in the pores of the crystals is signaled by a color change to a cerulean blue. The chamber is then heated to 40° C., and the super-critical $CO_2$ is bled off at a rate of 0.5 ml/min until the chamber is at ambient pressure (approximately 12 hrs). The chamber is opened and the sample is quickly sealed and taken into an argon atmosphere glove box for further manipulations. Dried crystals are transferred into a pre-weighed glass sample tube. The tube is sealed and quickly transferred to a system providing $10^{-4}$ torr dynamic vacuum. The sample is kept under vacuum at room temperature for 2 hours then heated to 110° C. over 2 hours and held at 110° C. for 16 hours (still under vacuum). The sample is then used for gas adsorption measurements. After gas adsorption measurements the sample is returned to the argon atmosphere glove box and a final mass calculated.

Example 9

Experimental high-pressure hydrogen adsorption by compound C—High-pressure hydrogen capacity measurements are performed on a modified commercial Sieverts system (PCTPro 2000). One hardware modification consisted of adding a manifold to the high-pressure gas inlet that allows either hydrogen or helium to be introduced. In this way, exactly the same protocol could be used for the hydrogen measurements and for the helium calibration procedure (discussed below). Another hardware modification consists of supplementing the as-received temperature-control system so that the temperature-controlled region is expanded to include the sample support arm and the sample chamber assembly (sample chamber, manual isolation valve, and 0.125 inch OD connection tubing) using temperature-controlled water circulating through copper components physically connected to the sample chamber assembly. The temperatures of the internal cabinet and the external circulator are equal and this modification improves the overall temperature stability of the apparatus. For measurements at 303 K, the sample chamber is immersed in stirred water in a double-jacketed dewar where the circulator water flows through the jacket. For measurements at 75.6 K (the boiling point of liquid nitrogen at an altitude of 6000 ft.—Golden, Colo.), the sample chamber is immersed in liquid nitrogen in a glass-walled vacuum dewar covered with a foam insulating cap. An OFHC split copper cylinder is clamped to the 0.125 inch tubing so that the copper extended up to the foam lid and is always partially submerged in the liquid nitrogen; this copper piece helped to mitigate that effect of the falling liquid nitrogen level over time on the temperature profile and to extend the liquid nitrogen temperature up to the lid. Just above the foam lid is another split copper cylinder also clamped to the tubing and the 303 K circulator water passes through this upper copper cylinder. In this way, the temperature gradient between 303 K and the lower copper cylinder is confined spatially to the thickness of the foam lid. Finally, the liquid nitrogen level is monitored throughout the measurement and is maintained to lie within a 1.5 cm range to ensure that the lower copper cylinder is always at least half submerged in the liquid nitrogen. These measures allow the temperature profile of the sample volume to be stable and reproducible.

In an embodiment, the samples are degassed on a custom-built degassing station with two turbo pumps yielding a base pressure of $10^{-7}$ torr and the effluents from the sample can be monitored by a mass spectrometer. Typically, samples are evacuated at room temperature for 05-2 hours, such as 1 hour, and then the temperature is increased to 90-120° C., such as 110° C. over two hours, and then held at 110° C. for approximately 10-20 hours, such as 14 hours, all under evacuation. Since the sample chamber assembly has a manual isolation valve, the sample chamber can be transferred between the degassing station and the Sieverts apparatus without exposure to air. The Sieverts protocol consisted of the following sequence after the degassing is accomplished:

1) Measure hydrogen capacity of sample at liquid nitrogen.
2) Warm to 303 K and pump off hydrogen (base pressure $10^{-5}$ torr) for 1 hour.
3) Measure hydrogen capacity of sample at 303 K.
4) Perform helium calibration at 303 K with sample present.
5) Remove sample material and reassemble empty sample chamber assembly.
6) Perform helium calibration at liquid nitrogen on empty sample chamber.
7) Perform helium calibration at 303 K on empty sample chamber.

For each measurement step, the pressure is held for 5-20 minutes, such as 10 minutes to allow the sample to come to equilibrium, which is consistent with the physisorption mechanism expected in these materials. For the 303 K capacity determination, steps 3 and 4 are sufficient; while for the 75.6 K measurement, steps 1, 4, 6 and 7 are also performed. These steps allow calculation of the sample skeletal volume (steps 4 and 7) and the calculation of the warm and cold empty volumes (steps 6 and 7). The sample skeletal volume can then be subtracted from the empty volumes to yield the cold volume with the sample present. The volume and gas density for the temperature gradient region may be calculated directly assuming a linear temperature gradient and the geometrical dimension of the tubing. The preferred characteristics for the above protocol are that the sample chamber volume be repeatable to a high degree upon disassembly and re-assembly as well as the repeatability of the temperature profile both at 303 K, any temperature gradients, and the volume at liquid nitrogen temperatures. These requirements have been thoroughly verified through control experiments on empty sample chambers.

The above protocol avoids helium adsorption effects on the sample at low temperatures for the calibration steps when it is expected to be the most significant. Instead, the sample is only exposed to helium at 303 K where the effects are much reduced. The helium adsorption that occurs at 303 K is assumed to be negligible. Not compensating for helium adsorption effects will yield capacity measurements that underestimate the hydrogen adsorption. As mentioned above, because of the modification that allows helium to be introduced into the high-pressure port of the instrument, the exact same measurement protocol used for hydrogen can also be done with helium. This provides a higher degree of confidence for the helium calibration and can also investigate any calibration effects dependent on pressure.

Data analysis to determine hydrogen capacities is performed using custom analysis procedures to ensure the accuracy and proper handling for the temperature profile of the sample chamber. The analysis is based on a mass-balance model of the gas phase where missing gas is assumed to be adsorbed onto the sample and surplus gas is assumed to have desorbed from the sample. A real equation of state is used for the gases and the compressibility factor is based on calculations using GASPAK for helium and hydrogen.

Example 10

Molecular Simulations of Compound C—Atomistic grand canonical Monte Carlo (GCMC) simulations are performed to estimate the adsorption isotherms of $CH_4$, $N_2$, and $H_2$ in compound C.

Interaction Potential.

For simulations of $N_2$ adsorption, interaction energies between non-bonded atoms are computed through a Lennard-Jones (LJ)+Coulomb potential:

$$v_{ij} = 4\epsilon_{ij}\left(\left(\frac{\sigma_{ij}}{r_{ij}}\right)^{12} - \left(\frac{\sigma_{ij}}{r_{ij}}\right)^{6}\right) + \frac{q_i q_j}{4\pi\epsilon_0 r_{ij}}$$

where i and j are interacting atoms, and $r_{ij}$ is the distance between atoms i and j, $\epsilon_{ij}$ and $\sigma_{ij}$ are the LJ well depth and diameter, respectively, $q_i$ and $q_j$ are the partial charges of the interacting atoms, and $\epsilon_0$ is the dielectric constant. LJ parameters between different types of sites were calculated using the Lorentz-Berthelot mixing rules.

For simulations of $H_2$ adsorption at 77 K, quantum diffraction effects become important, which can be accounted for using the quasiclassical Feynman-Hibbs (FH) potential. Hydrogen may be modeled at this temperature as follows:

$$v_{ij} = 4\epsilon_{ij}\left(\left(\frac{\sigma_{ij}}{r_{ij}}\right)^{12} - \left(\frac{\sigma_{ij}}{r_{ij}}\right)^{6}\right) + \overbrace{\frac{4\epsilon_{ij}}{r_{ij}^2}\frac{\hbar^2}{24\mu_{ij}k_BT}\left(132\left(\frac{\sigma_{ij}}{r_{ij}}\right)^{12} - 30\left(\frac{\sigma_{ij}}{r_{ij}}\right)^{6}\right)}^{\text{FH Correction}} + \frac{q_i q_j}{4\pi\epsilon_0 r_{ij}}$$

where $\mu_{ij}$ is the reduced mass, $m_i m_j/(m_i+m_j)$ of the two interacting atoms having atomic masses $m_i$ and $m_j$, T is the temperature, and $k_B$ and $\hbar$ are Boltzmann's constant and Planck's constant, respectively. For comparison, simulations without the middle Feynman-Hibbs "correction" term is also run.

MOF Models.

LJ parameters for the framework atoms are taken from the Universal Force Field (UFF). Partial charges are determined using the extended charge equilibration (EQeq) algorithm developed by Wilmer et al., assuming neutral charge centers for all atoms except Cu, for which a +2 charge center is used, and assuming a global relative dielectric permittivity or 1.67. Table 3 shows the LJ parameters for framework atom types found in compound C.

TABLE 3

| Atom type | $\sigma$ (Å) | $\epsilon/k_B$ (K) |
|---|---|---|
| C | 3.43 | 52.83 |
| O | 3.12 | 30.19 |
| H | 2.57 | 22.14 |
| Cu | 3.114 | 2.516 |

Nitrogen Model.

Nitrogen molecules are modeled using the TraPPE force field, which is originally fit to reproduce the vapor-liquid coexistence curve of nitrogen. In this force field, the nitrogen molecule is a rigid structure where the N—N bond length is fixed at its experimental value of 1.10 Å. This model reproduces the experimental gas-phase quadrupole moment of nitrogen by placing partial charges on N atoms and on a point located at the center of mass (COM) of the molecule. Table 4 shows the LJ parameters and partial charges for nitrogen.

TABLE 4

| Atom type | $\sigma$ (Å) | $\epsilon/k_B$ (K) | q (e) |
|---|---|---|---|
| N | 3.31 | 36.0 | −0.482 |
| $N_2$ COM | 0 | 0 | 0.964 |

Hydrogen Model.

For the hydrogen molecules, the model of Levesque et al. is used and simulations are run with and without the FH correction. In this model, the hydrogen molecule is a rigid structure where the H—H bond length is fixed at 0.74 Å. This model reproduces the experimental gas-phase quadrupole moment of hydrogen by placing partial charges on H atoms and on a point located at the center of mass (COM) of the hydrogen molecule. Table 5 shows the LJ parameters and partial charges for hydrogen.

TABLE 5

| Atom type | $\sigma$ (Å) | $\epsilon/k_B$ (K) | q (e) |
|---|---|---|---|
| H | 0 | 0 | 0.468 |
| $H_2$ COM | 2.958 | 36.7 | −0.936 |

Methane Model.

The methane molecules were modeled using the TraPPE force field, which was originally fit to reproduce the vapor-liquid coexistence curve of methane. In this force field, methane is modeled as a single sphere with the parameters shown in Table 6.

TABLE 6

| Atom type | $\sigma$ (Å) | $\epsilon/k_B$ (K) | q (e) |
|---|---|---|---|
| $CH_4$ (united) | 3.75 | 148.0 | — |

General GCMC Simulation Settings.

All GCMC simulations include a 2500-cycle equilibration period followed by a 2500-cycle production run. A cycle consists of n Monte Carlo steps, where n is equal to the number of molecules (which fluctuates during a GCMC simulation). All simulations include random insertion/deletion, translation and rotation moves of molecules with equal probabilities. Atoms in the MOF are held fixed at their crystallographic positions. A LJ cutoff distance of 12.0 Å is used for all simulations. The Ewald sum technique is used to compute the electrostatic interactions. One unit cell of compound C is used for the simulations. $N_2$ isotherms are simulated at 77 K up to 0.431 bar. $H_2$ isotherms are simulated at 77 K up to 100 bar. Fugacities needed to run the GCMC simulations are calculated using the Peng-Robinson equation of state. GCMC simulations report the absolute data which are then used to compute the excess adsorption data for comparison with experimental data using the relation: $N_{total} = N_{excess} + \rho_{gas} V_p$, where $\rho_{gas}$ is the bulk density of the gas at simulation conditions and $V_p$ is the pore volume calculated by the helium insertion method as detailed elsewhere.

The Pore-size Distribution (PSD).

The PSD is calculated using the experimental compound C crystal structure by inserting spheres at random locations within the framework and growing them until they collide with either (a) the surface of a framework atom, where the framework atomic diameters are given by the sigma values in the Universal Force Field (UFF), or (b) the center of mass of the atoms. The latter case, remarkably, where the atoms of the framework are treated as points, shows better agreement with the experimental PSD determined by NLDFT methods. The reasons for the better agreement of the latter case are unclear, but the likely explanation is that the PSD determined by the NLDFT fitting procedure overestimates the pore diameters by approximately the diameter of the atoms enclosing the cavity (as defined by the UFF sigma value).

FIGS. 24 to 39 illustrate various features of the pore distribution of compound C (i.e., NU-111).

Figure 24:
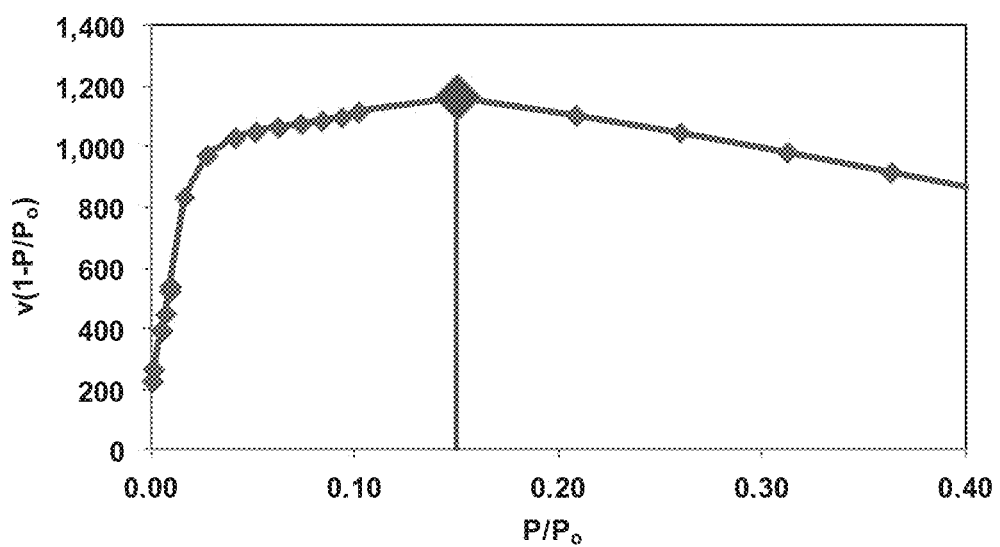
FIG. 24 is a consistency plot of an experimental N$_2$ isotherm in NU-111 according to an embodiment.

FIG. 24 is a consistency plot of an experimental $N_2$ isotherm in NU-111 according to an embodiment.

Figure 25:
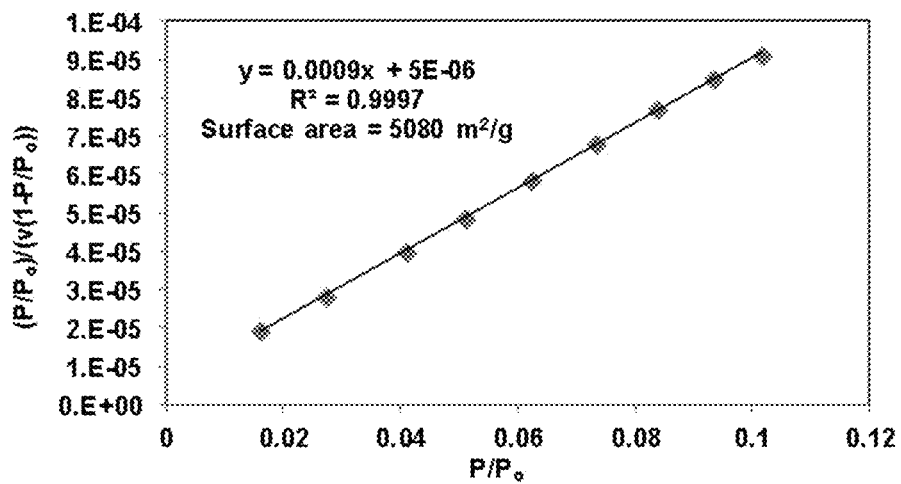
FIG. 25 is a plot of the linear region for the BET equation satisfying the second criterion for application of the BET theory from an experimental N$_2$ isotherm according to an embodiment.

FIG. 25 is a plot of the linear region for the BET equation satisfying the second criterion for application of the BET theory from an experimental $N_2$ isotherm according to an embodiment.

Figure 26:
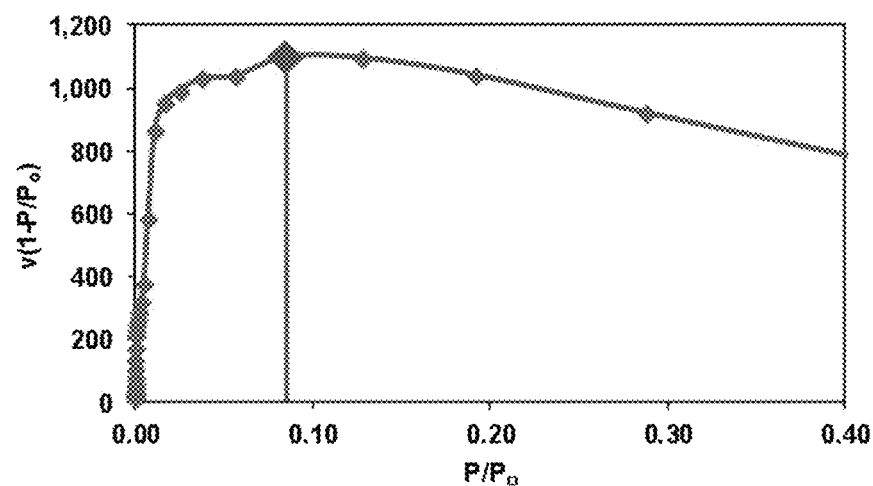
FIG. 26 is a consistency plot for simulated N$_2$ isotherm in NU-111 according to an embodiment.

FIG. 26 is a consistency plot for simulated $N_2$ isotherm in NU-111 according to an embodiment.

Figure 27:
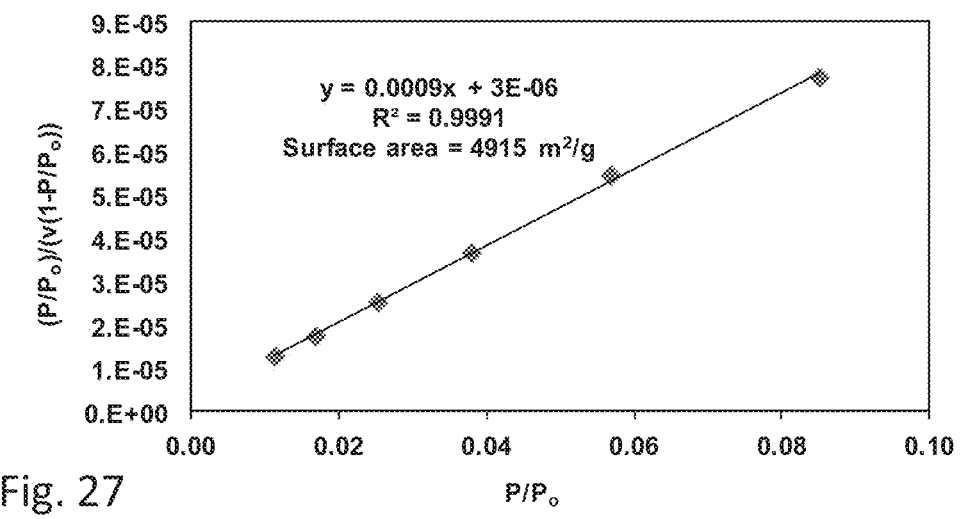
FIG. 27 is plot of the linear region for the BET equation satisfying the second criterion for application of the BET theory from simulated N$_2$ isotherm according to an embodiment.

FIG. 27 is plot of the linear region for the BET equation satisfying the second criterion for application of the BET theory from simulated $N_2$ isotherm according to an embodiment.

Figure 28:
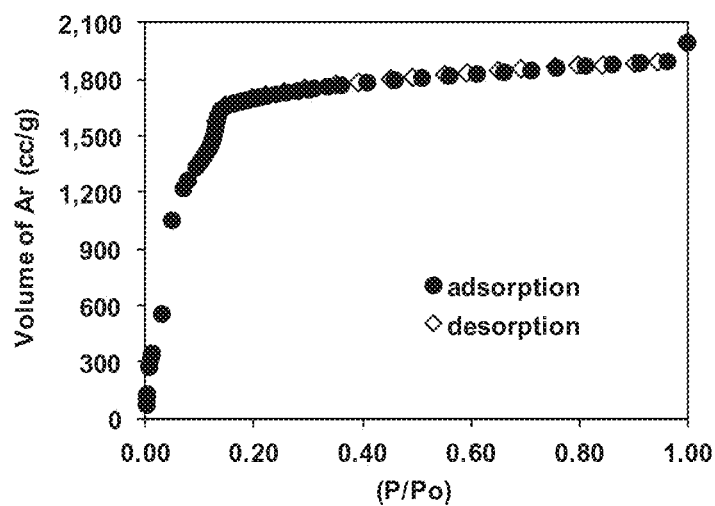
FIG. 28 is a plot of experimental Ar adsorption and desorption isotherms for NU-111 at 87 K 20 according to an embodiment.

FIG. 28 is a plot of experimental Ar adsorption and desorption isotherms for NU-111 at 87 K 20 according to an embodiment.

Figure 29:
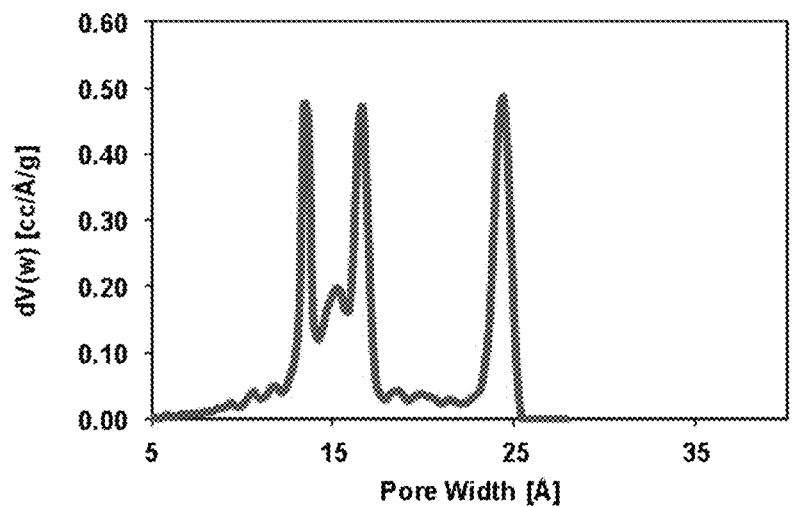
FIG. 29 is a plot illustrating a simulated pore size distribution of NU-111 using the center of mass of the atoms.

FIG. 29 is a plot illustrating a simulated pore size distribution of NU-111 using the center of mass of the atoms.

Figure 30:
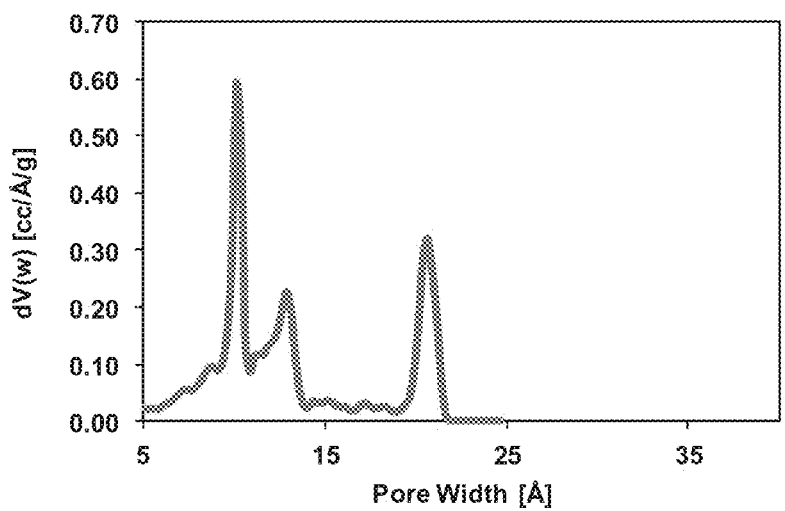
FIG. 30 is a plot illustrating a simulated pore size distribution of NU-111 using the framework atomic diameters as given by the sigma values using a universal force field (UFF) model.

FIG. 30 is a plot illustrating a simulated pore size distribution of NU-111 using the framework atomic diameters as given by the sigma values using a universal force field (UFF) model.

Figure 31:
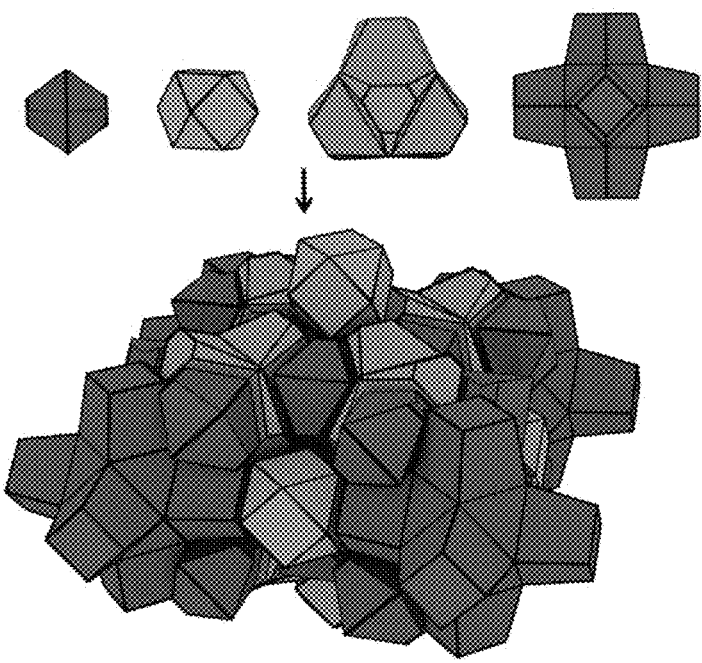
FIG. 31 is a space filling model illustrating the four polyhedra in NU-111 obtained by taking into account the curvature of the ligand as a linker between metal nodes.

FIG. 31 is a space filling model illustrating the four polyhedra in NU-111 obtained by taking into account the curvature of the ligand as a linker between metal nodes.

Figure 32:
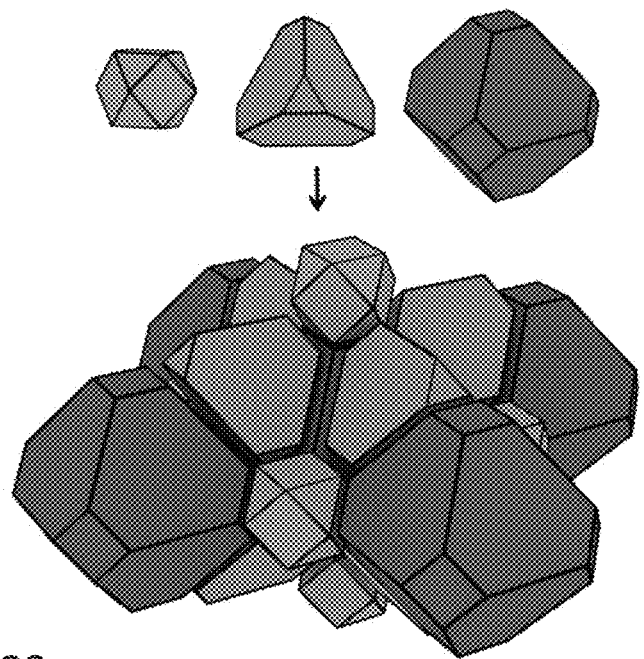
FIG. 32 is a space filling model illustrating the three polyhedra in NU-111 obtained by connecting the metal nodes.

FIG. 32 is a space filling model illustrating the three polyhedra in NU-111 obtained by connecting the metal nodes.

Figure 33:
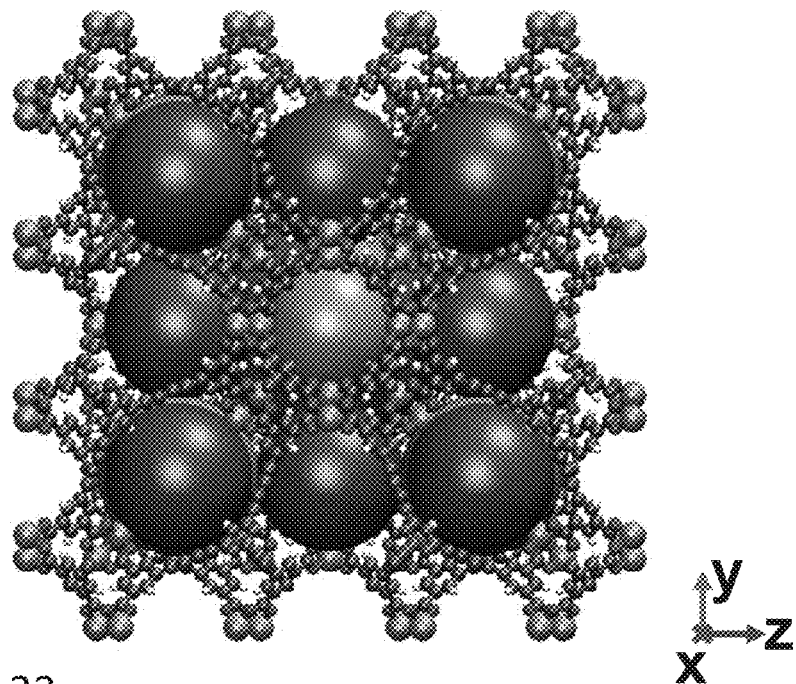
FIG. 33 is an alternative space filling model illustrating the structure of NU-111.

FIG. 33 is an alternative space filling model illustrating the structure of NU-111.

Figure 34:
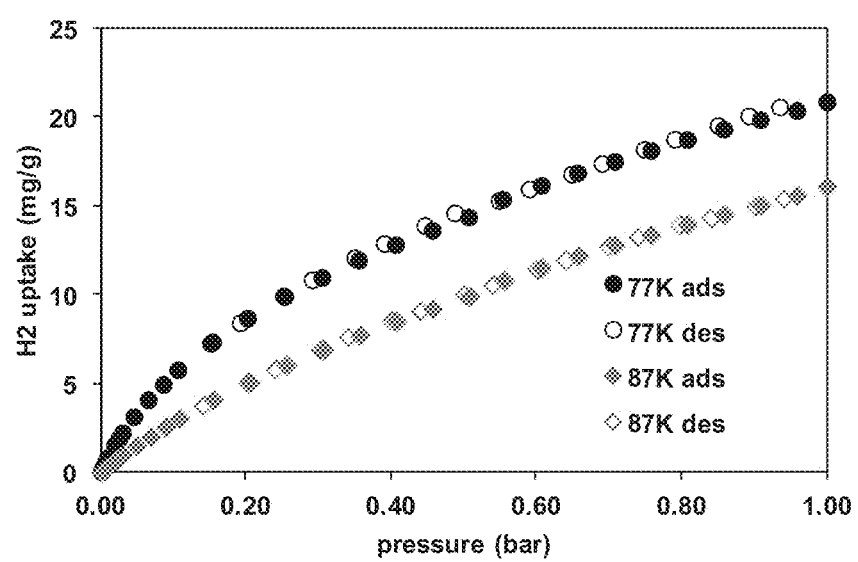
FIG. 34 is a plot illustrating experimental low-pressure H$_2$ isotherms for NU-111 at 77 K and 87 K.

FIG. 34 is a plot illustrating experimental low-pressure $H_2$ isotherms for NU-111 at 77 K and 87 K.

Figure 35:
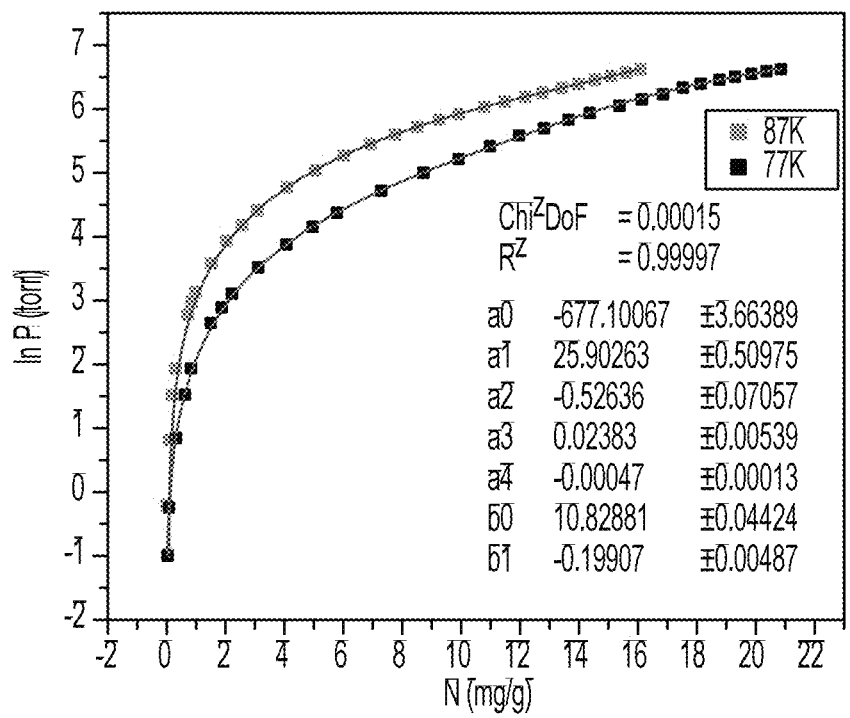
FIG. 35 is a plot illustrating fitting of the hydrogen isotherms (77 K and 87 K) of NU-111 and the corresponding calculations of the isosteric hydrogen heats of adsorption.

FIG. 35 is a plot illustrating fitting of the hydrogen isotherms (77 K and 87 K) of NU-111 and the corresponding calculations of the isosteric hydrogen heats of adsorption.

Figure 36:
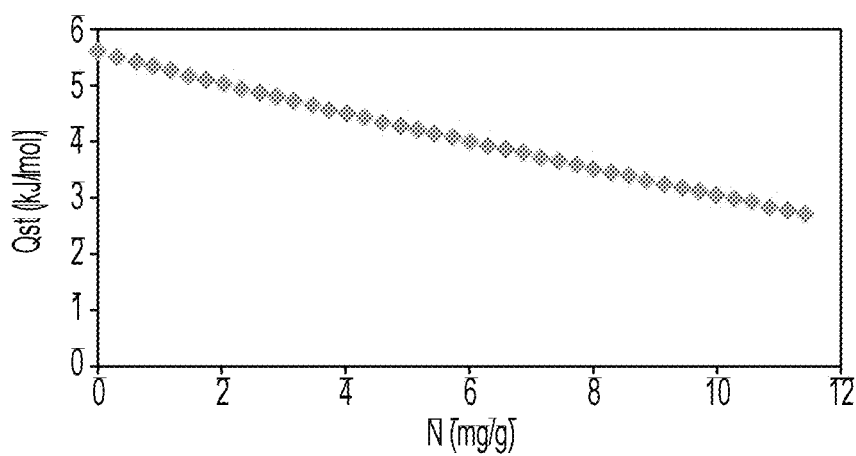
FIG. 36 is a plot of the isosteric H$_2$ heat of adsorption of NU-111.

FIG. 36 is a plot of the isosteric $H_2$ heat of adsorption of NU-111.

Figure 37:
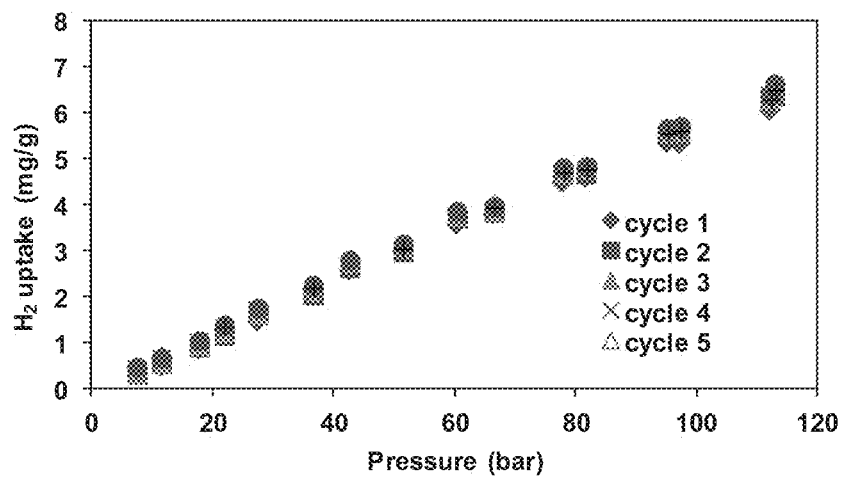
FIG. 37 is a plot of the high-pressure hydrogen adsorption of NU-111 for five cycles at room temperature.

FIG. 37 is a plot of the high-pressure hydrogen adsorption of NU-111 for five cycles at room temperature.

Figure 38:
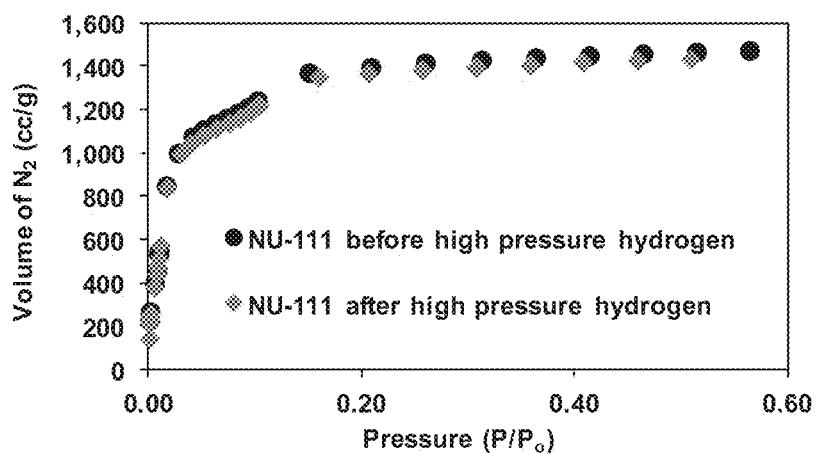
FIG. 38 is a plot of experimental N$_2$ adsorption isotherms for NU-111 at 77 K.

FIG. 38 is a plot of experimental $N_2$ adsorption isotherms for NU-111 at 77 K.

FIGS. 39A-39C are spacing filling models illustrating $H_2$ storage in NU-111 from GCMC simulations at 77K at: a) 1 bar, b) 10 bar, and c) 100 bar.

The disclosures in this application of all references, include patents, are hereby incorporated by reference in their entirety.

The foregoing description of the invention has been presented for purposes of illustration and description. It is not intended to be exhaustive or to limit the invention to the precise form disclosed, and modifications and variations are possible in light of the above teachings or may be acquired from practice of the invention. The drawings and description were chosen in order to explain the principles of the invention and its practical application. It is intended that the scope of the invention be defined by the claims appended hereto, and their equivalents.

What is claimed is:

1. A metal organic framework (MOF) material comprising a Brunauer-Emmett-Teller (BET) surface area greater than 7,010 m²/g.

2. A MOF material wherein the BET surface area is greater than 10,500 m²/g and less than or equal to 14,600 m²/g.

3. A MOF material, wherein the MOF comprises linkers comprising at least two contiguous ethynyl groups.

4. The MOF material of claim 2, wherein the MOF material is activated with supercritical $CO_2$.

5. The MOF material of claim 1, wherein the MOF material comprises linkers each having at least six alkyne bonds.

6. The MOF material of claim 4, wherein the linkers comprise hexa-carboxylated linkers.

7. The MOF material of claim 1, wherein the linkers are selected from formula I, II or III:

Formula I
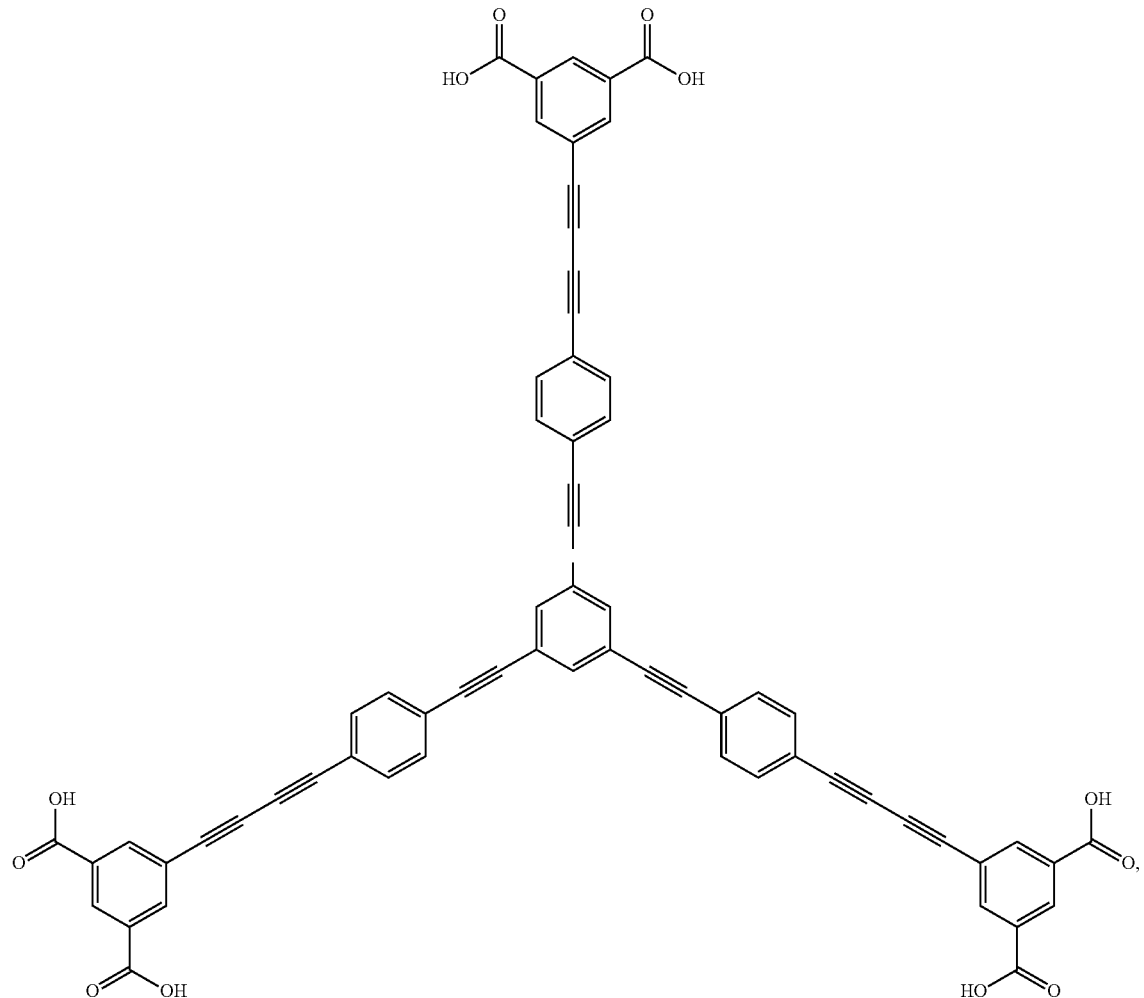
Formula II
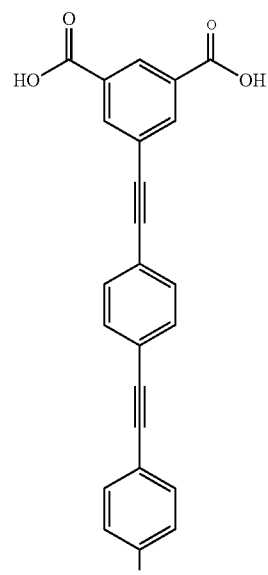

-continued

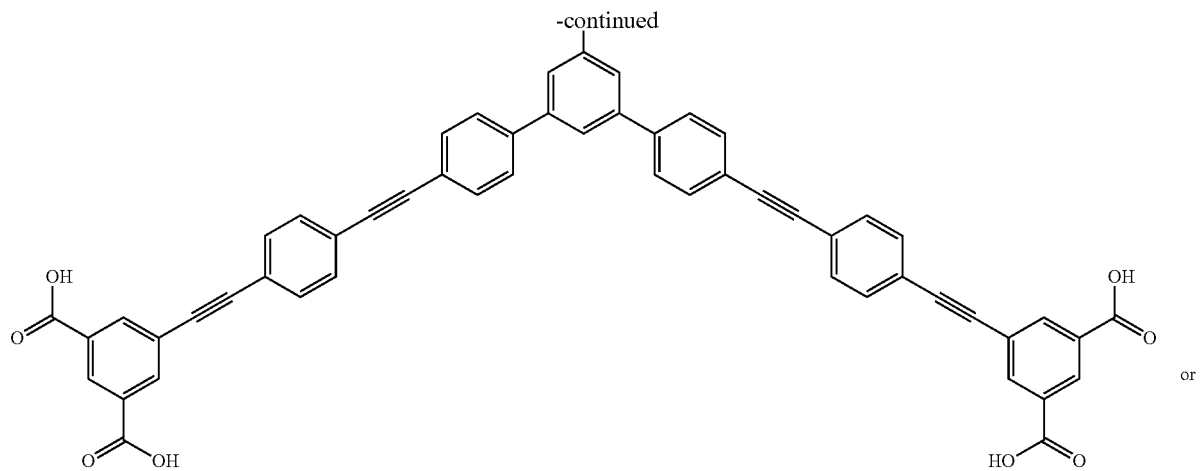

or

Formula III

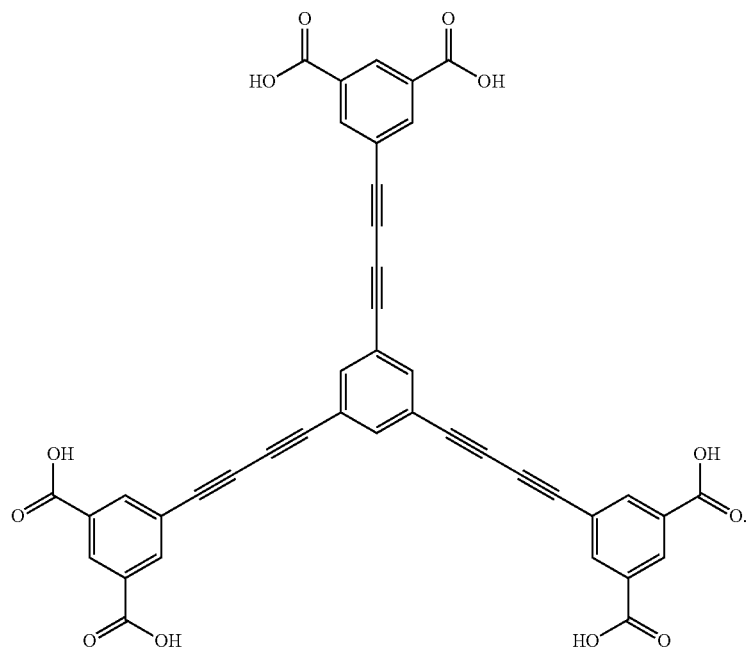

8. The MOF material of claim 1, wherein the MOF material comprises three types of cuboctahedron cages fused to provide for continuous channels.

9. The MOF material of claim 1, wherein the MOF material comprises cuboctahedral cages, truncated tetrahedron cages and truncated cuboctahedral cages.

10. The MOF material of claim 1, wherein the MOF material comprises a pore volume between 3.75 and 4.4 cm$^3$/g.

11. The MOF material of claim 1, wherein the MOF material comprises a hydrogen capacity of 21-69 mg/g at 1-32 bar.

12. The MOF material of claim 11, wherein the MOF material comprises a hydrogen capacity of 135 mg/g at 110 bar and 77K.

13. The MOF material of claim 8, wherein the metal ion is selected from the group consisting of $Li^+$, $Na^+$, $Rb^+$, $Mg^{2+}$, $Ca^{2+}$, $Sr^{2+}$, $Ba^{2+}$, $Sc^{2+}$, $Ti^{4+}$, $Zr^{4+}$, $Ta^{3+}$, $Cr^{3+}$, $MO^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{3+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$, $Cr^{4+}$ and combinations thereof located at nodes of the cuboctahedron cages.

14. A metal organic framework (MOF) material comprising hexa-carboxylated linkers comprising alkyne bonds, wherein the material comprises a Brunauer-Emmett-Teller (BET) surface area greater than 10,500 m$^2$/g.

15. The MOF of claim 14, wherein the MOF material comprises a rht-topology.

16. The MOF material of claim 14, wherein the MOF material comprises three types of cuboctahedron cages fused to provide for continuous channels.

17. The MOF material of claim 14, wherein the MOF material comprises cuboctahedral cages, truncated tetrahedron cages and truncated cuboctahedral cages.

18. A metal organic framework (MOF) material comprising hexa-carboxylated linkers comprising alkyne bonds, wherein the MOF material comprises a pore volume between 3.75 and 4.4 cm$^3$/g.

19. The MOF material of claim 14, wherein the linkers are selected from formula I, II or III:

Formula I
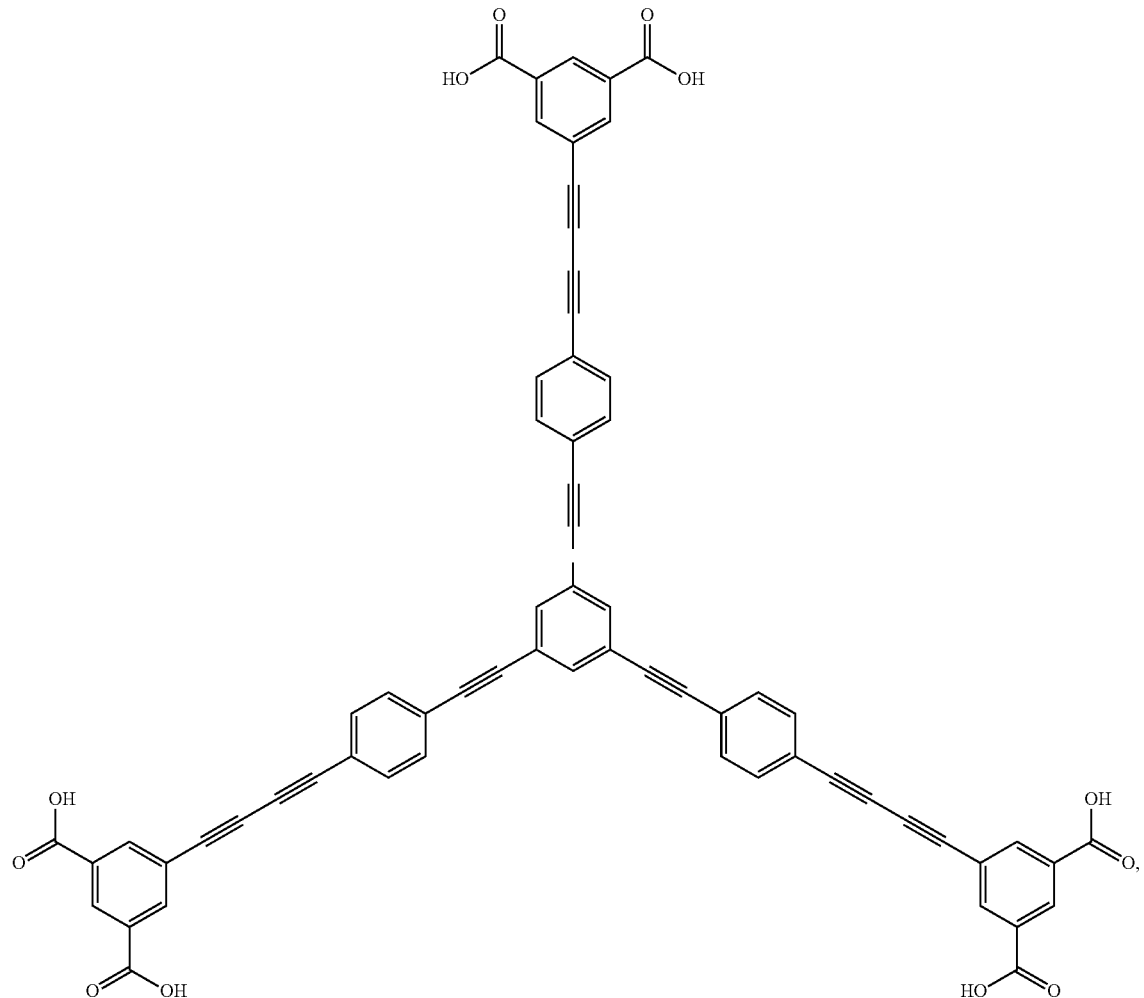
Formula II
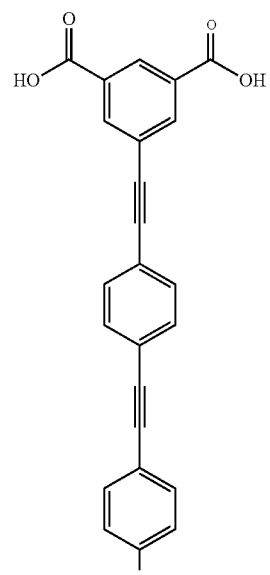

-continued

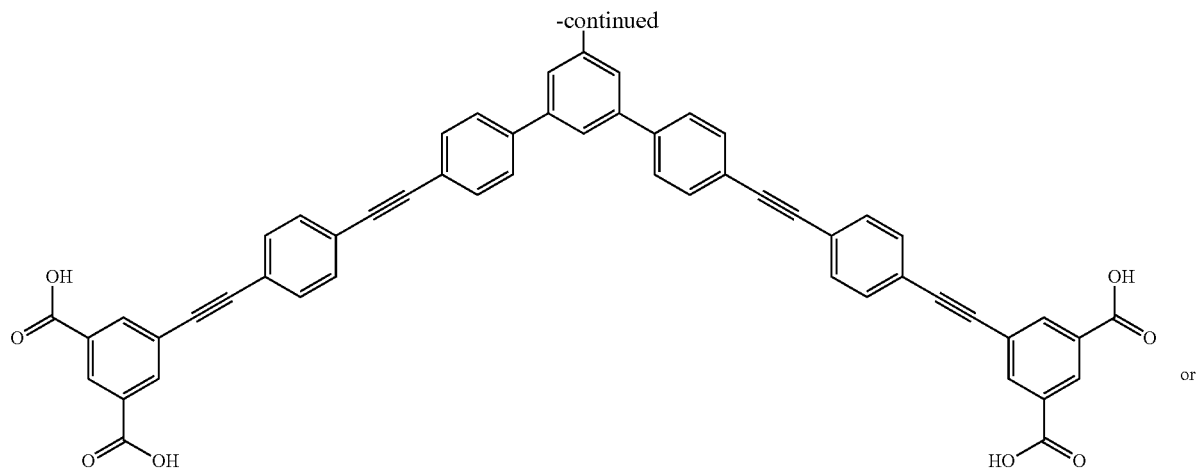

Formula III

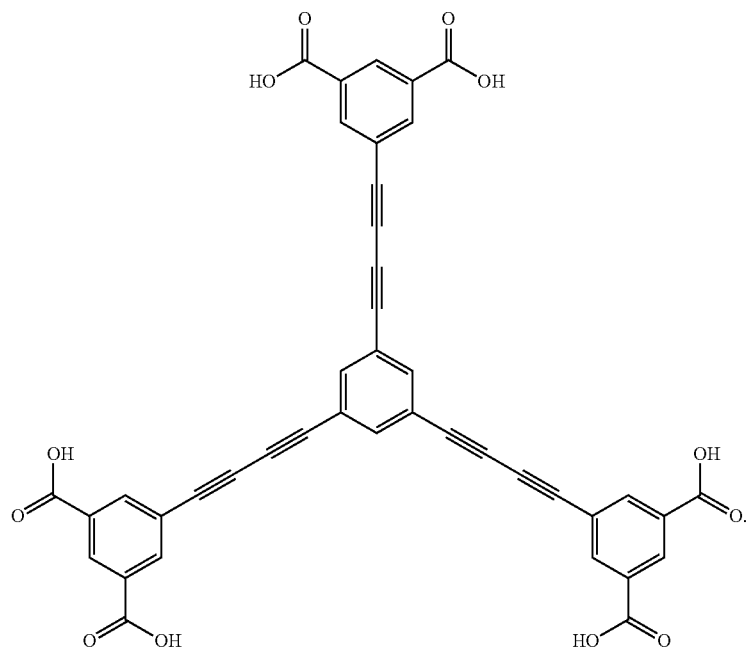

20. The MOF material of claim 16, wherein the metal ion is selected from the group consisting of $Li^+$, $Na^+$, $Rb^+$, $Mg^{2+}$, $Ca^{2+}$, $Sr^{2+}$, $Ba^{2+}$, $Sc^{2+}$, $Ti^{4+}$, $Zr^{4+}$, $Ta^{3+}$, $Cr^{3+}$, $MO^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{3+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$, $Cr^{4+}$ and combinations thereof located at nodes of the cuboctahedron cages.

21. The MOF material of claim 14, wherein each linker comprises at least six alkyne bonds.

22. A metal organic framework (MOF) material comprising three types of cuboctahedron cages fused to provide continuous channels, wherein the MOF material comprises a Brunauer-Emmett-Teller (BET) surface area greater than 10,500 m²/g.

23. A metal organic framework (MOF) material comprising three types of cuboctahedron cages fused to provide continuous channels, wherein the MOF material comprises a pore volume between 3.75 and 4.4 cm³/g.

24. The MOF material of claim 22, wherein the MOF comprises acetylene linkers.

25. The MOF of claim 24, wherein the linkers comprise hexa-carboxylated linkers.

26. A metal organic framework (MOF) material comprising a pore volume of at least 3.75 cm³/g.

27. The MOF material of claim 26, wherein the pore volume is between 3.75 and 4.4 cm³/g.

28. The MOF material of claim 26, wherein the MOF comprises acetylene linkers.

29. The MOF of claim 28, wherein the linkers comprise hexa-carboxylated linkers.

30. The MOF material of claim 26, wherein the MOF material comprises a Brunauer-Emmett-Teller (BET) surface area greater than 10,500 m²/g.

31. A metal organic framework (MOF) material comprising a plurality of linkers selected from formula I, II or III:

Formula I
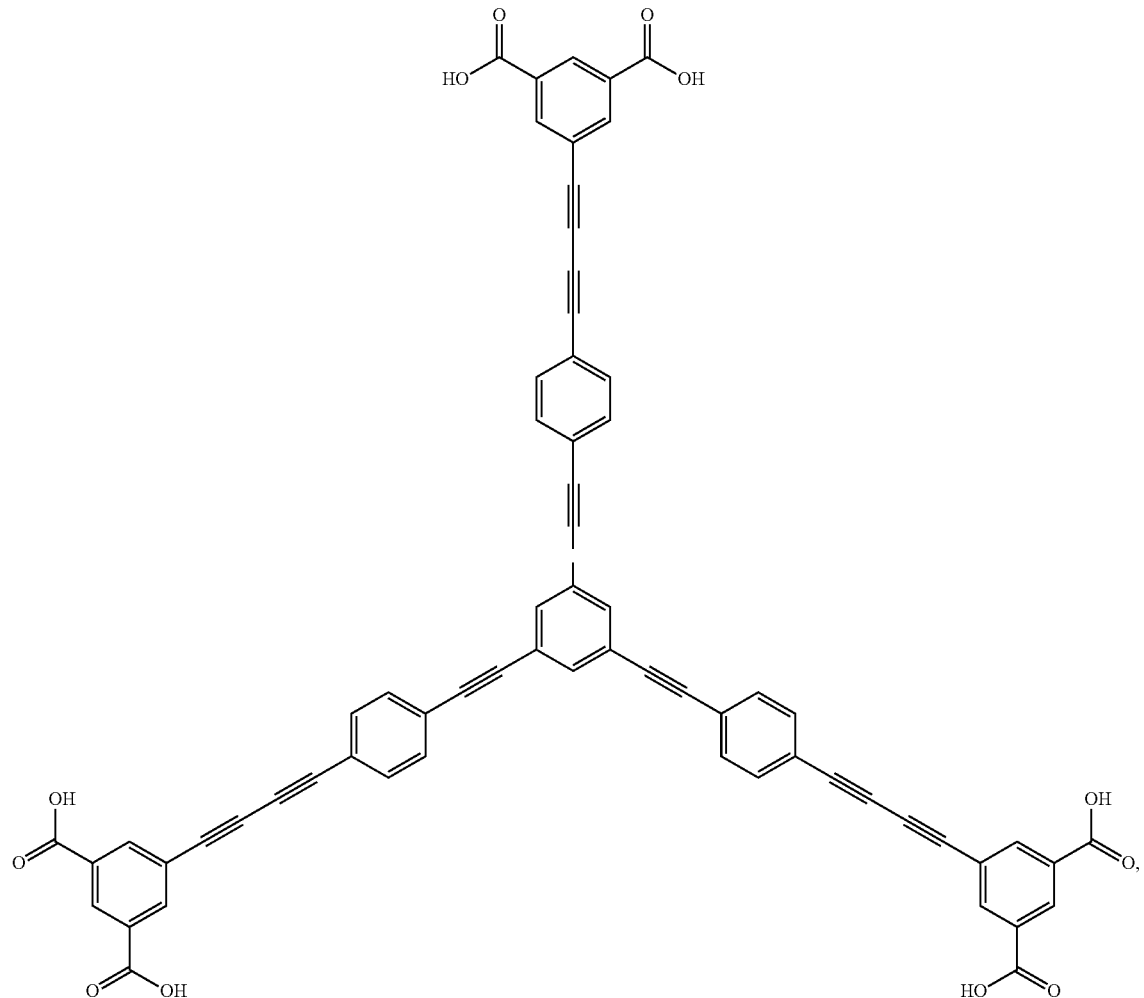
Formula II
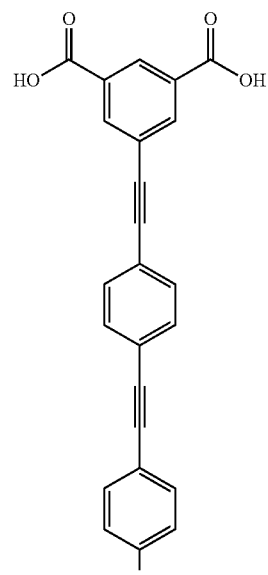

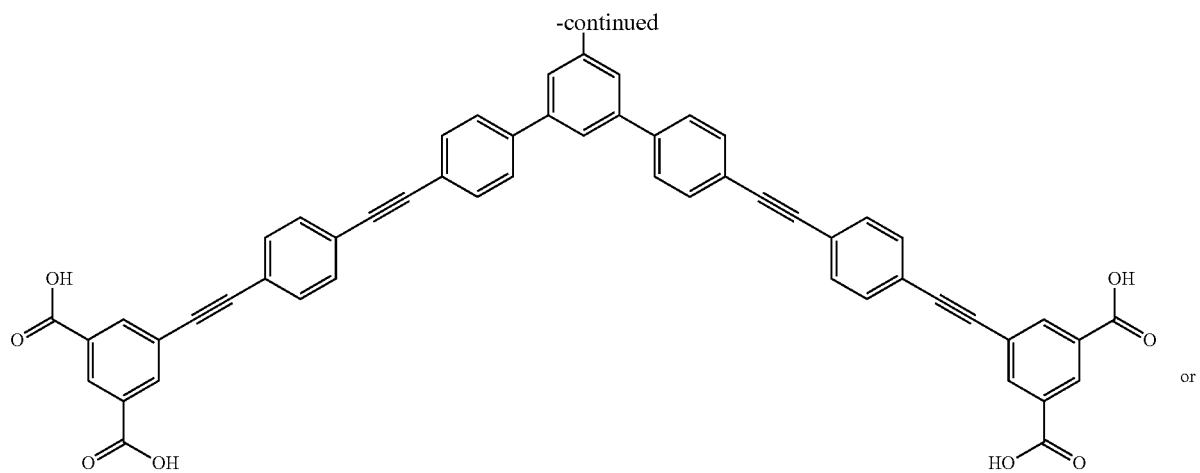

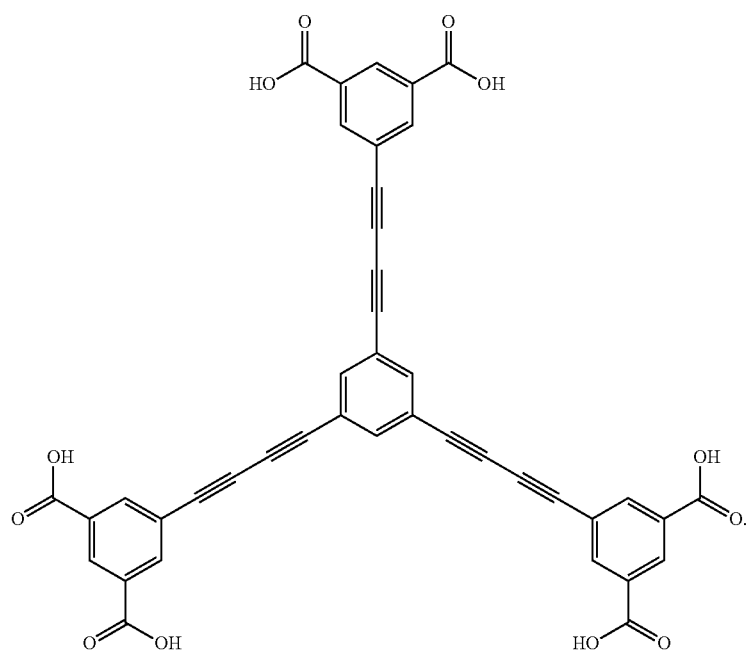

Formula III

32. The MOF material of claim 31, wherein the metal ion is selected from the group consisting of $Li^+$, $Na^+$, $Rb^+$, $Mg^{2+}$, $Ca^{2+}$, $Sr^{2+}$, $Ba^{2+}$, $Sc^{2+}$, $Ti^{4+}$, $Zr^{4+}$, $Ta^{3+}$, $Cr^{3+}$, $MO^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{3+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$, $Cr^{4+}$ and combinations thereof.

33. A method of making a metal organic framework (MOF) material comprising:

saponifying hexaester precursors having alkyne bonds to form a plurality of hexa-carboxylated linkers comprising alkyne bonds; and performing a solvothermal reaction with the plurality of hexa-carboxylated linkers and one or more metal containing compounds to form the MOF material, wherein the hexa-carboxylated linkers are selected from formula I, II or III:

Formula I
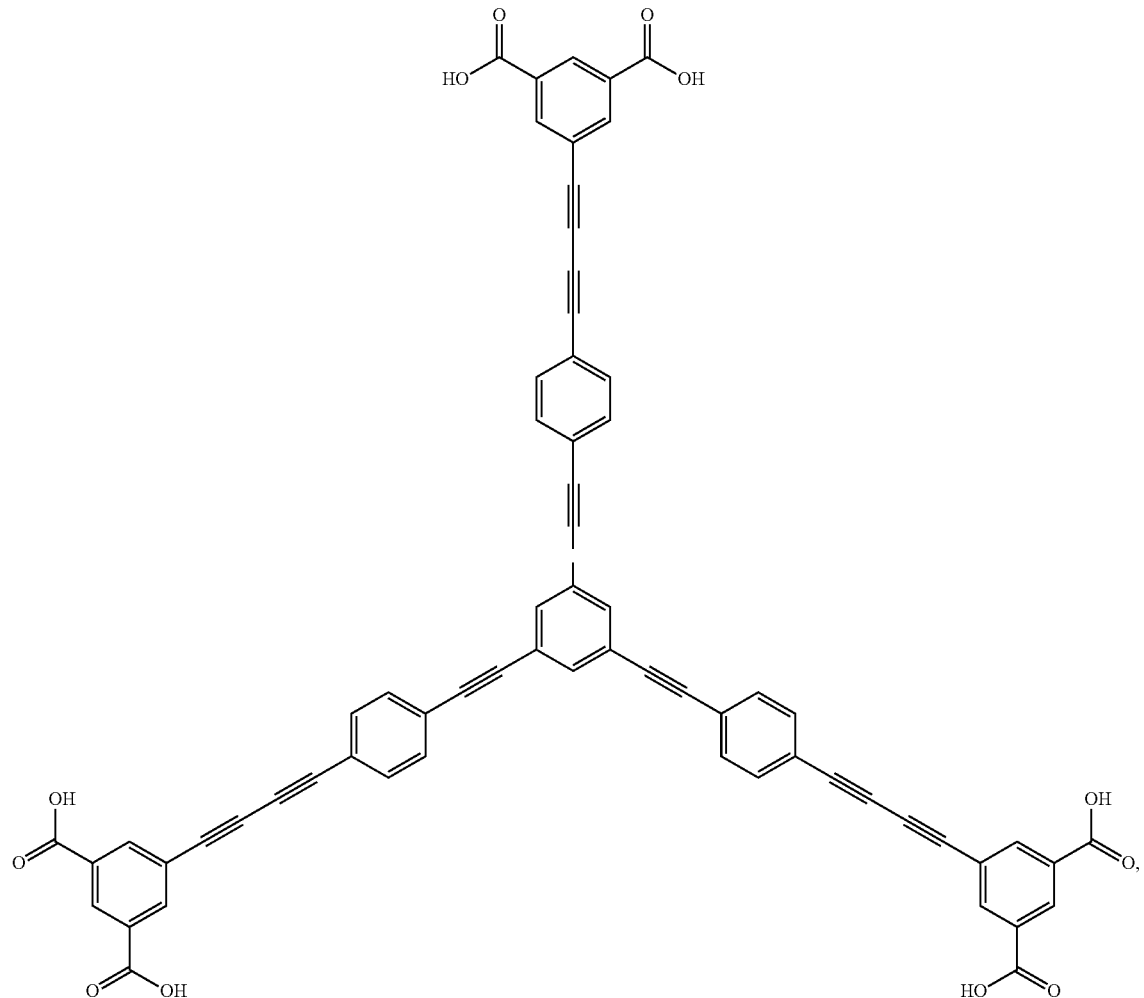
Formula II
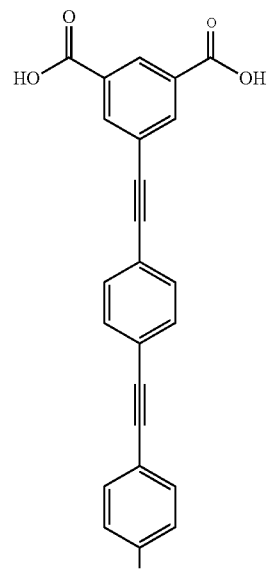

-continued

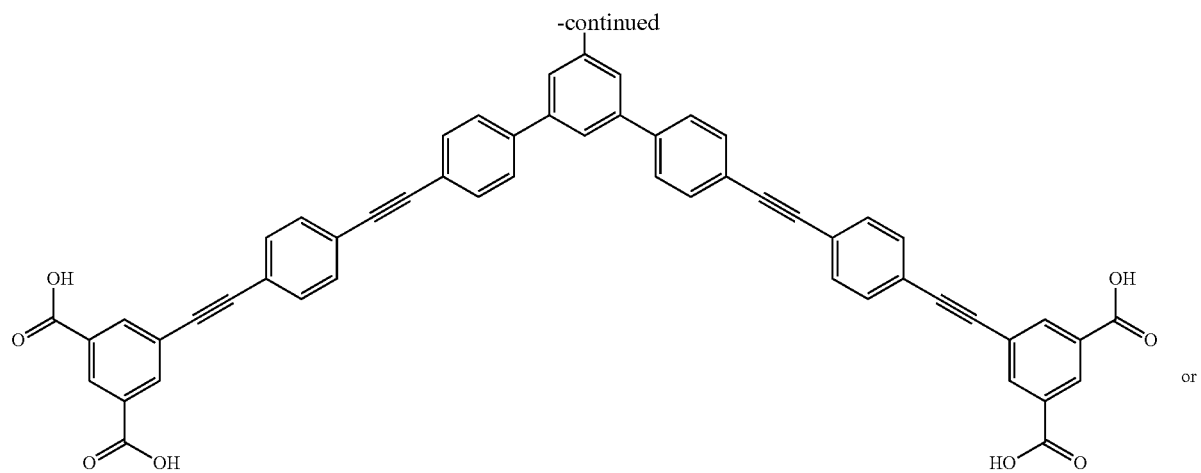

or

Formula III

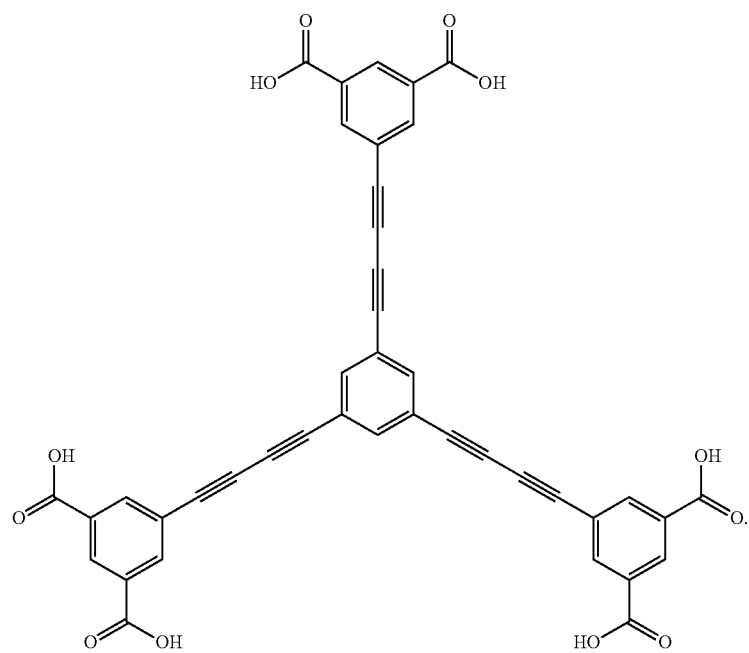

34. The method of claim 33, wherein the one or more metal containing compounds comprises a metal ion selected from the group consisting of $Li^+$, $Na^+$, $Rb^+$, $Mg^{2+}$, $Ca^{2+}$, $Sr^{2+}$, $Ba^{2+}$, $Sc^{2+}$, $Ti^{4+}$, $Zr^{4+}$, $Ta^{3+}$, $Cr^{3+}$, $MO^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{3+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$, $Cr^{4+}$ and combinations thereof.

35. The method claim 34, further comprising activating the MOF material with supercritical $CO_2$.

36. A metal organic framework (MOF) material comprising hexa-carboxylated linkers comprising alkyne bonds, wherein:

each linker has at least 6 alkyne bonds per linker;

each linker has a central benzene ring and at least three struts connected to the central benzene ring;

each strut terminates in a terminal benzene ring and contains two or more alkyne bonds; and each strut further comprises one or more benzene rings located between the central benzene ring and the respective terminal benzene ring, wherein the material comprises a Brunauer-Emmett-Teller (BET) surface area greater than 10,500 m²/g.

37. The MOF of claim 36, wherein the MOF material comprises a rht-topology.

38. The MOF material of claim 36, wherein the MOF material comprises cuboctahedral cages, truncated tetrahedron cages and truncated cuboctahedral cages.

39. A metal organic framework (MOF) material comprising hexa-carboxylated linkers comprising alkyne bonds, wherein:
 each linker has at least 6 alkyne bonds per linker;
 each linker has a central benzene ring and at least three struts connected to the central benzene ring;
 each strut terminates in a terminal benzene ring and contains two or more alkyne bonds; and
 each strut further comprises one or more benzene rings located between the central benzene ring and the respective terminal benzene ring, wherein the MOF material comprises a pore volume between 3.75 and 4.4 cm³/g.

40. The MOF material of claim 36, wherein:
 each linker has 6 or 9 alkyne bonds per linker;
 each linker has three struts connected to the central benzene ring;
 each strut contains two or three alkyne bonds; and
 each strut further comprises one or two benzene rings located between the central benzene ring and the respective terminal benzene ring.

41. The MOF material of claim 40, wherein the linkers are selected from formula I or II:

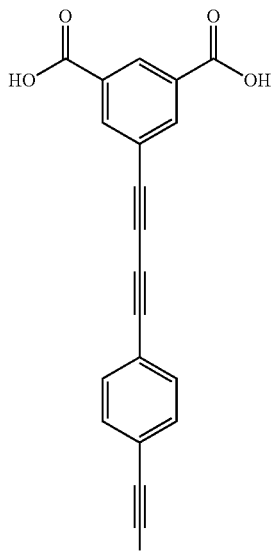

Formula I

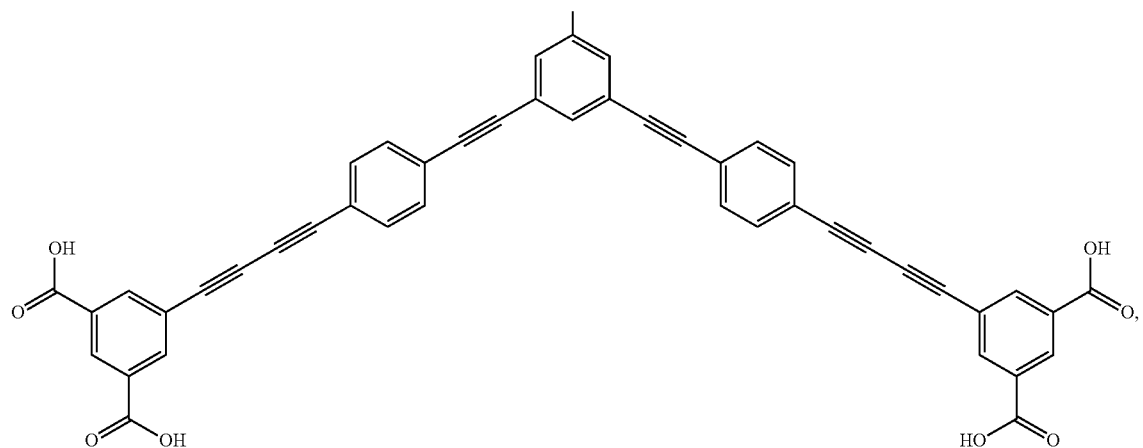

-continued

Formula II

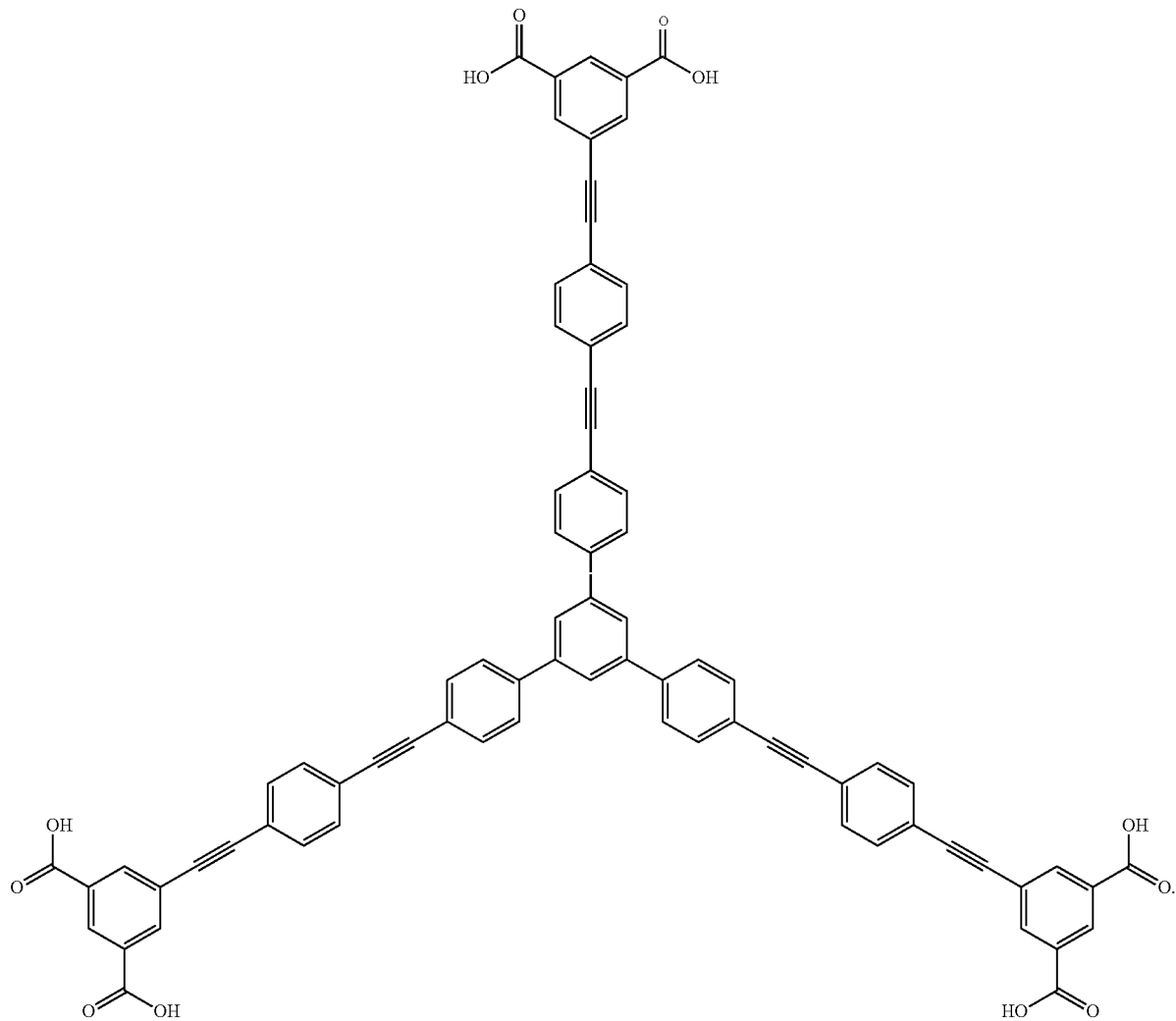

42. The MOF material of claim 16, wherein the MOF further comprises metals ion selected from the group consisting of $Li^+$, $Na^+$, $Rb^+$, $Mg^{2+}$, $Ca^{2+}$, $Sr^{2+}$, $Ba^{2+}$, $Sc^{2+}$, $Ti^{4+}$, $Zr^{4+}$, $Ta^{3+}$, $Cr^{3+}$, $MO^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{3+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$, $Cr^{4+}$ and combinations thereof.

* * * * *